United States Patent
Petrovsky

(10) Patent No.: US 11,110,167 B2
(45) Date of Patent: Sep. 7, 2021

(54) VACCINE ADJUVANT COMPOSITION COMPRISING INULIN PARTICLES

(71) Applicant: Nikolai Petrovsky, Adelaide (AU)

(72) Inventor: Nikolai Petrovsky, Adelaide (AU)

(73) Assignee: VAXINE PTY LTD, Adelaide (AU)

( * ) Notice: Subject to any disclaimer, the term of this patent is extended or adjusted under 35 U.S.C. 154(b) by 0 days.

(21) Appl. No.: 15/597,371

(22) Filed: May 17, 2017

(65) Prior Publication Data

US 2018/0169223 A1   Jun. 21, 2018

Related U.S. Application Data

(63) Continuation of application No. 14/127,489, filed as application No. PCT/EP2012/061748 on Jun. 19, 2012, now abandoned.

(60) Provisional application No. 61/498,557, filed on Jun. 18, 2011.

(51) Int. Cl.
| | |
|---|---|
| *A61K 39/39* | (2006.01) |
| *A61K 31/715* | (2006.01) |
| *A61K 39/145* | (2006.01) |
| *A61K 39/205* | (2006.01) |
| *A61K 39/29* | (2006.01) |
| *A61K 39/12* | (2006.01) |
| *A61K 39/35* | (2006.01) |
| *A61K 39/395* | (2006.01) |
| *A61K 39/00* | (2006.01) |

(52) U.S. Cl.
CPC ............ *A61K 39/39* (2013.01); *A61K 31/715* (2013.01); *A61K 39/12* (2013.01); *A61K 39/145* (2013.01); *A61K 39/205* (2013.01); *A61K 39/292* (2013.01); *A61K 39/35* (2013.01); *A61K 39/395* (2013.01); *A61K 2039/5252* (2013.01); *A61K 2039/55511* (2013.01); *A61K 2039/55561* (2013.01); *A61K 2039/55583* (2013.01); *C12N 2730/10134* (2013.01); *C12N 2760/16134* (2013.01); *C12N 2760/20134* (2013.01)

(58) Field of Classification Search
CPC ...................................................... A61K 39/39
USPC ...................................................... 424/130.1
See application file for complete search history.

(56) References Cited

PUBLICATIONS

Watzl et al., British Journal of Nutrition (2005), 93, Suppl. 1, S49-S55.*
N. Petrovsky (Vaccine 2006).*
Silva et al (Immun. and Cell Biol. 82: 611-616, 2004).*
Bosscher et al. (abstract) Nutr Res Rev.( 2006).*

* cited by examiner

*Primary Examiner* — Gyan Chandra

(57) ABSTRACT

The present invention provides a pharmaceutically acceptable composition comprising: particles of inulin; a substance comprising or consisting of one or more pathogen-associated molecular patterns (PAMPs), and an antigen for use inducing or modulating an immune response in a subject, such as modulating an immune response to an antigen or allergen and/or as a vaccine.

7 Claims, 17 Drawing Sheets

Figure 1:
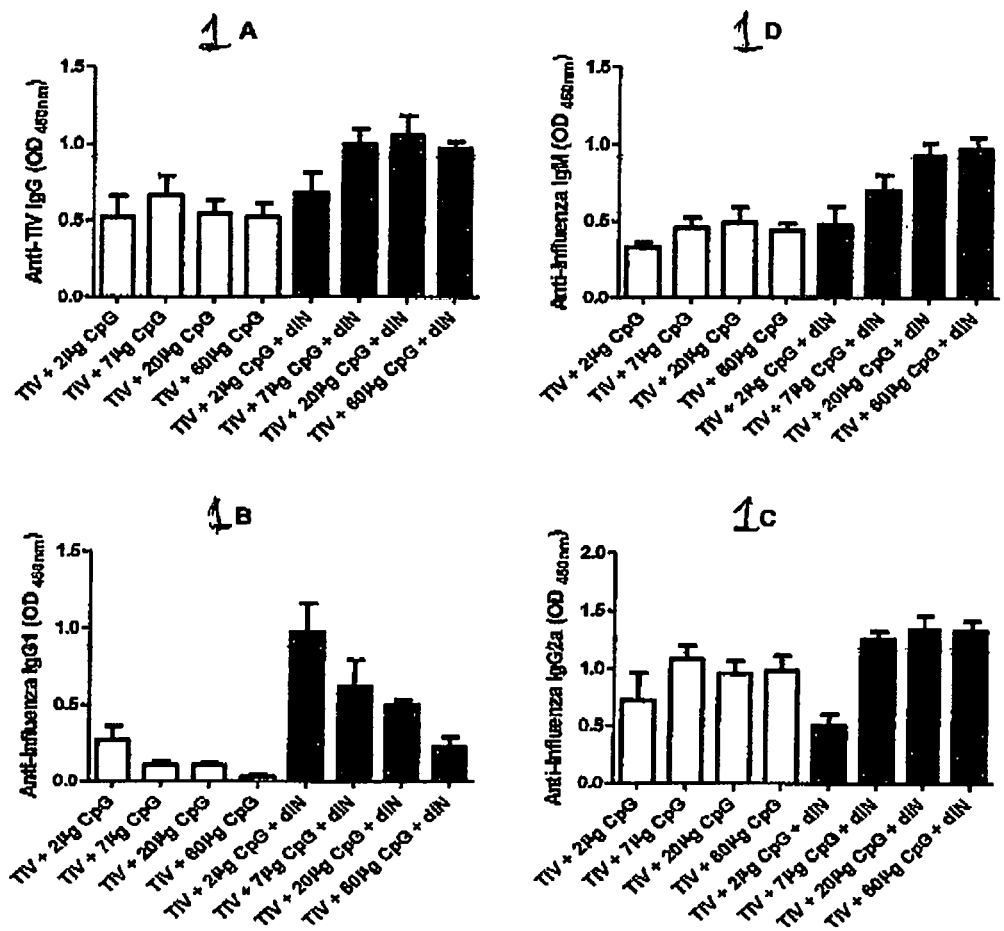

6A.

6B.

Hemagglutination inhibition and neutralizing antibody titers during vaccination

10A. Hemagglutination-Inhbition Antibody at booster dose, Day -21 prior to challenge

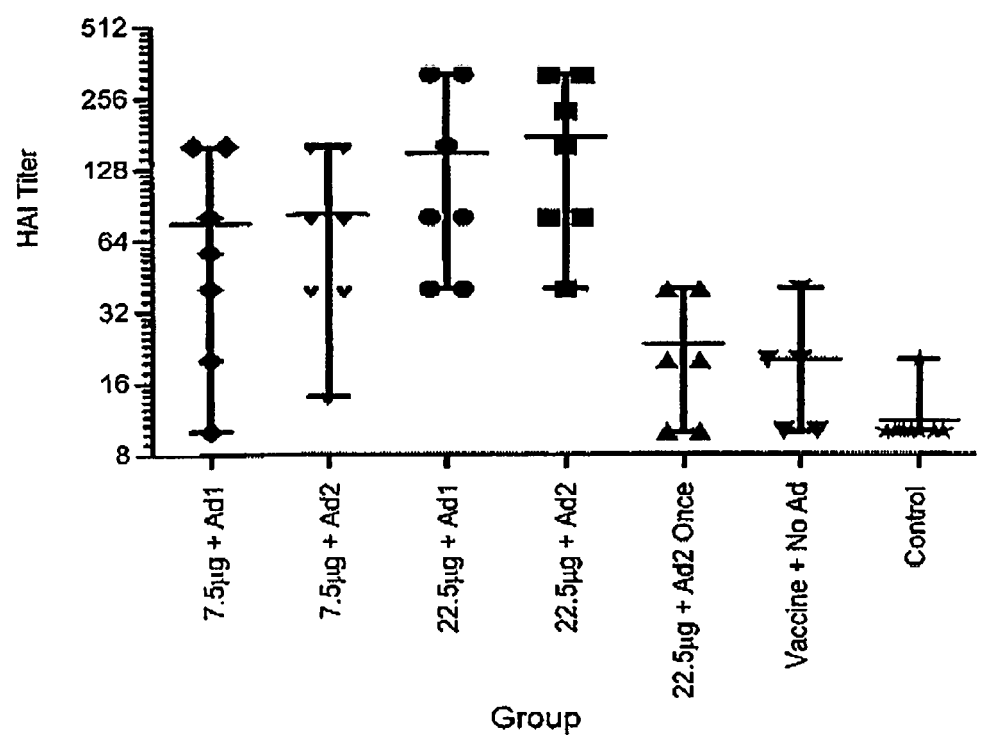

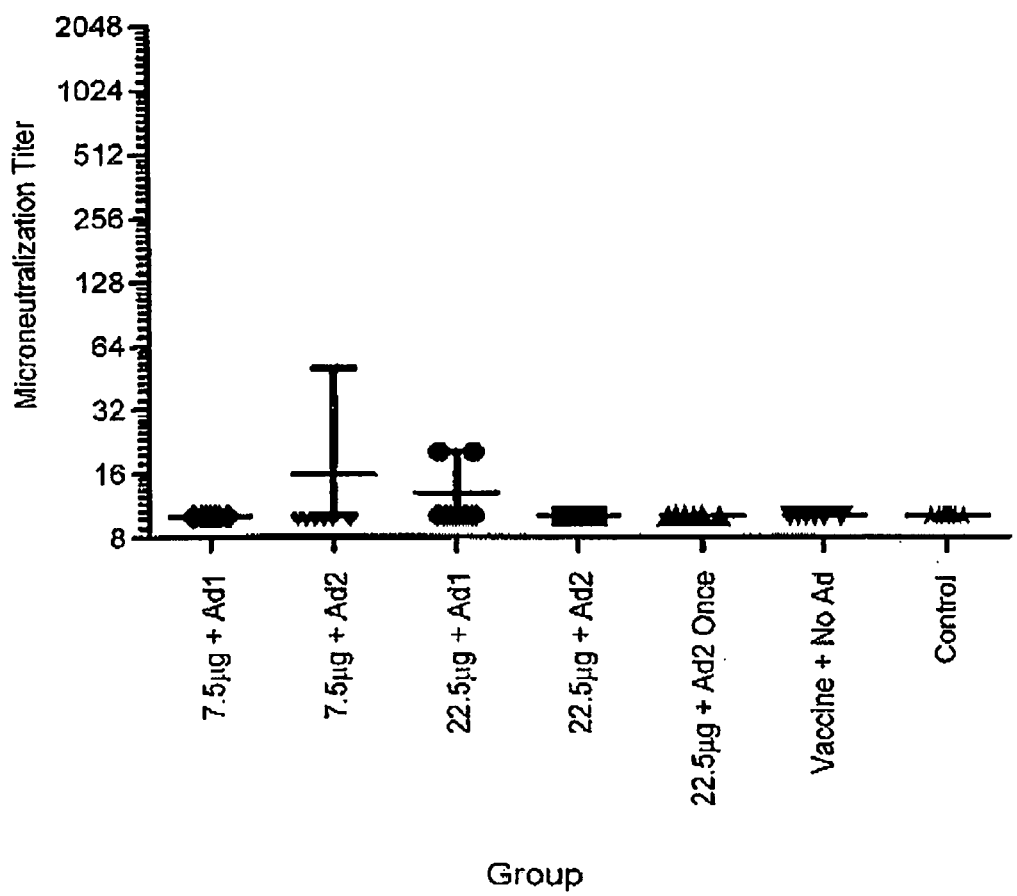

Weight Change after challenge

12A

12B

12C

12D

12E

12F

12G

VACCINE ADJUVANT COMPOSITION COMPRISING INULIN PARTICLES

CROSS-REFERENCE TO RELATED APPLICATIONS

This application is a continuation application of and claims priority benefit of U.S. patent application Ser. No. 14/127,489, which was filed on Dec. 19, 2013 and claimed priority to International Patent Application PCT/EP2012/061748 filed Jun. 19, 2012 which claimed priority to U.S. Provisional Application No. 61/498,577, filed on Jun. 19, 2011, all of which are incorporated herein in their entirety.

FIELD OF THE INVENTION

The present invention relates to novel compositions suitable for the stimulation, modulation or enhancement of an immune response.

BACKGROUND

The listing or discussion of an apparently prior-published document in this specification should not necessarily be taken as an acknowledgement that the document is part of the state of the art or is common general knowledge. As known in the art, microbial-derived compounds that trigger innate immune activation also enhance the adaptive immune response to a co-administered vaccine antigen. Such compounds are now known to comprise or mimic pathogen-associated molecular patterns (PAMPs), where a PAMP is a structurally conserved motif derived from a pathogen that is immunologically distinguishable from host molecules, and is recognised by an innate immune receptor (Heine et al., 2005). PAMPs are present in certain types of protein, lipid, lipoprotein, carbohydrate, glycolipid, glycoprotein, and nucleic acids expressed by particular pathogens and include triacyl lipopeptides, porins, glycans, single and double stranded RNA, flagellin, lipotechoic acid, N-formymethionine, and bacterial or viral DNA, amongst others. PAMPs act as innate immune activators by binding to PAMP-specific innate immune receptors such as toll-like receptors (TLR), NOD-like receptors, RIG ligase receptors and C-type lectins. This leads to activation of inflammatory gene pathways in immune cells.

What these PAMP compounds have in common is that they all activate the innate immune system and induce inflammatory gene pathways, in particular through activating Nuclear Factor-Kappa B (NFκB), the master transcriptional regulator of inflammatory gene activation. This inflammation in turn may lead to enhancement of an adaptive immune response to a co-administered antigen, as a by-product or downstream effect of the innate immune activation. The enhancement by a separate substance of an adaptive immune response to a co-administered antigen is known as an "adjuvant" effect.

Without wishing to be restricted by theory, it is accepted by those skilled in the art that the common factor that links all compounds that possess adjuvant activity is that they induce immune "danger signals" (Matzinger, 2002) leading to activation of innate immune and thereby activation of NFκB and other inflammatory pathways. Danger signals that provide immune adjuvant effects can be generated by local tissue damage, e.g. induced by injection of inflammatory substances such as oil emulsions, or more specifically through binding of PAMPs to innate immune receptors whose role is to detect pathogen invasion and tissue damage. PAMP-associated danger signals thereby alert the innate immune system of the need to mount a defensive inflammatory response against the perceived threat. Following the activation of these danger-sensing PAMP receptors, inflammatory gene signalling pathways including the key NFκB pathway are activated leading to secretion by immune cells such as monocytes of key inflammatory effectors including tumour necrosis factor (TNF)-α, interleukin (IL)-1, IL-6, IL-8 and IL-12, amongst others. These inflammatory mediators released in response to PAMP activation are believed in the art to be critical to the ability of PAMPs to enhance antigen-specific adaptive immune responses, with high-throughput cell-based screening assays designed to identify new adjuvant compounds reliant upon their ability to induce inflammatory cytokines such as TNF-α, IFN-γ, IL-1, IL-8 or IL12 as the readout of potential adjuvant activity (Buckner et at, 2008).

Conceptually, two or more such innate immune activators when combined together induce even stronger danger signals, generate higher levels of inflammatory gene activation, and thereby are predicted to show increased adjuvant potency (Querec et al., 2006; Kasturi et al, 2011). However, as known by those skilled in the art, the problem of using PAMPs either singly or, more particularly, combined together as immune modulators or vaccine adjuvants is that the inflammatory effects are highly toxic and hence the ability to achieve enhancement of an adaptive immune response in this way is hindered by severe dose-limiting local and systemic inflammation-associated toxicity which is correspondingly magnified as the dose of the innate immune activator is increased. For example, even the combination of a partially detoxified PAMP analogue, monophosphoryl lipid A (MPL), with aluminium hydroxide ("alum") adjuvant in a hepatitis B surface antigen (HBsAg) vaccine caused significantly more local injection site reactions, fever and other systemic side effects than HBsAg with alum adjuvant alone (Tong et al., 2005).

Increased vaccine reactogenicity and toxicity when two or more innate immune activators are combined in a vaccine formulation is a major barrier to regulatory approval of such adjuvant combinations, even where there might be a favourable impact on vaccine immunogenicity (Petrovsky et al, 2008). Furthermore, not all combinations of innate immune activators are favourable from an immunogenicity standpoint, such that some combinations of innate immune activators produce an adaptive immune response to a co-administered antigen that is no better than the individual innate immune activator components alone, and some innate immune activator combinations even result in lower antigen-specific responses than with each individual innate immune activator used alone. For example, humans immunized with C-terminal recombinant malaria circumsporozoite antigen with alum alone achieved higher antigen-specific antibodies than subjects receiving the combination of alum with MPL (Gordon et al., 1995).

The vaccine art recognizes the use of certain substances called adjuvants to potentiate an immune response when used in conjunction with an antigen. As used herein, the term "adjuvant" will be understood to mean any substance or material that when administered together or in conjunction with an antigen increases the immune response to that antigen. The problem with pure recombinant or synthetic antigens used in modern day vaccines is that they have poor immunogenicity when compared to less pure older-style live or killed whole cell vaccines. This has created a major need for development of effective adjuvants. Adjuvants are further used to elicit an immune response that is faster or greater than would be elicited without the use of the adjuvant. In addition, adjuvants may be used to create an immunological response using less antigen than would be needed without the inclusion of adjuvant, to increase production of certain antibody subclasses that afford immunological protection or to enhance particular cellular immune responses (e.g., CD4 or CD8 T cell memory responses) (Petrovsky et al., 2004).

Known adjuvants include aluminium salts (generically referred to as "alum" adjuvants). With few exceptions, alum adjuvants remains the only adjuvants licensed for human use in many countries. Although alum adjuvants are often useful to induce a good antibody (Th2) response to co-administered antigen(s), they are largely ineffective at stimulating a cellular (Th1) immune response, which are important for protection against many pathogens. Furthermore, alum has the potential to cause rare severe local and systemic side effects including sterile abscesses, eosinophilia and macrophagic myofasciitis (Israeli et al., 2010). There is also community concern regarding the possible role of aluminium salts in neurodegenerative diseases such as Alzheimer's disease (Bondy, 2010). Other licensed adjuvants including MF59, a squalene oil emulsion adjuvant that is licensed in Europe as part of an influenza vaccine (Durando et al., 2010) and AS04, a combination of aluminium hydroxide and monophosphoryl lipid A (MPL), that is licensed in Europe in a hepatitis B vaccine.

However, the biggest single barrier to the development of improved human adjuvants whether used alone or together is the problem of local and systemic toxicity and adverse reactions. This is a particular problem for development of childhood vaccines where safety is paramount. Vaccine-mediated adverse reactions include inflammation and granuloma formation at the site of injection, pyrogenicity, nausea, adjuvant arthritis, uveitis, eosinophilia, allergy, anaphylaxis, organ specific toxicity or immunotoxicity, i.e. the liberation of toxic quantities of inflammatory cytokines (Petrovsky et al). Such extreme toxicity hampers the use of otherwise highly potent adjuvants such as complete Freund's adjuvant (CFA), with this toxicity principally reflecting excessive activation of inflammatory pathways by innate immune activator adjuvants. Compounds or combined formulations that can successfully enhance adaptive immune responses, yet at the same time are well tolerated, safe and non-toxic to the host remain highly elusive, and of the hundreds of compounds known to be innate immune activators and possess vaccine adjuvant potential, less than a handful are approved for use in humans, and just two compounds, alum and MPL, being approved by the FDA for human vaccine use in the USA market.

Ideally, adjuvant formulations should be suited for use with a wide range of potential vaccine antigens and be safe for use in low responder populations including children, the elderly and immuno-compromised individuals. Thus, one of the major remaining challenges in vaccine research remains how to increase vaccine potency without inducing increased local or systemic toxicity. The difficulty of achieving this objective is exemplified by the fact alum adjuvants, 90 years after their discovery, continue to dominate human vaccine use.

Because for the most part the mechanisms of adjuvant action are not known, the art has generally not been able to predict on an empirical basis whether a particular compound, or mix of compounds, will have adjuvant activity. Similarly there is no way provided in the art to predict on an empirical basis whether a particular adjuvant, or mix of adjuvants, will be safe and well tolerated.

Moreover, each adjuvant-antigen composition may generate a different type of immune response, which may or may not provide enhanced protection against a relevant pathogen. For example, different types of adaptive immune response have been described, for example T helper (Th)1, Th2 and Th17 responses. For a particular pathogen, one adaptive immune response may be more favourable for providing protection than others. For example, for Leishmania a Th1 vaccine response is protective whereas a Th2 response may cause an unfavourable outcome. For other pathogens the converse may be true, such that a Th2 vaccine response is beneficial whereas a Th1 response is detrimental, and in even other situations a Th17 vaccine response may be desired.

This means that, in order to find successful adjuvant-antigen vaccine combinations, the art has relied on extensive trial and error testing. Even after extensive validation in a animal models, examples abound of adjuvant-antigen combinations that were effective in animal challenge models and were ineffective or even detrimental when administered to humans. An example of the former is the ineffectiveness of alum adjuvants in human influenza vaccines, despite showing enhanced protection in animal models. Another example is respiratory syncytial virus (RSV) vaccine, which when formulated with alum adjuvant, enhanced immunogenicity and protection in animal models of RSV infection but caused worsened disease and increased deaths from RSV infection when administered to human children, an effect thought to be mediated by the vaccine inducing the wrong type of immune response, namely a Th2 rather than Th1 response (Prince et al., 1986).

β-D-(2-1) polyfructofuranosyl α-D-glucose (commonly known as inulin) is a polysaccharide that (as disclosed by WO 87/02679, WO 2006/024100, and WO 2011/032229) develops useful properties when crystallised into stable particulate structures. Inulin has a relatively hydrophobic, polyoxyethylene-like backbone, and this unusual structure plus its non-ionised nature allows re-crystallisation and easy preparation in a very pure state. Inulin in its raw state is generally soluble in warm water but, as disclosed by WO 87/02679, WO 2006/024100 and WO 2011/032229, can with specific treatments be crystallised into more stable polymorphic forms, including the previously described gamma (gIN), delta (dIN) and epsilon (eIN) forms.

Such inulin particles (hereinafter collectively referred to simply as 'inulin particles') are largely insoluble at normal mammalian body temperature and have been found to possess excellent adjuvant properties. Without wishing to be bound by theory, the stable conformation of these inulin forms are important for inulin particles to remain intact long enough to bind and interact with immune cells. Hence, when suspensions of inulin particles are heated to high temperature so as to dissociate and solubilise the inulin particles, the resulting inulin solution loses all immunological and vaccine adjuvant activity. Inulin particles share properties relevant to their adjuvant action including the ability to enhance antigen processing and presentation by appropriate immune cells, properties not shared by more soluble inulin formulations.

Without wishing to be bound by theory, we have observed that the immune effects of each inulin polymorphic form increases in series as its temperature of solubility increases, such that particles of dIN are more temperature stable and adjuvant potent than gIN, and particles of eIN are in turn more temperature stable and adjuvant potent than particles of dIN. Thus, gIN, dIN or eIN form are progressively more adjuvant active.

As disclosed by WO 87/02679, WO 2006/024100, and WO2011/032229, stable inulin formulations comprising gIN, dIN or eIN particles of appropriate size and composition are able to enhance humoral and/or cellular adaptive immune responses to co-administered vaccine antigens.

As described further in the present application, when studying the biological effects of inulin particles, we have now made the surprising finding that anti-inflammatory effects are also provided. More specifically, it has been found that, when cultured with human peripheral blood mononuclear cells (PBMC) or mouse splenocytes, inulin particles will upregulate rather than down-regulate expression of anti-inflammatory genes. Conversely, they will downregulate the expression of many pro-inflammatory genes and, in particular, inulin particles did not activate NFκB expression.

This was a highly surprising finding as it appears to contradict the widely accepted 'danger model' whereby all adjuvants are thought to work via activation of pro-inflammatory innate immune pathways through activation of NFκB and/or the inflammasome and thereby induce production of inflammatory cytokines such as TNF-α and IL-1. The danger model was largely developed based on the known adjuvant action of PAMPs, for example TLR agonists that activate the innate immune system but also directly or indirectly increase adaptive immune responses to co-administered antigens. PAMP-derived adjuvants all share the property that they induce pro-inflammatory cytokines including tumour necrosis factor (TNF)-a, interleukin (IL)-1, and IL-6 production. PAMPs induce these cytokines through activation of NFκB, a master transcription factor that induces inflammation in immune cells (Werling et al., 2003). Similarly, alum adjuvants and oil emulsion adjuvants activate the inflammasome, a tissue damage sensing mechanism which when activated also leads to the production of inflammatory cytokines including IL-1 (Eisenbarth et al, 2008). By contrast, inulin particles when incubated with human PBMC, surprisingly do not activate NFκB but instead downregulate pro-inflammatory gene expression including interleukin (IL)-1. IL1RAP, IL18RAP, cyclooxygenase (Cox)-2, NALP3, NLRP3, NLRP12, CARD12, IFIT1, IFIT2, IFIT3, IDO, CXCL5, CXCL6, CXCR7, CD14, TLR4, NOD2, formyl receptors 1,2 and 3, and upregulate genes associated with downregulation of innate immune responses and with inhibition of the pro-inflammatory IL1 cytokine pathway, including IL-1 receptor antagonist (IL-1RA), IL1RN, and IL1R2 as well as IL18BP, CD33, ATF3, TREM1, PPAR-gamma, FCRL2 and CD36. This data indicated that inulin particles have anti-inflammatory activity, leading to the first aspect of the current invention, as discussed below. We therefore sought to test the ability of inulin particles to inhibit inflammation, with a view to potential use of inulin particles to treat or prevent inflammatory disease.

To test whether inulin particles could reduce the side effects of pro-inflammatory immune activators and adjuvant formulations, inulin particles were tested, in vitro and in vivo, with a range of PAMPs and innate immune activators including a broad range of TLR agonists, with the expectation that the inulin particles would inhibit both the inflammation and also inhibit the adjuvant activity induced by the PAMPs and other innate immune activators. The results were unexpected and surprising and led to the second aspect of the current invention. As predicted, the co-administration of inulin particles together with a classical PAMP innate immune activator such as CpG-motif containing oligonucleotides (ODN), down-modulated the inflammatory gene activation mediated by the CpG ODN. What was unexpected, however, was that, paradoxically, despite successfully inhibiting the inflammatory signals induced by the PAMP, the inulin particles actually enhanced the adjuvant activity of the PAMP on an adaptive immune response as measured by their ability to increase the protective memory immune response against a co-administered antigen. This finding was surprising given that the inulin particles were predicted to downregulate the pro-inflammatory 'danger signals' and innate immune activation induced by the co-administered PAMPs. Under the prevailing danger signal model of adjuvant action, inulin particles, by inhibiting inflammatory responses, would have been expected to reduce the PAMP adjuvant activity.

We have subsequently repeated this experiment with a wide variety of further PAMP adjuvants, and have consistently observed the same beneficial effects of inulin particles, that is, reduction in inflammation yet enhanced adjuvant activity. In view of the previous lack of predictability in the art when combining adjuvants in a single composition, the consistent results obtained when combining inulin particles with all tested PAMPs was a further unexpected result. Without wishing to be restricted by theory, the downregulation by inulin particles of pro-inflammatory innate immune pathways induced by PAMPs, may paradoxically enhance the ability of the PAMPs to stimulate an adaptive immune memory response, suggesting that pro-inflammatory innate immune cytokines such as IL1 induced by PAMPs may, particularly if their levels are too high, suppress rather than stimulate an adaptive immune memory response. Thus, co-administration of inulin particles and an innate immune activator such as a PAMP together with a vaccine antigen, results in a surprisingly synergistic enhancement of the immune memory response against a co-administered vaccine antigen. The co-administration of inulin particles with an innate immune activator or PAMP also provided a surprising dose-sparing effect on the innate immune activator, such that the same adjuvant effect could be obtained with a reduced dose of the PAMP innate immune activator. Again this effect of inulin particles would not be predicted by the danger model of adjuvant action. This provides the opportunity to use inulin particles to achieve the same adaptive immune enhancement effect with a lower dose of the innate immune activator, thereby offering the opportunity to reduce dose-limiting side effects such as inflammation associated with innate immune activators including PAMPs. Co-administration of the inulin particles has further potential to reduce adverse inflammation-associated side effects of innate immune activators and PAMPs by blocking or attenuating inflammatory gene expression.

The applicants have found, therefore, that the combination of an inulin particle together with a PAMP innate immune activator results in a surprisingly favourable and synergistic immune response.

SUMMARY OF THE INVENTION

The present invention relates to products and methods for inducing a favourable anti-inflammatory and/or immune response. The invention is based on the surprising discovery that inulin particles can be used to provide, hitherto unknown, anti-inflammatory effects.

A further embodiment of the invention is based on the unexpected finding that the co-administration of inulin particles with an innate immune activator results in a favourable and synergistic modulation of the balance between innate and adaptive immune responses, such that an enhanced immune memory response is achieved to a co-administered antigen with, if anything, a reduction of inflammation-associated side effects.

Accordingly, in a first aspect, the present invention provides a composition comprising or consisting of inulin particles for use in the reduction or inhibition of inflammation, and/or for treating or preventing inflammatory disease, in a subject.

To put it another way, the first aspect of the present invention provides a method for the reduction or inhibition of inflammation, and/or for treating or preventing (including prophylaxis against) inflammatory disease, in a subject, the method comprising the administration of a therapeutically-effective amount of a composition comprising or consisting of inulin particles to the subject.

To put it yet another way, the first aspect of the present invention provides for the use of a composition comprising or consisting of inulin particles in the manufacture of a medicament for the reduction or inhibition of inflammation, and/or for treating or preventing inflammatory disease, in a subject.

In an embodiment of the first aspect of the present invention, the reduction or inhibition of inflammation, and/or the treatment or prevention of inflammatory disease, may be characterised by the up-regulation of the expression of one or more anti-inflammatory genes and/or proteins and/or for the down-regulation of the expression of one or more pro-inflammatory genes and/or proteins in the subject, or more optionally, specifically in the subject's myeloid or lymphoid cells including monocytes, dendritic cells, granulocytes, NK cells and/or lymphocytes. Exemplary pro-inflammatory genes for down-regulation in the subject in this context may include interleukin (IL)-1, IL1RAP, IL18RAP, IL6, cyclooxygenase (Cox)-2, FPR2, MYD88, NALP3, NLRP3, NLRP12, CARD12, IFIT1, IFIT2, IFIT3, IDO, CXCL5, CXCL6, CXCR7, CD14, TLR4, NOD2, formyl receptors 1,2 or 3, and members of CXCL chemokine family and/or TLR family members. Exemplary anti-inflammatory genes for upregulation in the subject in this context may include IL-1 receptor antagonist (IL-1RA), IL1RN, and IL1R2, IL18BP, CD5L, CD33, ATF3, TREM1, PPAR-gamma, FCRL2 and CD36.

Accordingly, inulin particles may be used in accordance with the first aspect of the present invention to reduce or inhibit inflammation in a subject. Inflammation in a subject may be caused, for example, by the exposure to one or more pro-inflammatory substances, including pathogenic infections (including bacterial, viral, fungal or protozoal infection, exemplary infections including pandemic or seasonal *influenza*, inhalational anthrax, gram negative septicaemia, systemic viraemia, encephalitis, Q fever, tuluraemia, small pox, chronic hepatitis B or C infection, SARS, pertussis, malaria, HIV, tuberculosis, polio, rabies, respiratory syncytial virus (RSV), shigella, mononucleosis, cytomegalovirus and toxic shock syndrome, allergenic substances, exemplary allergens being insect venom, cat or dog dander, rye grass, dust mite antigen, and pollens, or other pro-inflammatory substances or compositions, including, for example, compositions comprising pro-inflammatory substances, such as vaccine compositions or allergen-desensitisation compositions, or anti-cancer treatments. The inulin particles may be administered to the subject before, simultaneously with, or after the subject's exposure to the one or more pro-inflammatory substances.

An embodiment of particular interest in accordance with the first aspect of the present invention is the use of inulin particles to reduce or inhibit inflammation in a subject that is caused by exposure (such as the administration of) a pro-inflammatory substance or composition which contains a substance comprising or consisting of a innate immune activator and in particular a pathogen-associated molecular pattern (PAMP) including functional variants, derivatives or analogs thereof. The pro-inflammatory composition may, for example, be a pharmaceutically acceptable composition comprising a pro-inflammatory component that is intentionally administered to the subject, or in another example may be a pro-inflammatory substance (e.g. biological or pathogenic substance or organism) to which the subject is intentionally or accidentally exposed. In this context, administration of the inulin particles to the subject before, or simultaneously with (including as a single mixture with), administration of or exposure to the pro-inflammatory composition may be most beneficial. Thus, in this embodiment, the composition comprising inulin particles is used to reduce or inhibit the inflammatory response of the subject to the pro-inflammatory substance or composition.

Where the pro-inflammatory composition is an adjuvant composition that comprises or consists of PAMP then, for example, the inulin particles may be used to reduce, inhibit or prevent, one or more of a subject's adverse reactions to the PAMP, such as one or more adverse reactions including headache, fatigue, myalgia, diarrhoea, fever, inflammation and granuloma formation at the site of injection, pyrogenicity, nausea, adjuvant arthritis, uveitis, eosinophilia, allergy, anaphylaxis, organ specific toxicity or immunotoxicity, i.e. the liberation of toxic quantities of inflammatory cytokines.

Inulin particles may also be used in accordance with the first aspect of the present invention to treat or prevent inflammatory disease in a subject. Types of inflammatory diseases of particular interest for treatment or prevention in this context may include inflammatory diseases that are characterised by, or associated with NFkB activation and/or elevated IL-1 gene or protein levels or signalling, or IL-1 dysregulation. Exemplary inflammatory diseases include migraine, chronic fatigue syndrome, rheumatoid arthritis, asthma, chronic obstructive airways disease, inflammatory bowel disease including ulcerative colitis and Crohn's disease, chronic fatigue syndrome, cryopyrin-associated periodic syndromes including neonatal onset multisystem inflammatory disease and Muckle Wells syndrome, inflammasome-associated disorders, psoriasis, atherosclerosis, type 1 or type 2 diabetes mellitus, hereditary fever syndromes, tumour necrosis factor receptor-associated periodic syndrome, Schnitzler syndrome, systemic lupus erythematosis, autoimmune hepatitis, Behçet disease and idiopathic recurrent pericarditis.

Accordingly, subjects for treatment by the method of the first aspect of the present invention may include those who have been, will be (in the sense that they are scheduled to be, or are at increased risk of being, preferably within the following month, week, 6, 5, 4, 3, 2 or 1 days, or less than 24, 12, 6, 5, 4, 3, 2 or 1 hours), or are simultaneously being, exposed to one or more pro-inflammatory substances, including pathogenic infections (including bacterial, viral, fungal or protozoal infection), allergenic substances, or other pro-inflammatory compositions, including, for example, compositions comprising pro-inflammatory adjuvant, such as vaccine compositions or allergen-desensitisation compositions; and/or those suffering from or determined to be at risk of suffering from an inflammatory disease, including an inflammatory disease that is characterised by, or associated with, elevated IL-1 levels or signalling, or IL-1 dysregulation, and may be selected from the group consisting of migraine, chronic fatigue syndrome, rheumatoid arthritis, inflammatory bowel disease including ulcerative colitis and Crohn's disease, chronic fatigue syndrome, cryopyrin-associated periodic syndromes including neonatal onset multisystem inflammatory disease and Muckle Wells syndrome, inflammasome-associated disorders, psoriasis, atherosclerosis, type 2 diabetes, hereditary fever syndromes, tumour necrosis factor receptor-associated periodic syndrome, Schnitzler syndrome, Behçet disease and idiopathic recurrent pericarditis.

A second aspect of the present invention provides an immunological and/or pharmaceutically acceptable composition comprising:
(a) an anti-inflammatory component, such as inulin particles and/or one or more other anti-inflammatory inhibitors of IL-1 and/or one or more other anti-inflammatory inhibitors of NFκB activation;
(b) a substance comprising or consisting of one or more species of pathogen-associated molecular pattern (PAMP); and optionally, further comprising
(c) one or more additional substances, for example, as selected from the group consisting of an antibody, antisense oligonucleotide, protein, antigen, allergen, a polynucleotide molecule, recombinant viral vector, a whole microorganism, or a whole virus.

Pathogen-associated molecular patterns (PAMPs), as used in the context of the first and second aspects of the present invention, refers to molecules having the ability to activate the innate immune system. PAMPs are directly or indirectly recognised by one or more innate immune receptors, and/or activate inflammatory gene pathways in immune cells. PAMPs induce pro-inflammatory gene expression and protein production by immune cells including, for example, one or more of lymphocytes, monocytes, granulocytes, NK cells, dendritic cells, pro-inflammatory gene expression including, for example, one or more cytokines including TNF-α, G-CSF, GM-CSF, IL-1 through to IL-33 and more particularly IL-1, IL-4, IL-5, IL-6, IL-12, IL-13, IL-18, IL-20, interferons including type 1 interferons and gamma interferon, chemokines including the CXC family of chemokines including CXCL1 to CXCL17, CC family chemokines including CCL1 to CCL28, CX3C chemokines including fractalkine, C Family chemokines including XCL1 to XCL2, with induction of these pro-inflammatory genes typically involving activation of the NFκB transcription factor.

In the context of the present application, the term PAMP is intended to include not only those PAMPs found in nature, but also functionally equivalent mimetics, variants, derivatives and analogs thereof, including synthetic PAMPs. Numerous naturally-occurring and synthetic PAMPs are known in the art, many of which are discussed in more detail below.

Component (a) of the composition of the second aspect of the present invention is an anti-inflammatory component, such as an anti-inflammatory inhibitor of IL-1 or anti-inflammatory inhibitor of NFkB. In an embodiment of particular interest for the present invention the anti-inflammatory component is or comprises inulin particles. Other anti-inflammatory inhibitors of IL-1 of particular interest are functionally-equivalent to inulin particles, in the sense of possessing an essentially equivalent anti-inflammatory property, activity and/or specificity and/or possessing an essentially equivalent adjuvant property. These may include one or more of IL1 receptor antagonists, IL1RA, Anakinra, Rilonacept, IL-1R/L1RacP/Fc-fusion protein, Canakinumab, mass IL-1 blocking antibody, IL1 receptor blockers, IL-1RII, indomethacin, non-steroidal anti-inflammatory drugs (NSAID) including indomethacin, glucocorticoids, caspase inhibitors including caspase 1 inhibitors, inflammasome inhibitors, chloroquine, P2X7 receptor inhibitors, ST2 receptor inhibitors, curcumin, resveratrol, and eicosanoid biosynthesis inhibitors.

Component (b) of the composition of the second aspect of the present invention is a substance comprising or consisting of one or more pathogen-associated molecular pattern (PAMP). In one embodiment, the substance may comprise no greater than ten distinct molecular species of PAMP, such as nine or less, eight or less, seven or less, six or less, five or less, four or less, three or less, two or less, or only one distinct molecular species of PAMP. In one option, the limitation on the number of distinct molecular species of PAMP in component (b) may be applied only in respect of combination with inulin particles comprising or consisting of a specific type of inulin.

Thus, for example, in a particular embodiment, component (b) may comprise no greater than ten, nine, eight, seven, six, five, four three, two or one distinct molecular species of PAMP where the inulin particles in component (a) comprise or consist of gamma inulin.

In another particular embodiment, component (b) may comprise no greater than ten, nine, eight, seven, six, five, four three, two or one distinct molecular species of PAMP where the inulin particles in component (a) comprise or consist of delta inulin.

In another particular embodiment, component (b) may comprise no greater than ten, nine, eight, seven, six, five, four three, two or one distinct molecular species of PAMP where the inulin particles in component (a) comprise or consist of epsilon inulin.

Distinct molecular species of PAMP, in the context of the second aspect of the present invention, may for example be structurally distinct. Such a structural distinction may, for example, be determined by methods of structural analysis, which are known and routine in the art, such as mass spectroscopy, nuclear magnetic resonance, FTIR, circular dichroism, or differential scanning calorimetry.

Additionally, or alternatively, distinct molecular species of pathogen-associated molecular pattern (PAMP), in the context of the second aspect of the present invention, may be functionally distinct. Functionally distinct molecular species of PAMP may characterised by displaying a different binding profile to innate immune receptors. This may be assessed, for example, by measuring the binding of PAMP species to a panel of innate immune receptors which may, for example, comprise receptors selected from TLRs, such as human or animal TLR-1, TLR-2, TLR-3, TLR-4, TLR-5, TLR-6, TLR-7, TLR-8, TLR-9, murine TLR-11; NOD-1, NOD-2, other NOD-like receptors (NLRs) such as NLRP1, NLRP3, NLRP12, NLRC4; DECTIN-1; DC-SIGN; AIM-2; C-type Lectin, MD2; CD14; LBP; CD36; RIG-I-like receptors including RIG-I, MDA5, LGP2 and/or ASC. Binding of PAMP species to these receptors may be assessed by routine methods, such as surface plasmon resonance (Schasfoort, 2008). The skilled person will be able to determine appropriate conditions under which to assess binding, which should typically be selected to provide an assessment of binding specificity under moderate to highly stringent conditions. Additionally, or alternatively, as known by the skilled person, the property of a PAMP may be detected or quantified in an immune cell line such as the THP-1 or RAW cell line, by a functional assay, for example using an NFkB activation reporter assay such as the Thermo Scientific Pierce Luciferase Assay Kit (Hughes, 2012) or by measurement of inflammatory gene or protein activation in response to incubation of the cell line with the substance being tested for PAMP activity.

In one embodiment of the second aspect of the present invention, the totality of PAMP that is present in the component (b) of the composition (and, optionally, all of the PAMP in the composition, in the event that component (c) contains further PAMP) will not bind to more than 20, 19, 18, 17, 16, 15, 14, 13, 12, 11, 10, 9, 8, 7, 6, 5, 4, 3, 2 or 1 of the a receptors in the panel of innate immune receptors as described above, with a PAMP that does not bind more than 3, 2 or 1 of the receptors being of particular interest.

Although capable of indirectly activating the innate immune system, through lysis of the lysosome in phagocytosing cells, inflammasome activation, caspase activation, induction of immune cell death, and release of endogenous DNA, antigen-binding carrier materials with adjuvant properties such as alum (or other metal salts or precipitates such as magnesium, calcium or aluminium phosphates, sulfates, hydroxides or hydrates thereof) have not been shown themselves to bind a specific PAMP receptor, and do not mimic a molecular pattern expressed by a pathogen and as they thereby act in a different manner to molecularly defined PAMPs that bind specific innate immune receptors, they do not form part of the definition of PAMPs as used in this application.

It will be appreciated that optional component (c) of the composition of the second aspect of the present invention may, for example, include one or more additional substances selected from the group consisting of an antibody, antisense oligonucleotide, protein, antigen, allergen, a polynucleotide molecule, recombinant viral vector, a whole microorganism, or a whole virus, and so component (c) may contribute one or more additional PAMPs to the composition. For example, whole microorganisms, whole viruses, endotoxin and the like will contain high numbers (certainly greater than ten) of molecularly, structurally, physically and/or functionally distinct molecular species of PAMP. Thus, the total number of distinct molecular species of PAMPs in the composition of the second aspect of the present invention may be greater than ten. But that does not detract from the requirement, in one embodiment of the second aspect of the present invention, that component (b) of the composition will comprise no greater than ten or fewer distinct molecular species of PAMP. Typically, therefore, the substance(s) optionally present in component (c) will be molecularly, structurally and/or functionally different molecules to the molecules present in component (b).

The one or more PAMPs (preferably all PAMPs) present in component (b) of the composition of the second aspect of the present invention possess a weight average molecular weight of up to but no more than 200,000 KDa, such as up to but no more than 150,000 KDa, 100,000 KDa, 50,000 KDa, 40,000 KDa, 20,000 KDa, 10,000 KDa, 5,000 KDa, 2,000 KDa, 1,000 KDa, 500 KDa, 450 KDa, 400 KDa, 350 KDa, 300 KDa, 250 KDa, 200 KDa, 150 KDa, 100 KDa, 50 KDa, 40 KDa, 30 KDa, 20 KDa, 10 KDa, 9 KDa, 8 KDa, 7 KDa, 6 KDa, 5 KDa, 4 KDa, 3 KDa, 2 KDa, or 1 KDa or less.

The composition according to the second aspect of the present invention may be a pharmaceutically acceptable composition. In this context, a pharmaceutically acceptable composition may be a composition that is safe for administration to a subject, such as a human subject, by injection, such as intravenous, subcutaneous or intramuscular injection. In one embodiment, the composition may be defined as being safe if it contains no, or substantially no, endotoxin.

Endotoxin is often used synonymously with the term lipopolysaccharide, which is a major constituent of the outer cell wall of Gram-negative bacteria. It consists of a polysaccharide (sugar) chain and a lipid moiety, known as lipid A, which is responsible for the toxic effects observed with endotoxin. The polysaccharide chain is highly variable among different bacteria and determines the serotype of the endotoxin and the lipid components are also highly variable such that a single endotoxin sample may contain 10's to 100's of distinct molecular species. Endotoxin is approximately 10 kDa in size but can form large aggregates up to 1000 kDa. Endotoxin is typically harmful and pyrogenic in therapeutic compositions and regulatory authorities have imposed strict limitations on the allowable levels of endotoxin within a pharmaceutical composition. Accordingly, the level of endotoxin in a composition according to the second aspect of the present invention should be minimised and may be less than 100 endotoxin units (EU) per dose, such as less than 90, 80, 70, 60, 50 40, 30, 20, 10, 5, 4, 3, 2, 1 or less EU per dose. The concentration of endotoxin in a composition according to the second aspect of the present invention may be less than 200 EU/m$^3$, such as less than 150, 100, 90, 80, 70, 60, 50 40, 30, 20, 10, 5, 4, 3, 2, 1 or less EU/m$^3$. In some embodiments, these limitations may be applied to the composition of the second aspect of the invention where the inulin particles present in component (a) comprise or consist of just one or two of gamma inulin, delta inulin or epsilon inulin. Methods for measuring endotoxin levels, such as the limulus amoebocyte assay (LAL) method, are well known in the art.

The composition of the second aspect of the present invention may optionally be packaged and/or presented in a convenient or unit dosage form.

The amount and/or concentration of PAMP present in component (b) of the composition of the second aspect of the present invention (and, optionally, the amount and/or concentration of PAMP present in the entire composition) is preferably less than the amount of PAMP that is required in an equivalent composition that differs only in that it does not include the inulin particles (or other equivalent anti-inflammatory component). In other words, the presence of inulin particles (or other equivalent anti-inflammatory component) in component (a) of the composition of the second aspect of the present invention provides a composition that is able to induce or modulate an immune response in a subject using less PAMP in component (b) than would be required to achieve the same level or type of induction or modulation compared to an equivalent composition that differs only in that it does not include the inulin particles (or other equivalent anti-inflammatory component).

Accordingly, the amount or concentration of the one or more PAMPs in component (b) of the composition of the second aspect of the present invention (and, optionally, the amount and/or concentration of the one or more PAMPs present in the entire composition) may be less than, such as less than 90%, 80%, 70%, 60%, 50%, 40%, 30%, 20%, 10%, 5%, 4%, 3%, 2%, 1%, 0.5%, 0.4%, 0.3%, 0.2%, 0.1%, 0.05%, 0.04%, 0.02%, 0.01% or less (by weight) than the optimal amount of the same one or more PAMPs that is required in an equivalent composition that differs only in that it does not include the inulin particles (or other equivalent anti-inflammatory component). The optimal amount of PAMPs in the equivalent composition is the amount that is required to achieve the desired effect of induction or modulation of an immune response including for example adjuvant enhancement of an immune response to a co-administered antigen without being so high as to cause unacceptable levels of inflammatory and/or other side-effects. As known in the art this can be determined empirically for each PAMP using routine methods, for example by performing dose-ranging toxicity studies in animal models, or by use of surrogate measures such as the extent of NFkB activation in cell-based functional assays. Indeed, such an equivalent composition may be entirely incapable of achieving the same level or type of induction or modulation, no matter how much PAMP is included, in the absence of inulin particles. In some embodiments, these limitations may be applied to the composition of the second aspect of the invention where the inulin particles present in component (a) comprise or consist of just one or two of gamma inulin, delta inulin or epsilon inulin.

A suitable or optimal ratio of inulin particles (or other equivalent anti-inflammatory component) in component (a) to PAMP in component (b) of the composition of the second aspect of the present invention, in order to achieve a desired effect, can be determined empirically by the skilled person for each specific combination of inulin particles and PAMP using routine methods. Typically, however, the weight/weight ratio of inulin particles (or other equivalent anti-inflammatory component) to PAMP may be in the range of from 10,000:1 to 1:1, from 1000:1 to 1:1, from 100:1 to 1:1, or from 100:1 to 10:1.

Accordingly, an immunological composition according to the second aspect of the present invention may include an effective amount for inducing a desired immune response of a combination of components, wherein the combination includes at least one inulin particle (or other equivalent anti-inflammatory component) and at least one PAMP innate immune activator. The PAMP innate immune activator in the immunological composition may be of any type of PAMP innate immune activator known in the art. For example, the PAMP innate immune activator may be selected from any of the group of substances that are known agonists of innate immune receptors. Accordingly, a PAMP innate immune activator for use in the present invention may bind and be an agonist of any one or more innate immune receptors of, TLRs, RNA hellcases, NOD1, NOD2, other NOD-like receptors (NLRs) such as NLRP1, NLRP3, NLRP12, NLRC4; DECTIN-1; DC-SIGN; AIM-2; C-type Lectin, MD2; CD14; LBP; RIG-I-like receptors including RIG-I, MDA5, LGP2 and/or ASC, C-type lectin receptors, complement receptors, Fc receptors, and scavenger receptors.

A third aspect of the present invention provides a kit of parts comprising: (a) a first container that contains a composition comprising or consisting of an anti-inflammatory component, such particles of inulin and/or one or more other anti-inflammatory inhibitors of IL-1 or NFkB (as discussed above in respect of the second aspect of the present invention); and (b) a second container that contains a substance comprising or consisting of a PAMP.

The disclosure above of certain embodiments relating to the identity, type, amounts, concentrations and the like of various component in the composition of the second aspect of the present invention may be applied mutatis mutandis to the definition of the compositions and substances presented with the first and second containers of the kit of the third aspect of the present invention.

Thus, in one embodiment of the third aspect of the present invention, the substance present in the second container may comprise no greater than ten distinct molecular species of PAMP, such as nine or less, eight or less, seven or less, six or less, five or less, four or less, three or less, two or less, or only one distinct molecular species of PAMP. In one option, the limitation on the number of distinct molecular species of PAMP in the substance present in the second container may be applied only in respect of kits in which the first container contains a composition comprising or consisting of particles of a specific type of inulin, such as only gamma inulin, only delta inulin or only epsilon inulin.

In another embodiment of the third aspect of the present invention, the totality of PAMP that is present in the second container may not bind to more than 20, 19, 18, 17, 16, 15, 14, 13, 12, 11, 10, 9, 8, 7, 6, 5, 4, 3, 2 or 1 of the receptors in the panel of innate immune receptors as described above.

Either or both of the first container and/or second container in the kit of the third aspect of the present invention may optionally further comprise one or more additional substances, for example, as selected from the group consisting of an antibody, antisense oligonucleotide, protein, antigen, allergen, a polynucleotide molecule, recombinant viral vector, a whole microorganism, or a whole virus.

The one or more PAMPs (preferably all PAMPs) present in the second container of the kit of the third aspect of the present invention may possess a weight average molecular weight of up to but no more than 200,000 KDa, such up to but no more than 150,000 KDa, 100,000 KDa, 50,000 KDa, 40,000 KDa, 20,000 KDa, 10,000 KDa, 5,000 KDa, 2,000 KDa, 1,000 KDa, 500 KDa, 450 KDa, 400 KDa, 350 KDa, 300 KDa, 250 KDa, 200 KDa, 150 KDa, 100 KDa, 50 KDa, 40 KDa, 30 KDa, 20 KDa, 10 KDa, 9 KDa, 8 KDa, 7 KDa, 6 KDa, 5 KDa, 4 KDa, 3 KDa, 2 KDa, 1 KDa or less.

Either or both of the first container and/or second container in the kit of the third aspect of the present invention may contain a unit dose of the material contained therein.

Either or both of the first container and/or second container in the kit of the third aspect of the present invention will typically be pharmaceutically acceptable compositions, as defined above. Accordingly, the level of endotoxin in either or both of the first container and/or second container in the kit may be less than 100 EU per dose, such as less than 90, 80, 70, 60, 50 40, 30, 20, 10, 5, 4, 3, 2, 1 or less EU per dose. The concentration of endotoxin in either or both of the first container and/or second container in the kit may be less than 200 EU/m$^3$, such as less than 150, 100, 90, 80, 70, 60, 50 40, 30, 20, 10, 5, 4, 3, 2, 1 or less EU/m$^3$. In some embodiments, these limitations may be applied to the kit of the third aspect of the invention where inulin particles present in the first container comprise or consist of just one or two of gamma inulin, delta inulin or epsilon inulin.

The amount and/or concentration of PAMP present in the second container of the kit of the third aspect of the present invention is preferably less than the optimal amount, such as less than 90%, 80%, 70%, 60%, 50%, 40%, 30%, 20%, 10%, 5%, 4%, 3%, 2%, 1%, 0.5%, 0.4%, 0.3%, 0.2%, 0.1%, 0.05%, 0.04%, 0.02%, 0.01% or less (by weight), of PAMP that is required, when used alone to achieve the desired level or type of induction or modulation of the immune response.

In one embodiment of the third aspect of the present invention, the weight/weight ratio of inulin particles (or other equivalent anti-inflammatory component) in the first container to PAMP in the second container may be in the range of from 10000:1 to 1:1, from 1000:1 to 1:1, from 100:1 to 1:1, or from 100:1 to 10:1.

In a further embodiment of any of the first, second or third aspects of the present invention, the substance comprising or consisting of a PAMP may be an innate immune activator, and comprise or consist of one or more a substances selected from the group that binds and is an agonist of one or more of a TLR, RNA helicase, NOD1, NOD2, other NOD-like receptors (NLRs) such as NLRP1, NLRP3, NLRP12, NLRC4; DECTIN-1; DC-SIGN; AIM-2; C-type Lectin, MD2; CD14; LBP; RIG-I-like receptors including RIG-F, MDA5, LGP2 and/or ASC, C-type lectin receptor, complement receptor, Fc receptor, and scavenger receptor.

In a further embodiment of any of the first, second or third aspects of the present invention, the or each PAMP may be a substance that is selected from the group consisting of diacyl lipopeptide, triacyl lipopeptide, Pam3CSK4, lipoteichoic acid, peptidoglycan, HSP70, zymosan, ssRNA, dsRNA, dsDNA, poly(I:C), poly(I:C-LC), Hiltonol™, PolyI:PolyC12-U, Ampligen™, MPLA, heat shock protein, fibrinogen, heparan sulfate fragments, hyaluronic acid fragments, synthetic TLR4 agonist, imidazoquinoline, gardiquimod, loxoribine, bropirimine, CL264, R848, CL075 PolyU, imiquimod, resiquimod, ssPolyU/LyoVec, ssRNA40/LyoVec, unmethylated CpG oligonucleotide, Class B ODN, Class C ODN, CpG2006 (SEQ ID NO:1), CpG1828 (SEQ ID NO:2), CpG7909 (SEQ ID NO:3), C12-iE-DAP, iE-DAP, Tri-DAP, muramyl dipeptide (MDP), L18-MDP, M-TriDAP, murabutide, PGN-ECndi, PGN-ECndss, PGN-Sandi, porin, lipoarabinomannan, phospholipomannan, glucuronoxylomannan, glycosylphosphatidylinositol (GPI)-anchored protein, hemozoin, viral dsDNA, synthetic dsDNA, viral dsRNA, synthetic dsRNA peptidoglycan containing the muramyl dipeptide NAG-NAM-gamma-D-glutamyl-meso diaminopimelic acid, peptidoglycan containing the muramyl dipeptide NAG-NAM-L-alanyl-isoglutamine, N-formyl methionine, muramyl tripeptide, beta-1,3-glucan, zymosan, cord factor, trehalose-6,6-dibehenate, Poly(dA:dT), Poly(dG:dC), 5'ppp-dsRNA, low density lipoprotein (LDL), oxidised LDL, chemically modified LDL, hemozoin, ATP.

In a further embodiment of any of the first, second or third aspects of the present invention, the inulin particle may comprises or consists of inulin which is selected from one or more of gamma inulin, delta inulin and epsilon inulin, or combinations of any one or more of these inulins with aluminium phosphate or aluminium hydroxide, including phosgammulin, phosdeltin, phosepsilin, algammulin, and algammulin, aldeltin, alepsilin such as are obtainable by methods as further described herein. Alpha and/or beta inulin or other modified inulin particles may also be used in addition to, or instead of, gamma, delta or epsilon inulin, providing they are in a suitable particulate form.

In a further embodiment of the composition used in the first aspect, the composition of the second aspect and/or the first and/or second containers of kit of the third aspect, wherein the composition comprising or consisting of inulin particles is a composition that comprises or consists of particles of at least two inulin preparations, then the preparations may differ in the polymorphic form of the inulin present and/or the presence or species of an antigen-binding carrier material. For example— the inulin particles may comprise gamma inulin (and/or a combination of gamma inulin with aluminium phosphate or aluminium hydroxide) mixed with delta inulin; alternatively the inulin particles may comprise gamma inulin (and/or a combination of gamma inulin with aluminium phosphate or aluminium hydroxide) mixed with epsilon inulin; alternatively the inulin particles may comprise delta inulin (and/or a combination of delta inulin with aluminium phosphate or aluminium hydroxide) mixed with gamma inulin; alternatively the inulin particles may comprise delta inulin (and/or a combination of delta inulin with aluminium phosphate or aluminium hydroxide) mixed with epsilon inulin; alternatively the inulin particles may comprise epsilon inulin (and/or a combination of epsilon inulin with aluminium phosphate or aluminium hydroxide) mixed with gamma inulin; alternatively the inulin particles may comprise epsilon inulin (and/or a combination of delta inulin with aluminium phosphate or aluminium hydroxide) mixed with delta inulin.

In the forgoing list, any recitation of gamma, delta and/or epsilon inulin may optionally also be replaced with alpha inulin and/or beta inulin.

In a further embodiment of any of the first, second or third aspects of the present invention, the composition used in the first aspect, the composition of the second aspect and/or the first and/or second containers of kit of the third aspect, may further comprise one or more additional substances, for example, as selected from the group consisting of an antibody, antisense oligonucleotide, protein, antigen, allergen, a polynucleotide molecule, recombinant viral vector, a whole microorganism, or a whole virus.

Accordingly, in a further embodiment of any of the first, second or third aspects of the present invention, the composition used in the first aspect, the composition of the second aspect and/or the first and/or second containers of kit of the third aspect, may further comprise one or more antigens. The or each antigen may be any type of antigen known in the art and may be selected from the group consisting of proteins, glycoproteins, peptides, polypeptides, cells, cell extracts, polysaccharides, polysaccharide conjugates, lipids, glycolipids, nucleic acids and carbohydrates, or conjugates of carbohydrates or lipids with protein, polypeptide/peptide antigens, peptide mimics of polysaccharides, or antigens may also be encoded within nucleic acid sequences. Antigens may be given in a crude, purified or recombinant form. Antigens may be derived from an infectious pathogen such as a virus, bacterium, fungus or parasite, or the antigen may be derived from a tumour antigen, an allergen, or self-protein.

Where one or more antigens, in particular one or more vaccine antigens is/are included in a further embodiment of any of the first, second or third aspects of the present invention, then it may also be suitable to further include one or more antigen-binding agents in the same mixture as the or each antigen.

Also provided by the second and third aspects of the present invention are methods for the preparation of the composition of the second aspect or of the kit of the third aspect.

The method may comprise the step of providing the component parts and then bringing them together to form a composition of the second aspect or the kit of the third aspect.

The present invention also provides a method for stimulating or modulating an immune response, including an antigen-specific immune response, in a subject by administering to the subject a therapeutically effective amount of the immunological composition of the second aspect or using a kit according to the third aspect. The method includes the steps of administering to the subject the immunological composition of the second aspect or the components of the kit of the third aspect, wherein the composition, or each component, is administered in an effective amount and at an effective time and route for inducing a desired immune response or effect.

Accordingly, a fourth aspect of the present invention provides a method for inducing or modulating an immune response in a subject, wherein said method comprises administering to the subject a therapeutically effective amount of the composition according to the second aspect of the invention, or simultaneously, sequentially or separately administering therapeutically effective amounts of the contents of the first and second containers of the kit of the third aspect of the present invention.

To put it another way, the fourth aspect of the present invention provides a composition according to the second aspect of the invention, or a kit according to the third aspect of the invention, for use in inducing or modulating an immune response in a subject.

To put it yet another way, the fourth aspect of the present invention provides for the use of a composition according to the second aspect of the invention and/or the use a kit according to the third aspect of the invention, in the manufacture of a medicament for inducing or modulating an immune response in a subject.

In one embodiment of the fourth aspect of the present invention, the modulation of the immune response may comprise increasing the speed of development of the immune response, compared to the speed of development of the immune response obtained in the subject with an equivalent composition that differs only in that it does not include the inulin particles. The immune response in question may, for example, be an adaptive immune response to one or more antigens. The adaptive immune response may comprise a response from one or more of T-cells (including one or more of CD4+ and/or CD8+ T-cells) and/or B-cells, and may for example be determined with respect to the production of one or more types or subtypes of antibodies, such as any one or more of IgA, IgE, IgG1, IgG2a, IgG2b, IgG3, IgG4 or IgM or with respect to the production of one or more types of cytokines, such as any one or more of IFN-γ, TGF-β, GM-CSF, TNFα, IL-1, IL-2, IL4, IL-5, IL-8, IL7, IL-8, IL10, IL12, IL13, IL-17, IL-20.

In another embodiment of the fourth aspect of the present invention, the modulation of the immune response may comprise increasing the specificity of the subject's immune response, compared to the specificity of the immune response obtained in the subject with an equivalent composition that differs only in that it does not include the inulin particles. The immune response in question may, for example, be an adaptive immune response. The adaptive immune response may comprise a response from one or more of T-cells (including one or more of CD4+ and/or CD8+ T-cells) and/or B-cells, and may for example be determined with respect to the production of one or more types or subtypes of antibodies, such as any one or more of IgA, IgE, IgG1, IgG2, IgG3, IgG4 or IgM. Increased specificity may, for example, include increasing the level of specificity of the B- and/or T-cell response to any antigen that is presented in the administered composition(s).

In another embodiment of the fourth aspect of the present invention, the modulation of the immune response may comprise increasing the magnitude of the subject's immune response, compared to the magnitude of the immune response obtained in the subject with an equivalent composition that differs only in that it does not include the inulin particles. The immune response in question may, for example, be an adaptive immune response. The adaptive immune response may comprise a response from one or more of T-cells (including one or more of CD4+ and/or CD8+ T-cells) and/or B-cells, and may for example be determined with respect to the production of one or more types or subtypes of antibodies, such as any one or more of IgA, IgE, IgG1, IgG2, IgG3, IgG4, IgM.

In another embodiment of the fourth aspect of the present invention, the modulation of the immune response may comprise increasing the duration of the subject's immune response, compared to the duration of the immune response obtained in the subject with an equivalent composition that differs only in that it does not include the inulin particles. The immune response in question may, for example, be an adaptive immune response. The adaptive immune response may comprise a response from one or more of T-cells (including one or more of CD4+ and/or CD8+ T-cells) and/or B-cells, and may for example be determined with respect to the production of one or more types or subtypes of antibodies, such as any one or more of IgA, IgE, IgG1, IgG2, IgG3, IgG4, IgM.

In another embodiment of the fourth aspect of the present invention, the modulation of the immune response may comprise, modifying the type of the subject's immune response, compared to the type of the immune response obtained in the subject with an equivalent composition that differs only in that it does not include the inulin particles. The type of immune response in question may, for example, be an adaptive immune response. The type of adaptive immune response may be characterised by the speed, magnitude, specificity, and/or duration of one or more aspects of an adaptive immune response relative to other aspects of the adaptive response, including for example, the response from one or more of T-cells (including one or more of CD4+ and/or CD8+ T-cells; Th1, Th2, Th17 and Treg cells) and/or B-cells, and may for example be determined with respect to the production of one or more types or subtypes of antibodies compared to one or more other subtypes, such as any one or more of IgA, IgE, IgG1, IgG2, IgG3, IgG4 or IgM compared to any one or more of the others.

More specific examples of modifying the type of the subject's immune response, in accordance with the fourth aspect of the present invention include modifying the balance between the innate and adaptive immune response; enhancing the immune memory response; altering the type of immune response such as by enhancing or inhibiting the Th1, Th2, Th17 or Treg response compared to the other responses; suppressing the IgE response; or enhancing one or more of the IgA, IgM or IgG subtype responses. To put it another way, the fourth aspect of the present invention provides a method to obtain an optimal immune subclass or subtype response, including the optimal T- or B-cell response to a vaccine antigen, where it could not be achieved to the same extent, using an equivalent composition or kit that differs only in that it does not include the inulin particles (or other equivalent anti-inflammatory component).

A fifth aspect of the present invention provides a method for inducing or modulating an immune response to an antigen, wherein said method comprises—
(a) administering to a subject a therapeutically effective amount of a composition according to the second aspect of the present invention, wherein said composition also comprises the antigen and, optionally, further comprises antigen-binding carrier material; or
(b) simultaneously, sequentially or separately administering to a subject therapeutically effective amounts of the contents of the first and second containers of the kit of the third aspect of the present invention, wherein said contents of the first and/or second containers of the kit also comprises the antigen and, optionally, further comprises antigen-binding carrier material.

To put it another way, the fifth aspect of the present invention provides a composition according to the second aspect of the present invention, wherein said composition also comprises an antigen and, optionally, further comprises antigen-binding carrier material, for use in modulating an immune response to the antigen; and also provides for a kit of the third aspect of the present invention, wherein the contents of the first and/or second containers of the kit also comprises an antigen and, optionally, further comprises antigen-binding carrier material, for use in inducing or modulating an immune response to the antigen.

To put it in yet another way, the fifth aspect of the present invention provides for the use of a composition according to the second aspect of the present invention, wherein said composition also comprises an antigen and, optionally, further comprises antigen-binding carrier material, in the manufacture of a medicament for inducing or modulating an immune response to the antigen; and also provides for the use of a kit of the third aspect of the present invention, wherein the contents of the first and/or second containers of the kit also comprises an antigen and, optionally, further comprises antigen-binding carrier material, for the manufacture of a medicament for inducing or modulating an immune response to the antigen.

A sixth aspect of the present invention provides a method for the vaccination of a subject, wherein said method comprises—
  (a) administering to a subject a therapeutically effective amount of a composition according to the second aspect of the present invention, wherein said composition also comprises an antigen and, optionally, further comprises antigen-binding carrier material; or
  (b) simultaneously, sequentially or separately administering to a subject therapeutically effective amounts of the contents of the first and second containers of the kit of the third aspect of the present invention, wherein said contents of the first and/or second containers of the kit also comprises an antigen and, optionally, further comprises antigen-binding carrier material.

To put it another way, the sixth aspect of the present invention provides a composition according to the second aspect of the present invention, wherein said composition also comprises an antigen and, optionally, further comprises antigen-binding carrier material, for use in the vaccination of a subject; and also provides for a kit of the third aspect of the present invention, wherein the contents of the first and/or second containers of the kit also comprises an antigen and, optionally, further comprises antigen-binding carrier material, for use in the vaccination of a subject.

To put it in yet another way, the sixth aspect of the present invention provides for the use of a composition according to the second aspect of the present invention, wherein said composition also comprises an antigen and, optionally, further comprises antigen-binding carrier material, in the manufacture of a medicament for the vaccination of a subject; and also provides for the use of a kit of the third aspect of the present invention, wherein the contents of the first and/or second containers of the kit also comprises an antigen and, optionally, further comprises antigen-binding carrier material, for the manufacture of a medicament for the vaccination of a subject.

Suitable vaccine antigens for use in the fifth and/or sixth aspects of the present invention may include those described elsewhere in this application, including those described above in respect of the first, second and third aspects of the present invention.

The amount and/or concentration of antigen used in the fifth and sixth aspects of the present invention may be less than the amount of antigen that is required in an equivalent composition and/or kit that differs only in that the composition or kit does not include inulin particles (or other equivalent anti-inflammatory component). In other words, the presence of inulin particles (or other equivalent anti-inflammatory component) in the compositions and/or kits may provide for methods and uses that can induce or modulate an immune response in accordance with the fifth aspect, or vaccinate a subject in accordance with the sixth aspect, with less antigen.

Accordingly, the amount or concentration of one or more antigens in the compositions and/or kits used in the fifth and/or sixth aspects of the present invention may be less, such as less than 90%, 80%, 70%, 60%, 50%, 40%, 30%, 20%, 10%, 5%, 4%, 3%, 2%, 1%, 0.5%, 0.4%, 0.3%, 0.2%, 0.1%, 0.05%, 0.04%, 0.02%, 0.01% or less (by weight) than the optimal amount of the same one or more antigens that is/are required to achieve a corresponding desired immune response, or effective vaccination of a subject, in an equivalent composition or kit that differs only in that it does not include the inulin particles (or other equivalent anti-inflammatory component).

The optimal amount in the equivalent composition is the amount that is required to achieve the desired effect of induction or modulation of an immune response without being so high as to cause unacceptable levels of inflammatory and/or other side-effects. This can be determined empirically by the skilled person for each antigen and PAMP using routine methods. Indeed, such an equivalent composition may be entirely incapable of achieving the same level or type of immune induction or modulation, or vaccination, no matter how much antigen is included. In the absence of inulin particles (or other equivalent anti-inflammatory component).

The present invention also provides a method of downmodulating an existing unwanted immune response in a subject, such as an allergy to an allergen, or a chronic inflammatory condition, for example by downregulation of allergen-specific IgE or induction of blocking allergen-specific IgG. The method includes the steps of administering to the subject the composition of the second aspect, or the components of the kit of the third aspect, and optionally a further component such as an antigen or allergen wherein each component is administered in an effective amount and at an so effective time and route for inhibiting or downmodulating the unwanted immune response and/or inducing a favourable counter-regulatory immune response.

Accordingly, a seventh aspect of the present invention provides a method for the allergen desensitisation of a subject, wherein said method comprises—
  (a) administering to a subject a therapeutically effective amount of a composition according to the second aspect of the present invention, wherein said composition also comprises an allergen and, optionally, further comprises allergen-binding carrier material; or
  (b) simultaneously, sequentially or separately administering to a subject therapeutically effective amounts of the contents of the first and second containers of the kit of the third aspect of the present invention, wherein said contents of the first and/or second containers of the kit also comprises an allergen and, optionally, further comprises an allergen-binding carrier material.

To put it another way, the seventh aspect of the present invention provides a composition according to the second aspect of the present invention, wherein said composition also comprises an allergen and, optionally, further comprises allergen-binding carrier material, for use in the allergen desensitisation of a subject; and also provides for a kit of the third aspect of the present invention, wherein the contents of the first and/or second containers of the kit also comprises an allergen and, optionally, further comprises allergen-binding carrier material, for use in the allergen desensitisation of a subject.

To put it in yet another way, the seventh aspect of the present invention provides for the use of composition according to the second aspect of the present invention, wherein said composition also comprises an allergen and, optionally, further comprises allergen-binding carrier material, in the manufacture of a medicament for the allergen desensitisation of a subject; and also provides for the use of a kit of the third aspect of the present invention, wherein the contents of the first and/or second containers of the kit also comprises an allergen and, optionally, further comprises allergen-binding carrier material, for the manufacture of a medicament for the allergen desensitisation of a subject.

An eighth aspect of the present invention provides a method for the treatment of cancer, wherein said method comprises administering to a subject a therapeutically effective amount of a composition according to the second aspect of the claims; or simultaneously, sequentially or separately administering to a subject therapeutically effective amounts of the contents of the first and second containers of the kit of the third aspect of the present invention.

To put it another way, the eighth aspect of the present invention provides a composition according to the second aspect of the present invention or a kit of the third aspect of the present invention, for use in the treatment of cancer.

To put it in yet another way, the eighth aspect of the present invention provides for the use of a composition according to the second aspect of the present invention or a kit of the third aspect of the present invention in the manufacture of a medicament for the treatment of cancer.

In one embodiment of the eighth aspect of the present invention, the composition according to the second aspect of the present invention as used therein further comprises a cancer antigen.

In another embodiment of the eighth aspect of the present invention, the contents of the first and/or second containers of the kit according to the third aspect of the present invention as used therein further comprises a cancer antigen.

A ninth aspect of the present invention provides a method for the manufacture of a vaccine, the method comprising the step of combining an antigen, and optionally also an antigen-binding carrier material, with components (a) and (b) of the composition according to the second aspect of the present invention, thereby to produce a vaccine composition.

Accordingly, the ninth aspect of the present invention also provides for the use of the composition of the second aspect of the present invention, as an adjuvant in a vaccine.

It is noted that, in the following examples, we demonstrate that compositions according to the present invention are able to provide single vaccine dose protection against otherwise lethal infection. We have also found that compositions of the present invention, when formulated as a vaccine against *influenza*, can provide effective single dose protection in a murine model. Single dose vaccine protection is extremely desirable and, hitherto, hard to achieve in the field of vaccinology. Yet compositions of the present application have been found to provide single dose vaccine protection.

Accordingly, in another embodiment of the ninth aspect of the present invention, a single-dose vaccine composition is provided comprising or consisting of inulin particles (optionally in the form of a composition according to the second aspect of the invention or a kit of the third aspect), an antigen and, optionally, an antigen-binding carrier material. Such a single dose vaccine composition is effective to provide vaccine protection in the subject with only a single administration of a dose of the vaccine.

Also provided is a method of vaccinating a subject the method comprising or consisting of administering to the subject a single-dose of the vaccine. Although the method may comprise one or more other steps, it comprises no additional steps of administering the vaccine after the initial administration.

Accordingly, to put it another way, the present invention also provides for a single-dose of the vaccine as defined above for use in vaccinating a subject by a method comprising or consisting of administering to the subject a single-dose of the vaccine.

To put it yet another way, the present invention also provides for the use of a single-dose of the vaccine as defined above for the manufacture of a medicament for use in vaccinating a subject by a method comprising or consisting of administering to the subject a single-dose of the vaccine.

A further advantageous feature of the present invention is that its compositions, substances, kits and methods according to the other aspects of the present invention are particularly effective in treating those subject groups that may typically fail to respond at all, or adequately, to conventional adjuvant and vaccine compositions. Such subject groups may include the young, the older population and pregnant women. In one embodiment, *influenza* vaccines of the present invention may be of particular interest for administration to such subjects.

Accordingly, the subject to be treated by the compositions, substances, kits and methods according to the other aspects of the present invention may be child, for example a male or female child. The child may, for example, by less than 18 years old, 17 years old, 16 years old, 15 years old, 14 years old, 13 years old, 12 years old, 11 years old, 10 years old, 9 years old, 8 years old, 7 years old, 6 years old, 5 years old, 4 years old, 3 years old, 2 years old, 1 year old, 11 months old, 10 months old, 9 months old, 8 months old, 7 months old, 6 months old, 5 months old, 4 months old, 3 months old, 2 months old, or 1 month old, relative to the date of their birth.

Alternatively, the subject to be treated by the compositions, substances, kits and methods according to the other aspects of the present invention may be an older human, for example a male or female. The older human may be at least 40 years old, at least 45 years old, at least 50 years old, at least 55 years old, at least 80 years old, at least 65 years old, at least 70 years old, at least 75 years old, at least 80 years old, at least 85 years old, or at least 90 years old.

Alternatively, the subject to be treated by the compositions, substances, kits and methods according to the other aspects of the present invention may be a pregnant female. The female may be up to, or at least, 5, 10, 15, 20, 25, 30, 35 or 40 weeks pregnant.

A tenth aspect of the present invention provides a method for the identification of the optimal concentrations and ratio of components (a) and (b) of the composition according to the second aspect of the present invention, the method comprising the optional step of combining an antigen, and optionally also an antigen-binding carrier material, with components (a) and (b) of the composition according to the second aspect of the present invention, administering the combined composition in a range of different doses to a series of subjects and then measuring the resulting immune response and optionally challenging the subject with a live pathogen thereby allowing the optimal composition to be identified.

In another embodiment of the tenth aspect of the present invention, the contents of the first and/or second containers of the kit according to the third aspect of the present invention form, and optionally an antigen, form an assay kit for identification of the optimal composition for a desired immune application.

In another embodiment of the tenth aspect of the present invention, a method for the manufacture of an assay kit is provided, the method comprising the step of combining an antigen, and optionally also an antigen-binding carrier material, with components (a) and (b) of the composition according to the second aspect of the present invention, thereby to produce a vaccine assay kit.

These and other aspects and embodiments of the invention will be described in greater detail herein.

BRIEF DESCRIPTION OF THE ACCOMPANYING FIGURES

Figure 2:
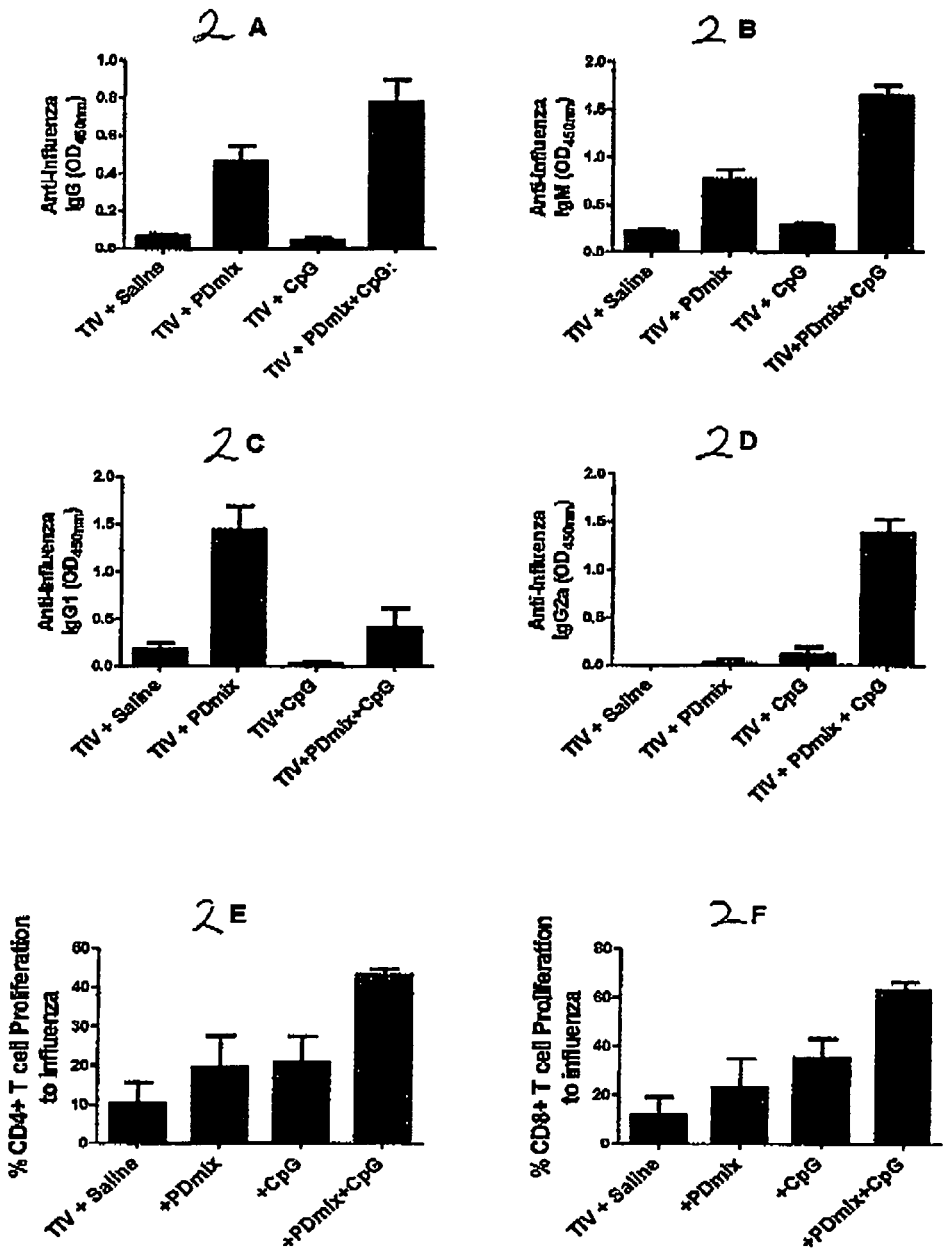

FIG. 1 shows four graphs labeled A-D showing the immunogenicity in mice of trivalent influenza vaccine (TIV) formulated with the TLR9 agonist PAMP CpG2006 (SEQ ID NO:1), highlighting the synergistic effect when inulin particles are added to the CpG-containing TIV vaccine formulation. Female Balb/c mice at 6-8 weeks of age (n=5-8 per group) were immunised Intramuscularly twice 14 days apart, with 50 ul of a commercial human TIV at 100 ng HA per dose, combined with either 2, 7, 20 or 60 μg of CpG2006 (SEQ ID NO:1) alone or mixed with 1 mg PDmix(1:5). FIG. 1A shows serum anti-influenza total IgG levels, FIG. 1B shows serum anti-influenza IgM levels, FIG. 1C shows serum anti-influenza IgG1 levels and FIG. 1D shows serum anti-influenza IgG2a levels 42 days after the second immunization as measured by ELISA. Shown are group mean OD+SD, FIG. 2 shows six graphs labeled A-F demonstrating the synergistic effects of a combination of the TLR9 agonist PAMP (CpG1668) and Munn particles (PDmix1:36) on the immune response of neonatal mice to TIV vaccine. Neonatal BALB/c mice (n=5-7/group) were immunized Lm. with TIV (100 ng total HA protein) at 14 days and 23 days of age. Sera were collected 14 days after the last Injection for measurement of antibodies by ELISA. Groups received either TIV alone or formulated with PDmix1:36 (1 mg), CpG1668 (20 ug), or PDmix (1 mg)+CpG1668 (20 ug). FIG. 2A shows the group receiving TIV+PDmix+CpG (final column in each Fig.) had significantly higher anti-influenza total IgG, FIG. 2B shows higher IgM, FIG. 2C shows lower IgG1, FIG. 2D shows higher IgG2a, FIG. 2E shows higher anti-Influenza CD4+T cell and FIG. 2F shows higher CD8+T-cell memory responses.

Figure 3:
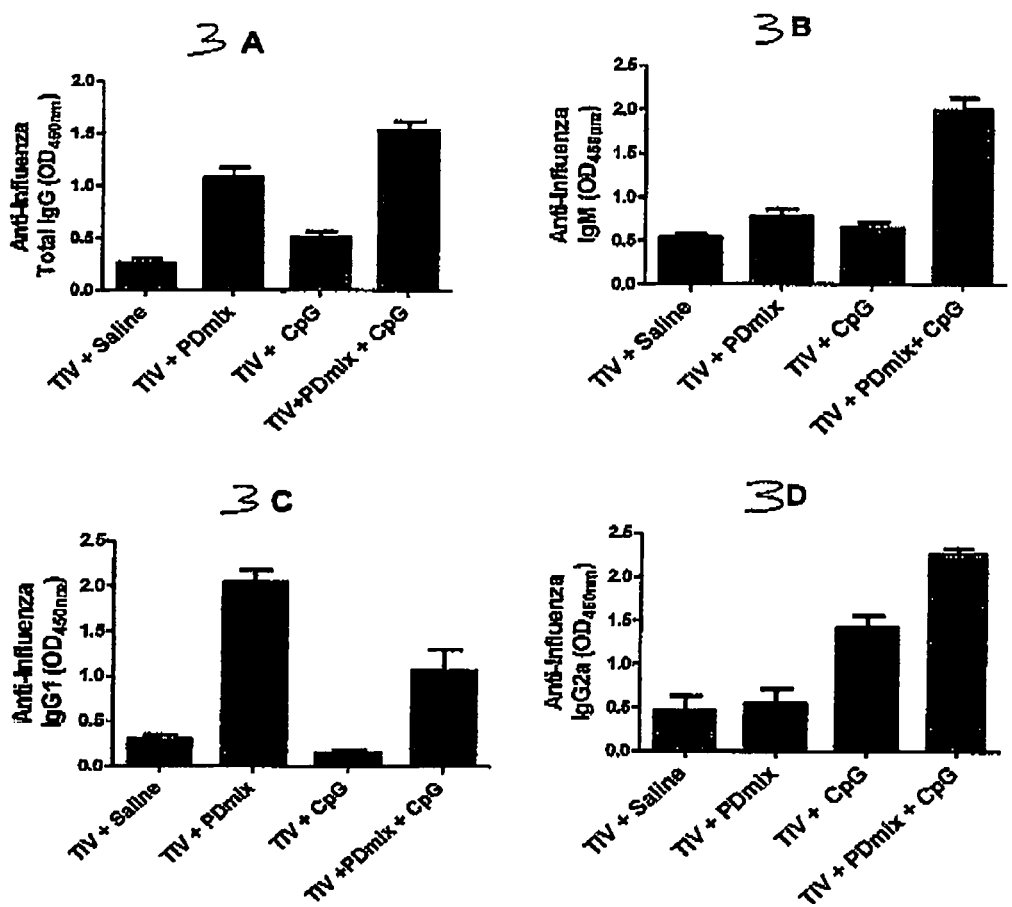

FIG. 3 shows four graphs labelled A-D showing the anti-influenza IgM, IgG2a, IgG1, and total IgG responses as measured by ELISA in sera from 200-300 day old female Balb/c mice (n=10/group) Immunised intramuscularly twice 14 days apart with a trivalent inactivated influenza vaccine. FIG. 3A shows serum anti-influenza total IgG levels, FIG. 3B shows serum anti-influenza IgM levels, FIG. 3C shows serum anti-influenza IgG1 levels and FIG. 3D shows serum anti-influenza IgG2a levels 42 days after the second immunization as measured by ELISA. Shown are group mean OD+SD. The group co-administered inulin particles (PDmix) plus a TLR9 agonist PAMP (CpG2006 (SEQ ID NO:1)) achieved the highest anti-influenza antibody titres.

Figure 4:
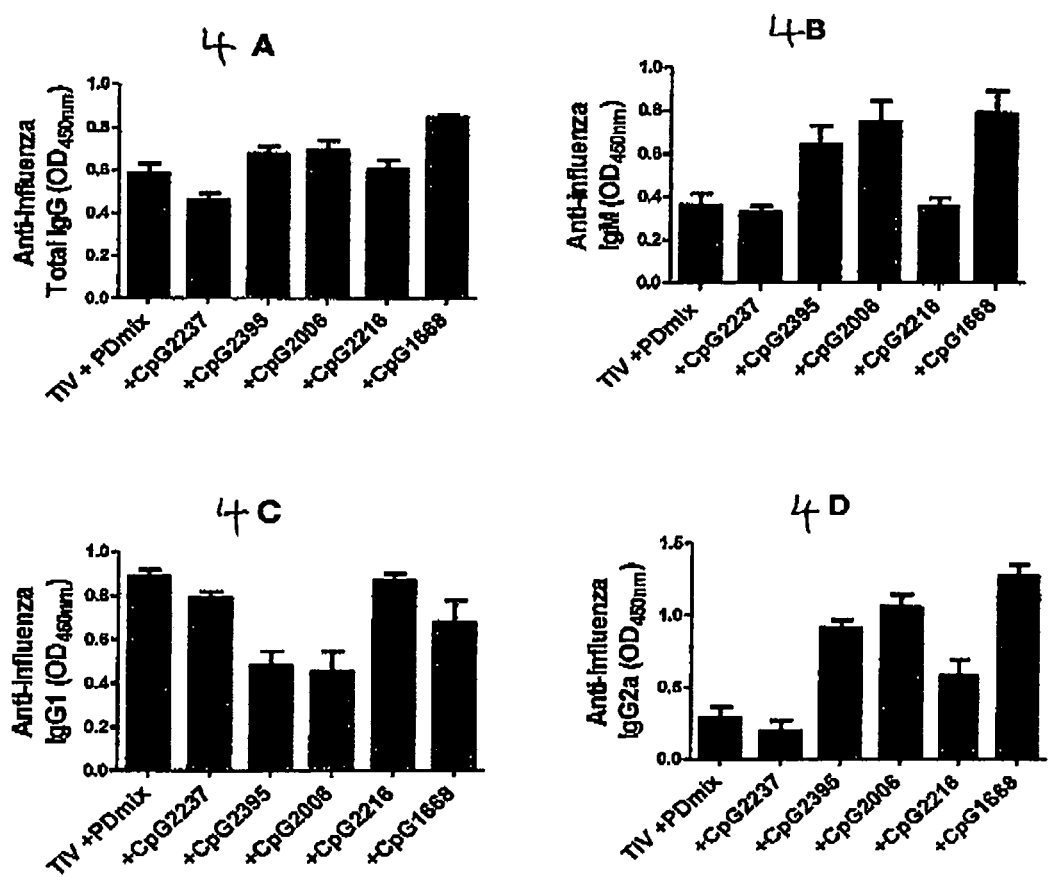

FIG. 4 shows four graphs labeled A-D showing the immunogenicity in mice of trivalent influenza vaccine (TIV) formulated with an inulin particle formulation PDmix alone or combined with a range of TLR9 agonist PAMPs. FIG. 4A shows serum anti-influenza total IgG levels, FIG. 4B shows serum anti-influenza IgM levels, FIG. 4C shows serum anti-influenza IgG1 levels and Fig. D shows serum anti-influenza IgG2a levels, 28 days after the second immunization as measured by ELISA. Shown are group mean OD+SD. The co-administration of TIV with PDmix and either CpG1688, CpG2006 (SEQ ID NO:1) or CpG2395 (SEQ ID NO:5) all showed synergy over the individual components in increasing anti-influenza total IgG, IgG2a and IgM titers. CpG2216 (SEQ ID NO:4) and CpG2237 (SEQ ID NO:6) had no effect on the antibody response.

Figure 5:
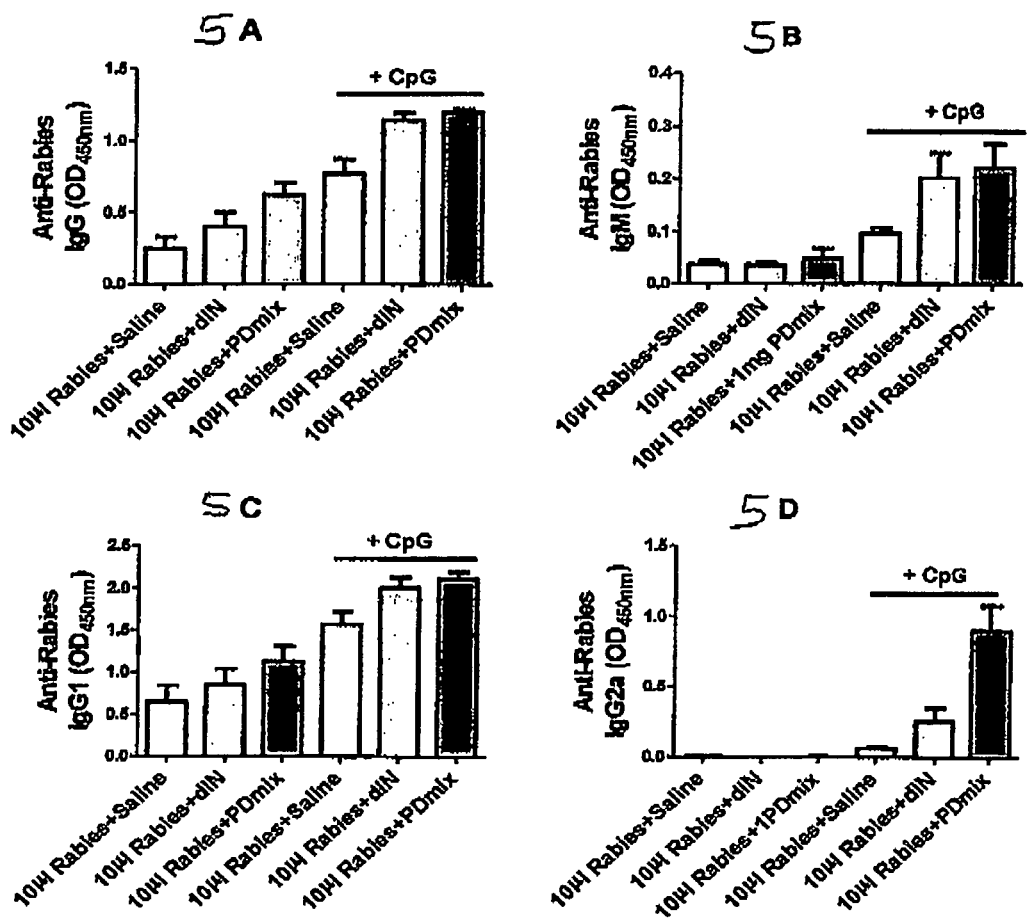

FIG. 5 shows four graphs labeled A-D showing the immunogenicity in mice of rabies vaccine (MIRV) formulated with either of two inulin particle formulations (dIN or PDmix) alone or combined with a TLR9 agonist CpG1668. FIG. 5A shows serum anti-rabies total IgG levels, FIG. 5B shows serum anti-rabies IgM levels, FIG. 5C shows serum anti-rabies IgG1 levels and FIG. 5D shows serum anti-rabies IgG2a levels 14 days after the second immunization as measured by ELISA. Shown are group mean OD+SD. The combination of either dIN or PDmix with CpG1668 plus MIRV provided the highest anti-rabies total IgG, IgG1, IgG2a and IgM.

Figure 6:
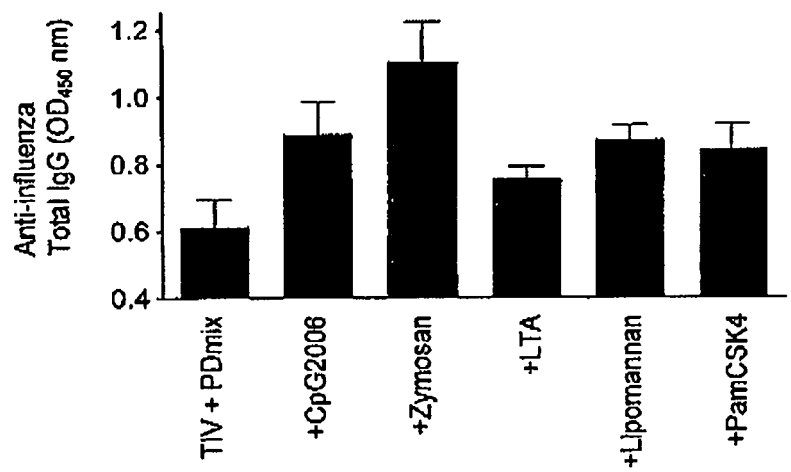
Figure 6:
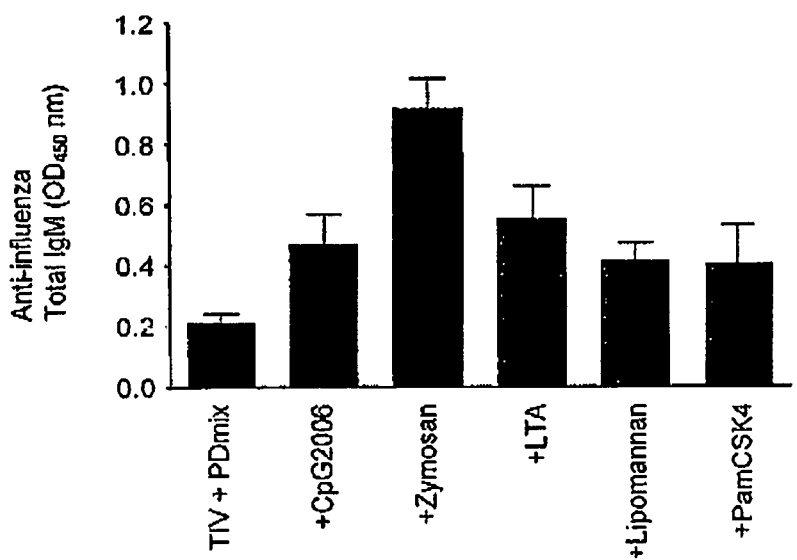

FIG. 6 shows four graphs labeled A-D showing the immunogenicity in mice of trivalent influenza vaccine (TIV) formulated with an inulin particle formulation PDmix alone or combined with a range of TLR2 agonist PAMPs (zymosan, LTA, Lipomannan and PamCSK4) as compared to the TLR9 agonist PAMP CpG2006 (SEQ ID NO:1). FIG. 8A shows serum anti-influenza total IgG levels, FIG. 6B shows serum anti-influenza total IgM levels, FIG. 6C shows serum anti-Influenza IgG1 levels and FIG. 6D shows serum anti-influenza IgG2a levels 14 days after the second immunization as measured by ELISA. Shown are group mean OD+SD.

Figure 7:
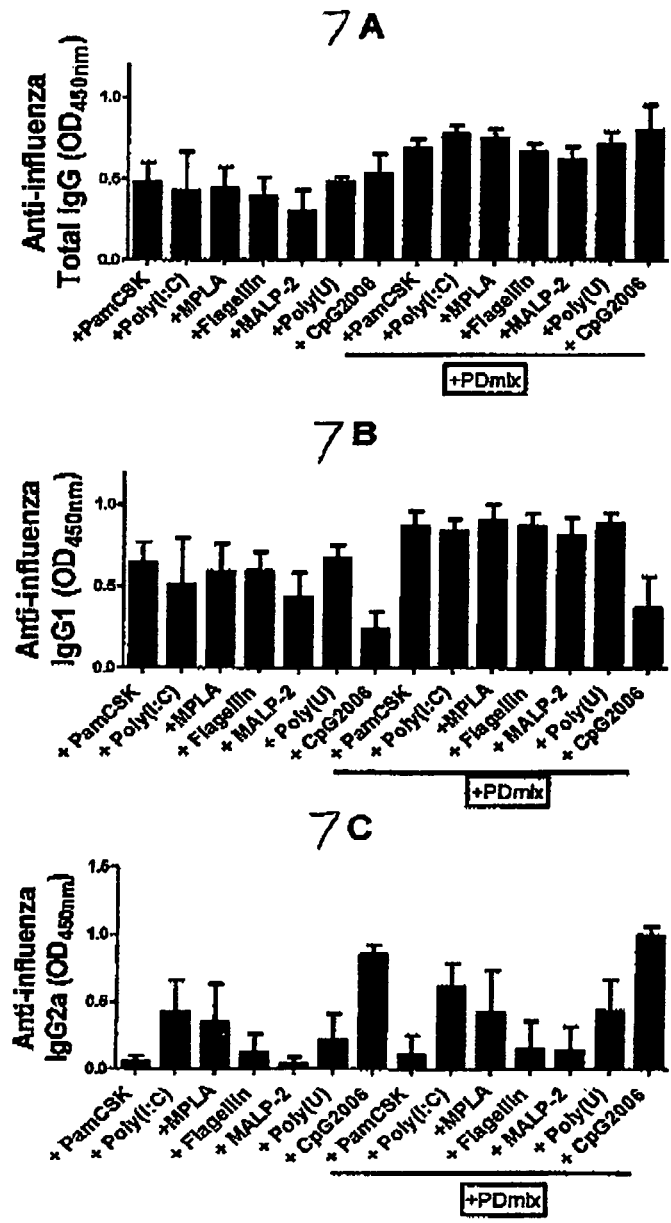
Figure 8:
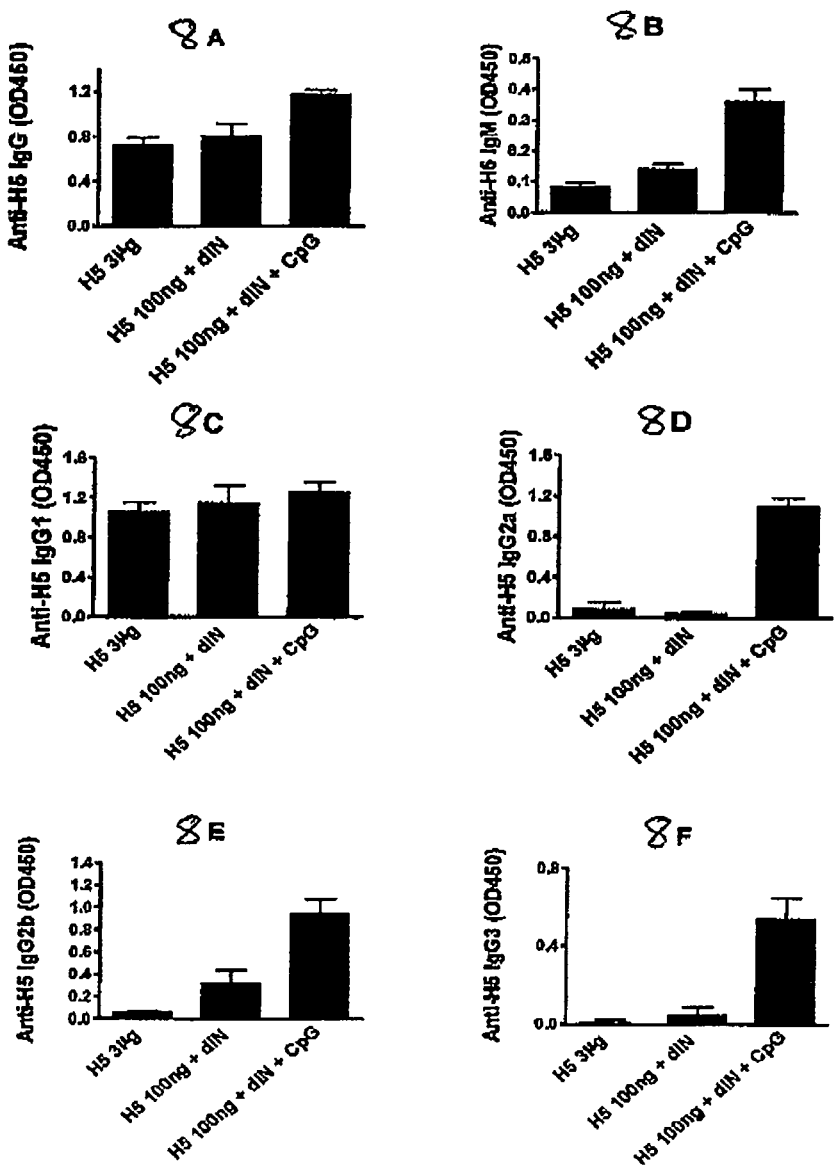

FIG. 7 shows three graphs labeled A, B, C, showing the favourable immune enhancing effect of combinations of inulin particles with various PAMPs on immunogenicity in mice of TIV vaccine. FIG. 6A shows serum anti-influenza total IgG levels, FIG. 6B shows serum anti-Influenza IgG1 levels and FIG. 6C shows serum anti-influenza IgG2a levels 42 days after the second immunization as measured by ELISA. Shown are group mean OD+SD, FIG. 8 shows six graphs labeled A, B, C, D, E, F, showing the favourable immune enhancing and antigen-sparing effect of combinations of inulin particles (dIN) with a TLR9 agonist PAMP, CpG2006 (SEQ ID NO:1) on immunogenicity in mice of a recombinant pandemic influenza vaccine, rH5. Balb/c mice at 6-8 weeks of age (n=5-8/group) were immunised intramuscularly twice 21 days apart, with 50 μl of a vaccine formulation containing between 3 ng and 3 μg of influenza recombinant H5 (rH5) serotype hemagglutinin protein (rH5) (Protein Sciences Corp, Meriden, USA) plus either dIN 1 mg or dIN 1 mg mixed with CpG2008 (SEQ ID NO:1) 5 μg. FIG. 8A shows serum ant-H5 total IgG, FIG. 8B shows anti-H5 IgM, FIG. 8C shows anti-H5 IgG1, FIG. 8D shows anti-H5 IgG2a, FIG. 8E shows anti-H5 IgG2b, and FIG. 8F shows anti-H5 IgG3 14 days after the second immunization as measured by ELISA. Shown are group mean OD+SD.

Figure 9:
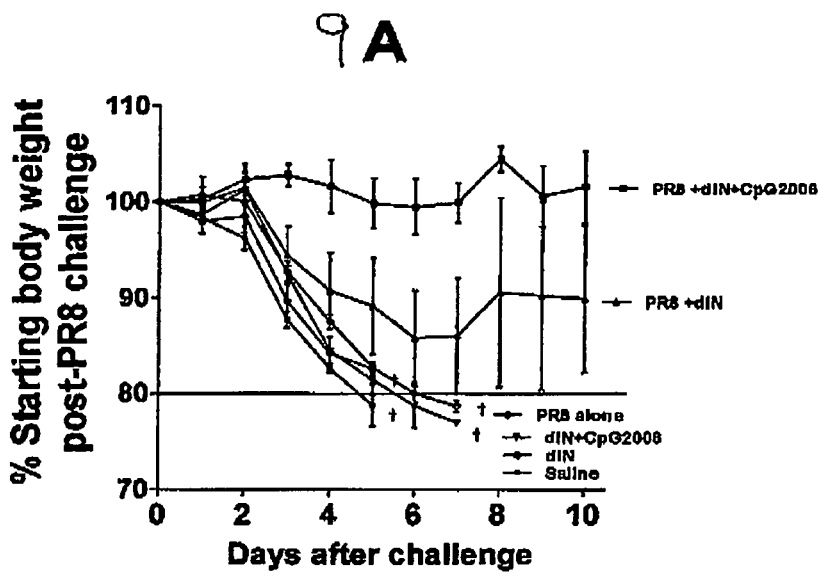
Figure 9:
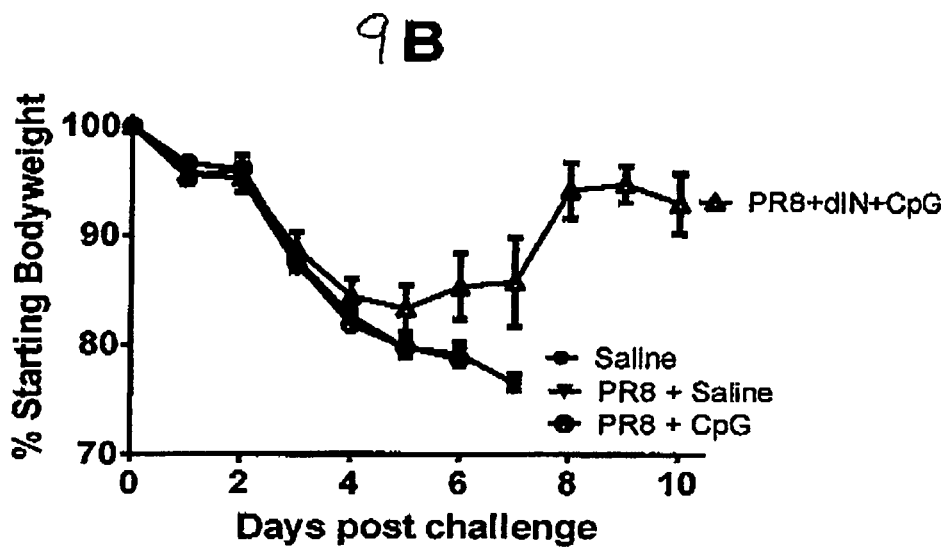

FIG. 9 shows 2 graphs labeled 9A and 9B showing the favourable immune enhancing effect of combinations of inulin particles (dIN) with a TLR9 agonist PAMP, CpG2006 (SEQ ID NO:1) together with H1N1 PR8 vaccine on survival of mice after challenge with lethal PR8 virus dose, FIG. 9A shows mice receiving combinations of Inulin particles (dIN) with a TLR9 agonist PAMP, CpG2006 (SEQ ID NO:1) together with H1N1 PR8 vaccine had complete protection with no weight loss or clinical disease, whereas PR8+dIN without CpG was only partially protective. FIG. 9B shows again in a separate study that mice receiving combinations of Inulin particles (dIN) with a TLR9 agonist PAMP, CpG2006 (SEQ ID NO:1) together with H1N1 PR8 vaccine were protected against death, whereas PR8+CpG gave no protection.

Figure 10:
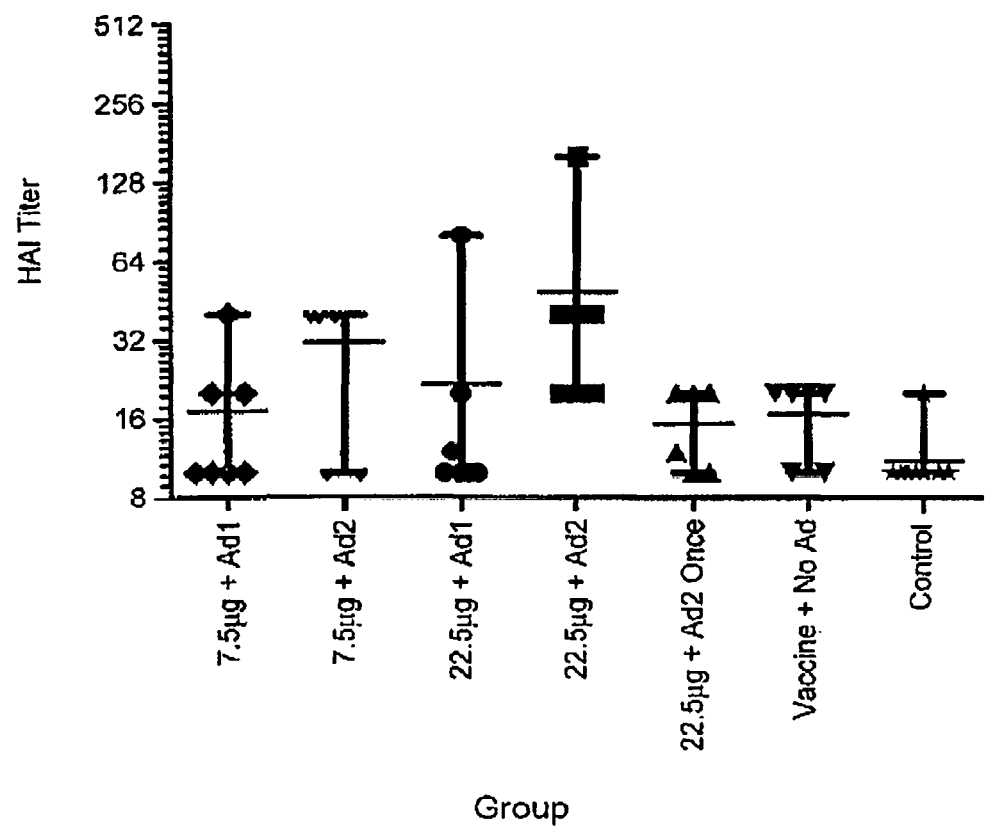
Figure 10:
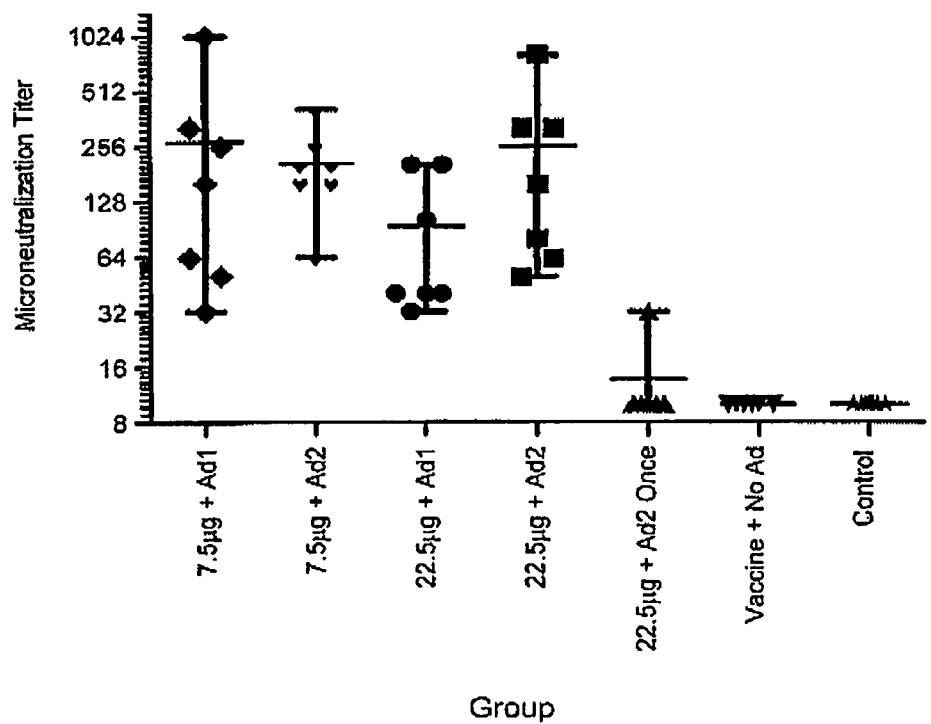

FIG. 10 shows four graphs labeled 10 A-D that show the hemagglutination inhibition titres (HI) (FIG. 10A & 10B) and microneutralisation (MN) titres (FIGS. 10O & 10O) in immunized ferrets measured at the time of the booster dose (21 days prior to challenge) (FIGS. 10A and 10C) and 14 days after the booster dose (7 days prior to challenge) (FIGS. 10B and 10D), Ferrets vaccinated with two doses of H5N1 with Ad2 had the highest neutralizing antibody titers, consistent with enhanced immune response when H5N1 antigen was combined with a formulation of inulin particles plus a TLR9 agonist.

Figure 11:
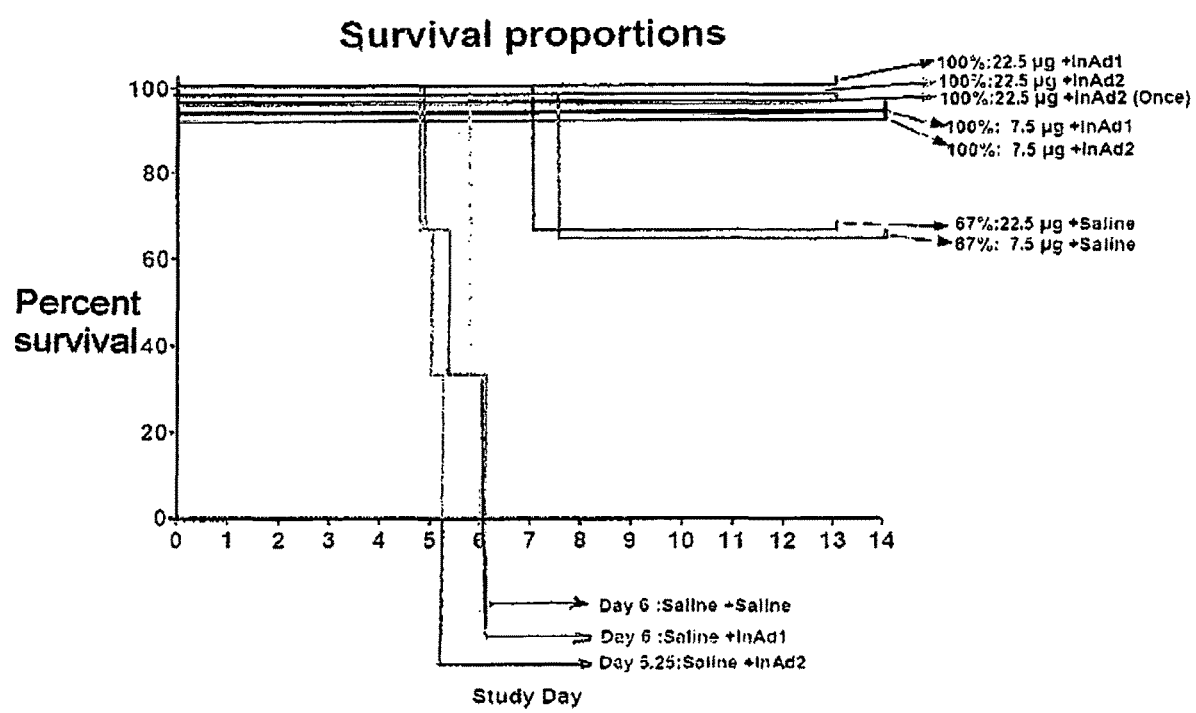

FIG. 11 shows a graph showing enhanced (100%) survival post lethal H5N1 challenge In ferrets that received Ad1- or Ad2-adjuvanted H5N1 vaccine, including the group that received just one immunization with 22.5 μg H5N1 vaccine+Ad2. Each of the 10 groups is denoted by survival percent: vaccine dose (or saline)+adjuvant identify (or saline). The survival of the five adjuvanted-vaccine groups were significantly greater than for the two unadjuvanted vaccine groups (Log-Rank test, p=0.05) and from the three unvaccinated control groups (Log-Rank test, p<0.001).

Figure 12:
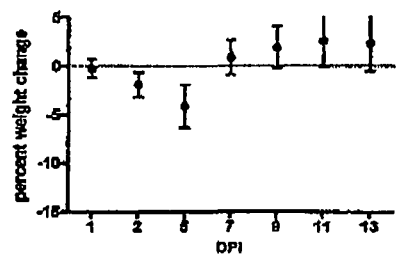
Figure 12:
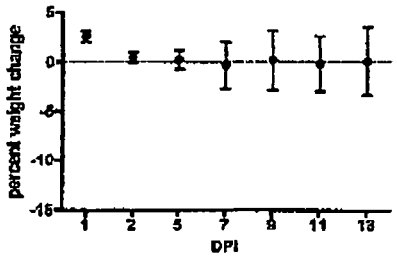
Figure 12:
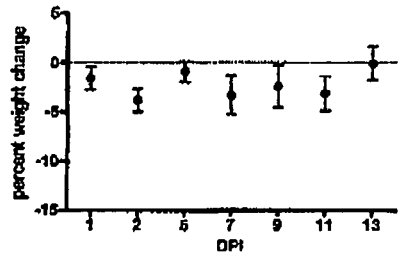
Figure 12:
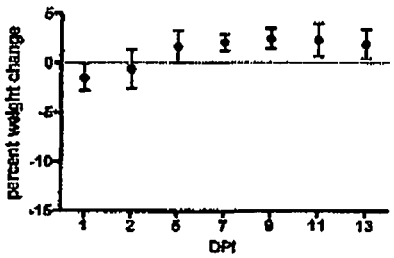
Figure 12:
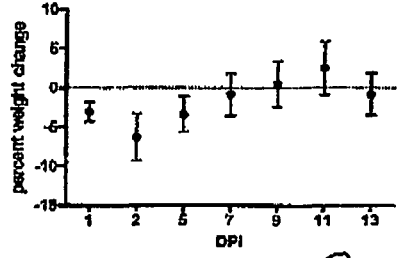
Figure 12:
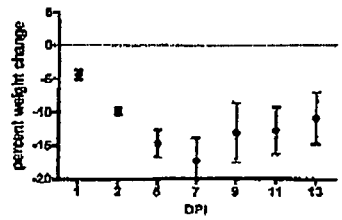
Figure 12:
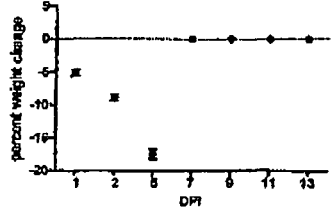

FIG. 12 shows seven graphs labeled 12 A-G that show the group mean weight change in immunized ferrets post challenge with H5N1 virus. Ferrets vaccinated with two doses of H5N1 with Ad2 did not lose any weight, consistent with enhanced protection when the H5N1 antigen was combined with a formulation of Inulin particles plus a TLR9 agonist.

Figure 13:
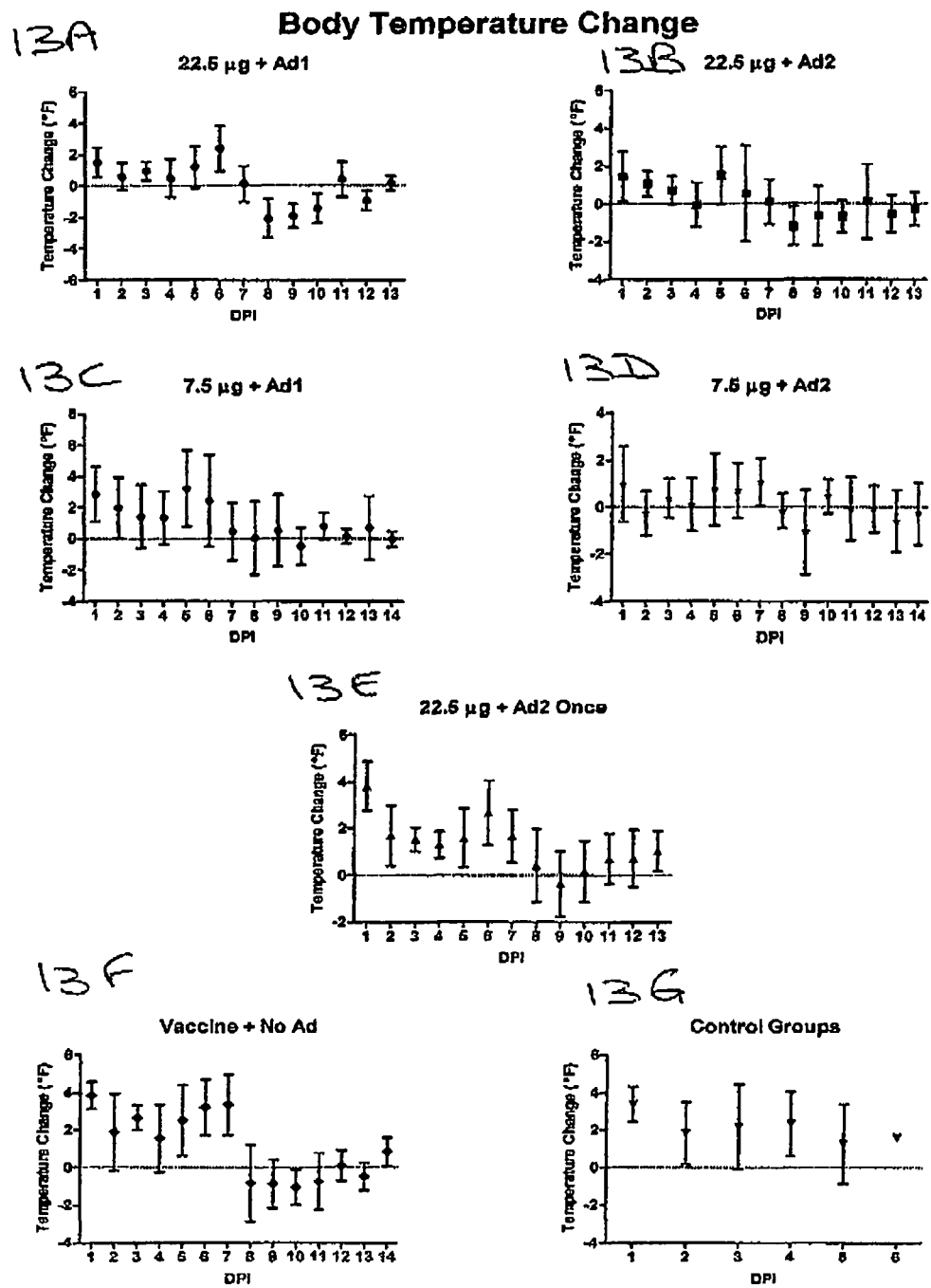

FIG. 13 shows seven graphs labeled 13 A-G that show the group mean temperature change in immunized ferrets post lethal challenge with H5N1 virus. While four ferrets in the Ad1 (inulin article alone)-adjuvanted vaccine groups demonstrated fever, no ferrets in the Ad2 (inulin particle+CpG)-adjuvanted group experienced fever, consistent with enhanced protection when the 115N1 antigen was combined with a formulation of Inulin particles plus a TLR9 agonist.

Figure 14:
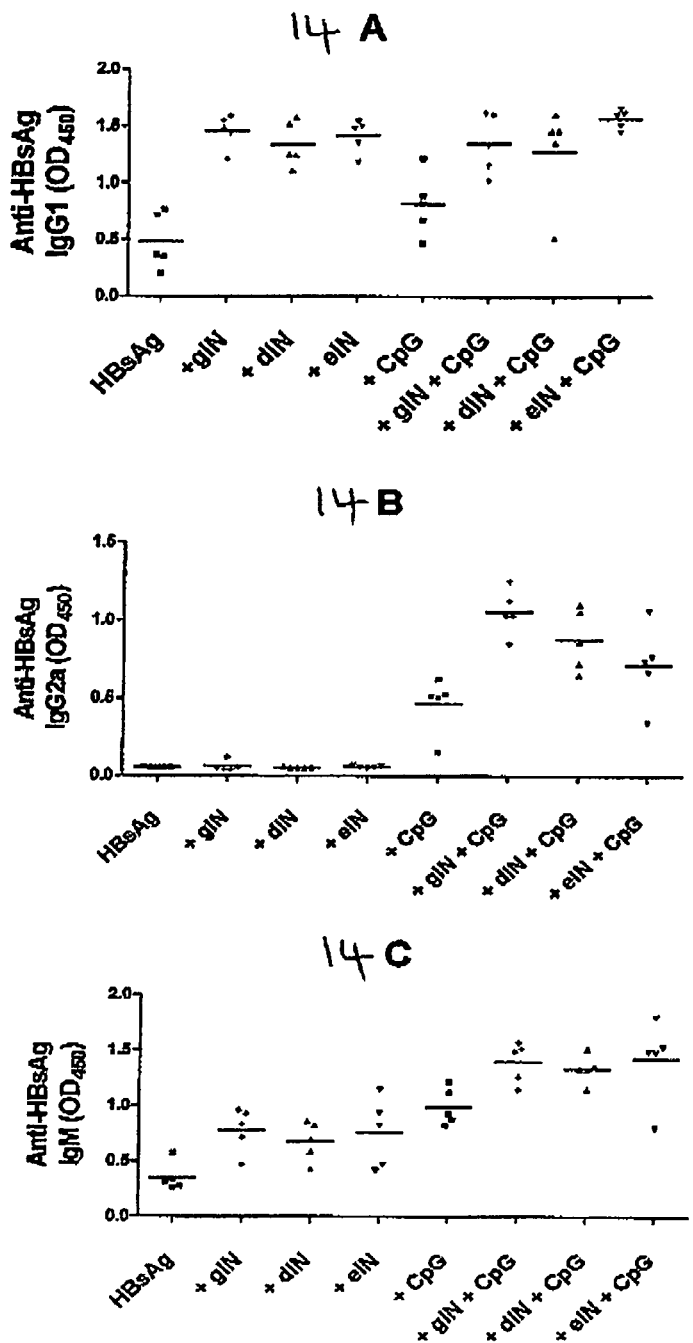

FIG. 14 shows three graphs labeled 14 A-C that show gIN, dIN or eIN all had a synergistic enhancing effect with the CpG in the Induction of anti-HBsAg IgG1, IgG2a and 1gM consistent with the synergistic effect on PAMP Innate immune activators being a shared property of different polymorphic forms of inulin particles. Adult Balb/c mice were immunized Intramuscularly twice 21 days apart, with HBsAg together with either gIN, dIN or eIN inulin particles alone or together with the TLR9 PAMP, CpG2006 (SEQ ID NO:1). FIG. 14A shows serum anti-HBsAg IgG1, FIG. 14B shows serum anti-HBsAg IgG2a levels and FIG. 14C shows serum anti-HBsAg IgGM levels after the second immunization as measured by ELISA. Shown are group mean OD+SD.

DETAILED DESCRIPTION OF THE INVENTION

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook. et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984), Current Protocols in Immunology ISBN 9780471522768 (Publisher: John Wiley and Sons Inc), Vaccine Adjuvants and Delivery Systems (Manmohan Singh ed. 2007). Methods in Molecular Biology, ISBN 9781607615842 (Publisher: Springer), History of Vaccine Development 2011, ISBN:1441913386 (Publisher: Springer)

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As known to those experienced in the art, innate immune activation can be used to enhance the type or magnitude of an adaptive immune memory response. Enhancement or modulation of the adaptive immune response is advantageous during vaccination or during allergen desensitisation, as it can provide a means to magnify or extend the duration of the immune memory response against a particular pathogen, or alter the type of immune response to a more beneficial response. For example, for some pathogens, it may be advantageous to induce a strong antibody (Th2) response to the immunizing antigen, whilst for other pathogens, it may be advantageous to induce a strong Th1 response or a strong Th17 response. On the other hand, for antigens such as allergens it may be advantageous to suppress the existing IgE response and instead induce a Th1 response to the allergen. It has been discovered according to the current invention that the combination of inulin particles with an innate immune activator enables a variety of unique patterns of immune response to be obtained that can, for example, be used to modulate the adaptive immune memory response to a co-administered antigen to a favoured type or direction.

The present invention provides in a first aspect, a composition comprising or consisting of inulin particles for use in the reduction or inhibition of inflammation, and/or for treating or preventing inflammatory disease, in a subject.

A second aspect of the present invention provides an immunological and/or pharmaceutically acceptable composition comprising (a) an anti-inflammatory component, such as inulin particles and/or one or more other anti-inflammatory inhibitors of IL-1; together with (b) a substance comprising or consisting of one or more species of an innate immune activator such as a pathogen-associated molecular pattern (PAMP). Without wishing to be bound by theory, a favourable immune interaction occurs because each of the two components of the immunological composition regulate transcription of an independent set of immune genes, such that the pattern of immune genes expressed in response to the combined immunological composition is unique to the combination and different to the patterns of gene expression induced by the individual components.

A third aspect of the present invention provides a kit of parts comprising: (a) a first container that contains a composition comprising or consisting of an anti-inflammatory component, such particles of inulin and/or one or more other anti-inflammatory inhibitors of IL-1 (as discussed above in respect of the second aspect of the present invention); and (b) a second container that contains a substance comprising or consisting of a pathogen-associated molecular pattern (PAMP).

Thus, component (a) of the composition of the second aspect of the present invention, or the kit of the third aspect of the invention, comprises or consists of an anti-inflammatory component, such as an anti-inflammatory inhibitor of IL-1 or an anti-inflammatory inhibitor of NFκB.

In an embodiment of particular interest for the present invention the anti-inflammatory component comprises or consists of inulin particles. The term "inulin particle" as used herein refers not only to particles made from β-D-(2-1)polyfructofuranosyl-α-D-glucose (also known as inulin) but also to derivatives thereof such as β-D-(2-1) polyfructose which may be obtained by enzymatic removal of the end glucose from inulin, for example using an invertase or inulase enzyme capable of removing the end glucose. The term inulin particle also refers to any natural or synthetic particle that is constituted by, contains or is coated with inulin, or a derivative or mimetic thereof. Suitable inulin derivatives included within the scope of this term are derivatives of inulin in which the free hydroxyl groups have been acetylated, methylated, etherified or esterified, for example by chemical substitution with alkyl, aryl or acyl groups, by known methods. The stable inulin particle may be solid or hollow and may be wholly comprised of inulin molecules or may alternatively have a non-sugar core, skeleton or shell comprising, for example, carbohydrate compounds, metal compounds, proteins or lipids but which at its surface expresses inulin molecules either covalently or non-covalently bonded to the components comprising the core. Preferably, the inulin particle will be selected from the group of gIN, dIN and eIN, or modifications thereof. Most preferably, the inulin particle will be dIN. Preferably, the inulin particle will have a diameter in the size range of 20 nM to 20 μM. More preferably, the inulin particle will have a diameter in the size range of 0.1 to 5 μM. Most preferably the inulin particle will have a diameter in the size range of 0.5 to 5 μM.

In one embodiment, inulin particles as used in the present invention are stable inulin particles. The term "stable" as used herein refers to an inulin particle that is totally insoluble or predominantly insoluble or partially insoluble at the body temperature of the subject to whom it is to be administered. In this context, stability may optionally include the meaning that the inulin particles are insoluble when incubated at a temperature of up 16 to 25° C. or up to 30° C., 37° C., 40° C., 42° C., 45° C., 48*C, 50° C., 52° C., 55° C., 58° C., or 60° C. when present at a concentration of no greater than 0.5 mg/ml or 1 mg/ml or 2 mg/ml in distilled water or saline or phosphate buffered saline, for at least 10, 20, 30, 40, 50, or 60 minutes. The amount of insoluble inulin can be measured by changes in the optical density of the inulin suspension at 300 nm, 400 nm, 500 nm, 600 nm, 700 nm wavelength ($OD_{700}$) using a spectrophotometer and, in this context, an inulin particle can be said to be stable if it remains insoluble at the defined condition as indicated by the $OD_{700}$ not falling below a value that is 50%, 60%, 70%, 80%, 90%, 95%, 98%, 99%, 99.5%, 99.9% or substantially 100% of the $OD_{700}$ of the particle preparation in the same solvent and at the same concentration prior to incubation at the defined temperature (preferably when measured at a temperature that is 10° C. or more below the incubation temperature)

Other anti-inflammatory components, which may be used in component (a) of the composition of the second aspect, or the kit of the this aspect of the invention, instead of or as well as, inulin particles, may include—
(i) inhibitors of the IL-1 pathway genes or proteins, particularly those which are functionally-equivalent to inulin particles, in the sense of possessing an essentially equivalent anti-inflammatory property, activity and/or specificity and/or possessing an essentially equivalent immunomodulatory or adjuvant property,
(ii) one or more of IL1 receptor antagonists, IL1RA, Anakinra, Rilonacept, IL-1R/IL1RacP/Fc-fusion protein, Canakinumab, a human IL-113 antibody, IL1 receptor blockers, IL-1RII, indomethacin, non-steroidal anti-inflammatory drugs (NSAID), glucocorticoids, caspase inhibitors including caspase 1 inhibitors, inflammasome inhibitors including NALP3 antagonists, curcumin, resveratrol, chloroquine, P2X7 receptor inhibitors, ST2 receptor inhibitors, and/or ATP antagonists;
(iii) agents which up-regulate or activate the anti-inflammatory protein peroxisome proliferator-activated receptor gamma (PPAR-γ) or upregulate genes or proteins in the PPAR-γ pathway, particularly in monocytes and dendritic cells (PPAR-γ pathway genes are also upregulated by inulin particles). PPAR-γ upregulation has been previously shown to inhibit inflammatory responses including suppressing LPS-induced IL-1 and TNFα and conversely IL1 and TNFα PPAR-γ. Suitable agents may include one or more of rosiglitazone, pioglitazone, prostaglandin J2, curcumin, resveratrol, thiazolidenediones, Berberine, perfluorononanoic acid, RS5444, free fatty acids, vitamin D, and/or eicosanoids.
(iv) anti-inflammatory agents such as aspirin, ibuprofen, and naproxen, salicylic acid, submandibular gland peptide-T, phenylalanine-glutamine-glycine (FEG), ginger, turmeric, sesquiterpene lactone, Omega-3 fatty acids, prostaglandin-E, prostaglandin-E3, Curcumin, Mesalazine, Selective glucocorticoid receptor agonist, Lisofylline, Mofezolac, Oleocanthal, Ibuproxam, Cyclopentenone, prostaglandin, Cannabidiol, BMS-345541, BMS-470,539, Amlexanox, Amixetrine, Allicin, Actarit, Butylpyrazolidines, for example, Phenylbutazone; Mofebutazone; Oxyphenbutazone; Ciofezone; Kebuzone; Suxibuzone; Acetic acid derivatives and related substances, such as Indometacin; Sulindac; Tolmetin; Zomepirac; Diciofenac; Alclofenac; Bumadizone; Etodolac; Lonazolac; Fentiazac; Acemetacin; Difenpiramide; Oxametacin; Proglumetacin; Ketorolac; Aceclofenac; Bufexamac; Indometacin, Diclofenac, Oxicams, such as Piroxicam; Tenoxicam; Droxicam; Lomoxicam; Meloxicam; Propionic acid derivatives, such as Ibuprofen; Naproxen; Ketoprofen; Fenoprofen; Fenbufen; Benoxaprofen; Suprofen; Pirprofen; Flurbiprofen; Indoprofen; Tiaprofenic acid; Oxaprozin; Ibuproxam; Dexibuprofen; Flunoxaprofen; Alminoprofen; Dexketoprofen; Naproxcinod; Naproxen and esomeprazole; Naproxep and misoprostol; Vedaprofen; Carprofen; Tepoxalin. Fenamates, such as Mefenamic acid; Tolfenamic acid; Flufenamic acid; Meclofenamic acid; Flunixin, Coxibs, such as Celecoxib; Rofecoxib; Valdecoxib; Parecoxib; Etoricoxib; Lumiracoxib; Firocoxib; Robenacoxib; Mavacoxib; Cimicoxib, Other anti-inflammatory and antirheumatic agents, such as Nabumetone; Niflumic acid; Azapropazone; Glucosamine; Benzydamine; Glucosaminoglycan polysulfate; Proquazone; Orgotein; Nimesulide; Feprazone, Diacerein; Morniflumate; Tenidap; Oxaceprol, Chondroitin sulfate; Avocado and soyabean oil, unsaponifiables, Niflumic acid, Feprazone, combinations; Pentosan polysulfate; Aminopropionitrile; Anti-inflammatory/antirheumatic agents in combination with corticosteroids, such as Phenylbutazone and corticosteroids; Dipyrocetyl and corticosteroids; Acetylsalicylic acid and corticosteroids; Specific antirheumatic agents including Quinolines, such as Oxycinchophen, Gold preparations, such as Sodium aurothiomalate; Sodium aurothiosulfate; Auranofin; Aurothioglucose; Aurotioprol; and/or Penicillamine and similar agents, such as Bucillamine.

As a general rule, the inulin particle (or other equivalent anti-inflammatory component) may be used in an amount of between 0.001 mg and 100 mg per kilogram body weight of the subject to be immunised. For example, the inulin particle (or other equivalent anti-inflammatory component) of a composition of the present invention may be present at a concentration in the range of 0.1 mg to 100.0 mg per kilogram body weight. In another example, the inulin particle (or other equivalent anti-inflammatory component) of the composition may be administered to an adult human subject in a range of 1 to 100 mg per dose, such as a 20 mg per dose.

The term "adjuvant" refers to a substance or mixture that enhances the immune response to an antigen. Often, a primary immunization with an antigen alone, in the absence of an adjuvant, will fail to elicit an immune response.

The term "agonist" refers to a protein, nucleic acid, lipid, carbohydrate or chemical substance that interacts with a cellular receptor to produce a cellular response. Agonists that stimulate innate immune receptors may be of particular interest in the present invention.

The term "innate immune activator" is to be understood as referring to any substance that directly or indirectly activates a cell involved in the functioning of the innate immune system. Without limitation, innate immune activation may be manifest at the cellular level by one or more of changes in gene expression or protein production, induction of cytokine or chemokine production or secretion, changes in cell morphology, differentiation, cell division, changes in cell surface protein expression, chemotaxis, phagocytosis, exocytosis, autophagy, or apoptosis.

The term, "vaccine" is defined as an immuno-stimulatory treatment designed to elicit a beneficial immune response against a specific antigen, whether administered prophylactically or for the treatment of an already existing condition.

The term "immunogenic" refers to the ability of an antigen to elicit an immune response, including either humoral and/or cell-mediated immunity.

The term "immunologically-effective amount" as used herein in respect to an antigen or an innate immune activator refers to the amount of antigen or innate immune activator sufficient to elicit an immune response as measured by standard assays known to one skilled in the art. The effectiveness of an antigen as an immunogen, can be measured either by T-cell proliferation or cytokine secretion assays, by cytotoxicity assays, such as chromium release assays to measure the ability of a T-cell to lyse its specific target cell, or by measuring the levels of B-cell activity by measuring the levels of circulating antibodies specific for the antigen in serum, or by measuring the number of antibody spot-forming B cells, e.g. by ELISPOT. Furthermore, the level of protection of the immune response may be measured by challenging the immunized host with a replicating virus, pathogen or cell containing the antigen that has been immunised against. For example, if the antigen to which an immune response is desired is a virus or a tumour cell, the level of protection induced by the "immunogenically effective amount" of the antigen is measured by detecting the level of survival after virus or tumour cell challenge of the animals. Alternatively, protection can also be measured as the reduction in viral replication or tumour growth following challenge of the animals. The amount of antigen necessary to provide an immunogenic amount is readily determined by one of ordinary skill in the art, e.g., by preparing a series of vaccines of the invention with varying concentrations of antigen, administering the vaccine formulations to suitable laboratory animals (e.g., mice, rats, guinea pigs, or rabbits), and assaying the resulting immune response by measuring serum or mucosal antibody titers, antigen-induced swelling in the skin (delayed type hypersensitivity assay), T-cell proliferation, cytokine production or cytotoxic activity, protection against pathogen challenge and the like.

The term 'parenteral' refers to injection of a vaccine into any tissue of the body and includes intramuscular, subcutaneous, intradermal, intraperitoneal and intraocular routes of vaccine administration, by methods and delivery devices well known in the art.

In important embodiments of the aspects of the present invention, the subject is a human. In other embodiments, the subject is selected from the group consisting of an animal, dog, cat, horse, camel, cow, pig, sheep, goat, chicken, hawk, rabbit and fish. The term "animal" includes all domestic and wild mammals, fish, fowl, and includes, without limitation, cattle, horses, swine, sheep, goats, camels, dogs, cats, rabbits, deer, mink, chickens, ducks, geese, turkeys, game hens, and the like.

In one embodiment, as an additional component, the composition of the invention may also optionally include an immunologically-effective amount of a chemical substance that activates one or more types of innate immune cell, such as a monocyte, dendritic cells, NK cell, lymphocyte or granulocyte. As known in the art, examples of chemicals that induce activation of innate immune cells include leukotrienes, prostaglandins, cytokines, chemokines, interferons, kinins, vitamin D, phorbol myristate acetate, ionomycin, mitogens, opsonins, histamine, bradykinin, serotonin, leukotrienes, cAMP, antimicrobial peptides, and pro-drugs or inducers of the aforementioned substances.

In an important embodiment, the PAMP innate immune activator of the current invention is an immunologically-effective amount of a substance that binds to an innate immune receptor. Currently known innate immune receptors include TLR-1, TLR-2, TLR-3, TLR-4, TLR-5, TLR-6, TLR-7, TLR-8, TLR-9, murine TLR-11; NOD-1, NOD-2, other NOD-like receptors (NLRs) such as NLRP1, NLRP3, NLRP12, NLRC4; DECTIN-1; DC-SIGN; AIM-2; mannose receptors including C-type lectins, MD2; CD14; LBP; CARD (caspase activating and recruitment domain)-containing proteins, such as RIG-1 (retinoic acid-inducible gene-1) and MDA-5 (melanoma differentiation-associated gene-5). LGP2 and ASC, scavenger receptors including CD-36, CD-68, and SRB-1, C reactive protein, mannose binding lectin, complement factors including C3a and C4b and complement receptors, and N-formyl Met receptors including FPR and FPRL1. Of particular interest for the present invention are PAMPs that bind and activate TLR-1, -2, -3, -5, -6, -7, and -9 and NOD-like receptors. More preferred are TLR3, TLR9 and NOD2 receptor agonists. Most preferred are TLR9 agonists.

In an important embodiment of all aspects of the present invention, an immunologically-effective amount of one or more PAMPs (pathogen-associated molecular patterns) is/are used. A PAMP is a structurally conserved molecule derived from a pathogen that is immunologically distinguishable from host molecules, and is recognised by and specifically binds to an innate immune receptor. PAMPs are present in certain protein, lipid, lipoprotein, carbohydrate, glycolipid, glycoprotein, and nucleic acids expressed by particular pathogens and include TLR2 agonists including di- and tri-acyl lipopeptides, lipotechoic acid, zymosan, peptidoglycan, porins, Lipoarabinomannan, Phospholipomannan, Glucuronoxylomannan, glycosylphosphatidylinositol (GPI)-anchored proteins in parasites, TLR3 agonists including double stranded RNA, including synthetic dsRNA for example polyinosinic:polycytidylic acid (poly I:C), TLR4 agonists including mannan, glucuronoxylomannan, heat shock protein, fibrinogen and synthetic MPL, TLR5 agonists including flagellin, TLR6 agonists including lipotechoic acid, TLR7 and TLR8 agonists including viral or synthetic single stranded (ss)RNA, for example, imiquimod and resiquimod (R848), and TLR9 agonists including unmethylated cytosine-guanine dinucleotide oligonucleotide sequences (CpG ODN) and hemozoin, RIG-1 agonists such as viral or synthetic double-stranded (ds) RNA, MDA5 agonists such as viral or synthetic dsDNA, NOD1 agonists including peptidoglycan containing the muramyl dipeptide NAG-NAM-gamma-D-glutamyl-meso diaminopimelic acid, NOD2 agonists including peptidoglycan containing the muramyl dipeptide NAG-NAM-L-alanyl-isoglutamine, RIG1 and MDA5 agonists including ssRNA and dsRNA, N-formyl Met receptor agonists including N-formyl methionine. Hence, a PAMP innate immune activator as used by the current invention may be selected from any of the above groups of agonists or synthetic analogues or derivatives thereof.

In an important embodiment of the aspects of the present invention, the substance comprising or consisting of one or more pathogen-associated molecular pattern (PAMP) may be present, or administered, at an immunologically effective amount and/or concentration in the range of 0.01 to 500 micrograms per kilogram of body weight.

In an important embodiment of the aspects of the present invention, each substance comprising or consisting of a pathogen-associated molecular pattern (PAMP) is present, or administered, as a pure, distinct and single molecular and chemical entity.

In one embodiment of the aspects of the present invention, the substance comprising or consisting of a pathogen-associated molecular pattern (PAMP) may be present, or administered, in a highly purified state, whereby each distinct and single molecular and chemical PAMP entity is at a purity of at least 50%, 60%, 70%, 80%, 90%, 95%, 96%, 97%, 98%, 99%, 99.9%, 99.99%, 99.999%, essentially 100%.

In an important embodiment, the PAMP of the current invention is a TLR agonist. There are presently believed to be approximately 10-15 different types of TLR in most mammalian species. The different TLRs bind and are activated by a range of natural and synthetic ligands. Different TLRs signal through different signalling molecules, although a feature in common is that they all activate the inflammatory transcription factor NFκB.

In an embodiment, the PAMP of the current invention is a TLR1 agonist, such as a TLR1 agonist drawn from the group of a triacyl lipopeptide and Pam3CSK4. Most preferred is Pam3CSK4.

In an embodiment, the PAMP of the current invention is a TLR2 agonist, such as a TLR2 agonist drawn from the group of a glycolipid, lipoteichoic acid, peptidoglycan, HSP70, zymosan, and Pam3CSK4.

In an embodiment, the PAMP of the current invention is a TLR3 agonist, such as a TLR3 agonist drawn from the group of a double-stranded RNA, poly (I:C), poly (I:C-LC) (Hiltonol™), and poly I; polyC12 U (Ampligen™). Most preferred is poly (I:C).

In another embodiment, the PAMP of the current invention is a TLR4 agonist, such as a TLR4 agonist drawn from the group of monophosphoryl lipid A (MPLA), heat shock proteins, fibrinogen, heparan sulfate fragments, hyaluronic acid fragments, and synthetic TLR4 agonists including E6020, GLA and LPS peptide mimotopes. Most preferred is a synthetic TLR4 agonist that preferentially signals through the TIR-domain-containing adapter-inducing interferon-β (TRIF) and not the NFκB pathway. Due to toxicity and regulatory requirements, lipopolysaccharide (LPS) TLR4 agonists and substances containing LPS (such as endotoxin) should be avoided in the invention. The amount of LPS and/or endotoxin in substances and compositions used in the aspects of the present invention may be less than 100 EU per dose, such as less than 90, 80, 70, 60, 50 40, 30, 20, 10, 5, 4, 3, 2, 1 or less EU per dose. The concentration of LPS and/or endotoxin in substances and compositions used in the aspects of the present invention may be less than 200 $EU/m^3$, such as less than 150, 100, 90, 80, 70, 60, 50 40, 30, 20, 10, 5, 4, 3, 2, 1 or less $EU/m^3$ In another embodiment, the PAMP of the current invention is a TLR5 agonist, such as a TLR5 agonist drawn from the group of bacterial or synthetic flagellins. Most preferred is synthetic flagellin.

In another embodiment, the PAMP of the current invention is a TLR6 agonist, such as a TLR6 agonist drawn from the group of diacyl lipopeptides. Most preferred is diacyl lipopeptide.

In another embodiment, the PAMP of the current invention is a TLR7 agonist, such as a TLR7 agonist drawn from the group of viral single-stranded RNA, imidazoquinoline, gardiquimod, loxoribine, bropirimine, CL264, R848, and CL075. Most preferred is R848.

In another embodiment, the PAMP of the current invention is a TLR8 agonist, such as a TLR8 agonist drawn from the group of single-stranded RNA, PolyU, imiquimod, resiquimod, ssPolyU/LyoVec and ssRNA40/LyoVec.

In an important preferred embodiment, the PAMP of the current invention is a TLR9 agonist. More preferably, the TLR9 agonist is a CpG ODN. The term "CpG" or "CpG ODN molecule", as used herein, is to be understood as referring to a ODN molecule comprising a motif wherein a cytosine nucleoside is followed by a guanine nucleoside, linked by a phosphate molecule in the normal manner seen in polynucleotide sequences (i.e. a "CpG motif"), wherein the cytosine nucleoside is unmethylated. CpG motifs are prevalent in bacterial and viral genomes, but are rare in vertebrate genomes. Further, CpG motifs are generally unmethylated in prokaryotic organisms, whereas in eukaryotic organisms, DNA methyltransferases generally methylate 70-80% of the CpG motifs present. It also refers to a synthesised oligonucleotide molecule comprising at least one unmethylated CpG motif. Frequently, more than one CpG motif is present. A variety of CpG oligonucleotide molecules are commercially available. They are typically between 18-24 nucleotides in length, but a person skilled in the art will appreciate that CpG oligonucleotide molecules of other lengths are also suitable. The CpG oligonucleotide molecules can comprise various nucleotide sequences surrounding at least one CpG motif, as different nucleotide sequences have been shown to stimulate TLR9 to varying degrees. Class B ODN are strong stimulators of human B cell and monocyte maturation. They also stimulate the maturation of plasmacytoid dendritic cells (pDC) but to a lesser extent than Class A ODN and induce only very small amounts of IFNα. Class C ODN have features of both Class A and Class B ODN. Preferably a Class B or Class C CpG ODN is used in the current invention. As know to those skilled in the art, the CpG backbone can be varied from a natural phosphodiester backbone to a synthetic phosphorothioate backbone or a mixture of the two types of backbones to increase the stability of the ODN. In a preferred embodiment of the invention, the CpG PAMP has a natural phosphorothioate backbone and is 18 to 28 nucleotides in length. In another preferred embodiment of the invention, the TLR9 agonist is a Class B or C CpG ODN with a synthetic phosphorothioate backbone and is 18 to 28 nucleotides in length. In a preferred embodiment, the PAMP is drawn from the group of CpG2006 (SEQ ID NO:1), CpG1826 (SEQ ID NO:2) and, most preferably, CpG7909 (SEQ ID NO:3).

In another embodiment, the PAMP of the current invention is a NOD-like receptor agonist. Preferably, the agonist is to the NOD1 receptor and is drawn from the group of, Acylated derivative of iE-DAP) (C12-iE-DAP), D-gamma-Glu-mDAP (iE-DAP), L-Ala-gamma-D-Glu-mDAP (Tri-DAP). More preferably, the agonist is to the NOD2 receptor and is drawn from the group of muramyl dipeptide (MDP), muramyl tripeptide, L18-MDP, M-TriDAP, murabutide, PGN-ECndi, PGN-ECndss, N-glycolylated muramyl dipeptide, and PGN-Sandi. Most preferably, the NOD2 agonist is murabutide.

In another embodiment, the PAMP of the current invention is an agonist of a C-type lectin receptor. More preferably, the C-type lectin receptor agonist binds to one of the group of macrophage mannose receptor, CLEC-2, DEC205/CD205, DC-SIGN-like, DC-ASGPR (MGL)/CD301, Dectin-1, Langerin/CD207. Mincle and CLR BDCA-2/CD303. Most preferably the C-type lectin receptor agonist is drawn from the group of Beta-1,3-glucan, zymosan, Heat-killed *C. albicans*, cord factor, and Trehalose-6,6-dibehenate.

In another embodiment, the PAMP of the current invention is an agonist of nucleotide-binding oligomerization domain-like receptor family (NLR) proteins including the retinoic acid inducible gene-based-1-like helicase receptor family that include RIG-1 and MDA-5. Preferably, it is drawn from the group of poly(I:C), Poly(dA:dT), Poly(dG:dC) and 5'ppp-dsRNA.

In another embodiment, the PAMP of the current invention is an agonist of a DNA sensing protein drawn from the group of DNA-dependent activator of interferon-regulatory factors (DAI) and absent in melanoma 2 (AIM2). Preferred is Poly(dA:dT).

In another important embodiment, the PAMP of the current invention is an agonist of a class A, B or C scavenger receptor expressed on innate immune cells, which may, for example, be drawn from the group of SCARA1, SCARA2, SCARA3, SCARA4, SCARA5, SCARB1, SCARB2, SCARB3, MARCO, CD36, SR-B1, CD68, and LOX-1. Preferred is low-density lipoprotein (LDL), oxidised LDL, acetylated LDL or chemically modified LDL.

In another embodiment, the PAMP of the current invention is an agonist of NLRP1 or NALP3. Preferred is hemozoin or ATP.

The selected PAMP innate immune activator of the current invention may be added to the substances and composition used in the aspects of the present invention in an "immunologically-effective" immunopotentiating amount which, as known to those of ordinary skill in the art, may vary depending on the species, strain, age, weight and sex of the animal or human being treated with the immunological composition.

The term "immunopotentiating amount" refers to the amount of an immunological formulation needed to effect an increase in immune response, as measured by standard assays known to one skilled in the art. As can be appreciated, each immunological formulation containing inulin particles (or other equivalent anti-inflammatory component) may have an effective dose range that may differ depending on the PAMP innate immune activator and specific inulin polymorphic form (or other equivalent anti-inflammatory component) used. Thus, a single dose range cannot be prescribed which will have a precise fit for each possible inulin particle (or other equivalent anti-inflammatory component) and PAMP innate immune activator combination within the scope of this invention. However, the immunopotentiating amount may easily be determined by one of ordinary skill in the art. The effectiveness of immune activation can be measured either by an immune cell proliferation assay, or assays measuring changes in the level of expression of cell surface activation markers, for example, by flow cytometry or fluorescent microscopy, or cytolytic assays, or by measuring the secretion of cytokines or chemokines or other substances secreted by activated immune cells, or by measuring activation-induced changes in immune cell gene expression; for example by real time polymerase chain reaction or gene expression arrays. The amount of each component of the immunological formulation necessary to provide an immunologically-effective amount is readily determined by one of ordinary skill in the art, e.g., by preparing a series of immunological formulations of the invention with varying concentrations of PAMP innate immune activator and inulin particles (or other equivalent anti-inflammatory component) then adding these formulations to cultures of immune cells and assaying immune cell activation by means known to one skilled in the art, including the assays detailed herein. Similarly, the amount of each component necessary to provide enhancement of the immune response to a vaccine antigen can be readily determined by one of ordinary skill in the art, for example, by preparing a series of immunological formulations of the invention with varying concentrations of PAMP innate immune activator and inulin particles (or other equivalent anti-inflammatory component) plus a vaccine antigen and administering the vaccine together with inulin particles (or other equivalent anti-inflammatory component), to suitable laboratory animals (e.g., mice or guinea pigs), and then assaying the resulting antigen-specific immune response by measurement of antigen-specific serum or mucosal antibody titres, antigen-induced swelling in the skin (DTH), or antigen-stimulated T-cell proliferation or cytokine production.

PAMP innate immune activators used in the invention can be effective in any animal, preferably a mammal, and most preferably a human. Different PAMP innate immune activators can cause optimal immune stimulation depending on the species. Thus a PAMP immune activator such as a specific CpG ODN that provides optimal stimulation in humans by binding to human TLR9 may not cause optimal stimulation in a mouse expressing mouse TLR9, or vice versa. One of ordinary skill in the art can identify the optimal PAMP innate immune activators useful for a particular species of interest using routine immune assays described herein or known in the art.

The aqueous portion of the compositions and substances of the aspects of the present invention may be buffered in iso-osmotic saline. Because the compositions and substances may be intended for parenteral or mucosal administration, it may be appropriate to formulate these solutions so that the tonicity is essentially the same as normal physiological fluids in order to prevent post-administration swelling or rapid absorption of the composition due to differential ion concentrations between the composition and physiological fluids. It may also be appropriate to buffer the saline in order to maintain a pH compatible with normal physiological conditions. For example, the buffered pH may suitably be in the range of 4 to 10, in the range 5 to 9, in the range 6 to 8.5, or in the range 7 to 8.5. Also, in certain instances, it may be necessary to maintain the pH at a particular level in order to insure the stability of certain composition components, such as the inulin particles, PAMP or the protein antigens in a formulation. Any physiologically acceptable buffer may be used herein, but it has been found that it is most convenient to use bicarbonate buffered saline (1%) at a pH of between 6 and 8.5. Suitable preservatives include benzalkonium chloride (0.003-0.03% w/v); chlorobutanol (0.3-0.9% w/v); parabens (0.01-0.25% w/v) and thimerosal (0.004-0.02% w/v).

The invention in other aspects includes a method of modulating including inducing or suppressing a non-antigen-specific immune response. In one aspect, the present invention provides a method for enhancing protection against a pathogen, wherein said method comprises administering to a subject a therapeutically effective amount of the compositions or substances of the invention. This may provide temporary protection against various pathogens including viruses, bacteria, parasites, fungi and protozoa, for treatment of cancer, or prevention or treatment of autoimmune disease, asthma or allergy. The method involves the steps of administering to a subject the immunological composition of the present invention in an immunologically-effective amount. For longer-term protection, the immunological composition may be administered more than once.

In various embodiments, the immunological composition of the invention is intended for treatment or prevention of a variety of diseases. Thus, in various embodiments, the immunological composition is provided in an amount effective to treat or prevent an infectious disease, a cancer, or an allergy. Accordingly, the methods provided herein can be used on a subject that has or is at risk of developing an infectious disease and therefore the method is a method for treating or preventing the infectious disease. The methods can also be used on a subject that has or is at risk of developing asthma and the method is a method of treating or preventing asthma in the subject. The method can also be used on a subject that has or is at risk of developing allergy and the method is a method of treating or preventing allergy. The method can also be used on a subject that has or is at risk of developing a cancer and the method is a method of treating or preventing the cancer.

The compositions and substances used in the aspects of the present invention may be used in some embodiments to alter the type or magnitude of the immune response including in one option to a co-administered antigen. Accordingly, it is proposed that the compositions and substances can be widely used as a vaccine adjuvant, for example, by combining it/them with one or more relevant antigens to form a prophylactic or therapeutic vaccine. Thus, in an important embodiment, the compositions and substances of the aspects of the present invention further comprise a vaccine antigen.

Alternatively, the subject to be treated is further administered a vaccine antigen at the same time as or following the administration of an immunologically effective amount of the immunological composition. The antigen may be selected from the group consisting of a microbial antigen, a self-antigen, a cancer antigen, and an allergen, but it is not so limited. In one embodiment, the microbial antigen is selected from the group consisting of a bacterial antigen, a viral antigen, a fungal antigen and a parasitic antigen. In another embodiment, the antigen may be a peptide antigen. In another embodiment, the antigen is encoded by a nucleic acid vector. In another embodiment, the composition further comprises a cytokine, or the subject is further administered a cytokine.

The term "antigen" refers to any substance, usually a protein or glycoprotein, lipoprotein, saccharide, polysaccharide or lipopolysaccharide, which upon administration stimulates the formation of specific antibodies or memory T cells. An antigen can stimulate the proliferation of T-lymphocytes with receptors for the antigen, and can react with the lymphocytes to initiate the series of responses designated cell-mediated immunity.

Suitable antigens for use in this invention include substances from microbes (bacteria, fungi, protozoa, or viruses) or endogenous substances against which a specific immune response can be generated. Antigens may be prepared from inactivated organisms or may be generated by recombinant protein technology or directly synthesized. For the purposes of this description, an antigen is defined as any protein, carbohydrate, lipid, nucleic acid, or mixture of these, or a plurality of these, to which an immune response is desired. The term antigen as used herein also includes combinations of haptens with a carrier. A hapten is a portion of an antigenic molecule or antigenic complex that determines its immunological specificity, but is not sufficient to stimulate an immune response in the absence of a carrier. Commonly, a hapten is a relatively small peptide or polysaccharide and may be a fragment of a naturally occurring antigen. A hapten will react specifically in vivo and in vitro with homologous antibodies or T-lymphocytes. Haptens are typically attached to a large carrier molecule such as tetanus toxoid or keyhole limpet hemocyanin (KLH) by either covalent or non-covalent binding before formulation as a vaccine.

Antigens can be used in vaccines to either treat or prevent a disease. They can also be used to generate specific immune substances, such as antibodies, which can be used in diagnostic tests or kits. The subjects of an antigen-containing vaccine are typically vertebrates, preferably a mammal, more preferably a human. It is important to note that it is not always necessary that the antigen be identified in molecular terms. For example, immune responses to tumours can be generated without knowing either in advance or post-hoc which molecules the immune response is directed against. In these cases, the term antigen refers to the substance or substances, known or not known, toward which a specific immune response is directed. The specificity of the immune response provides an operational definition of an antigen, such that immunity generated against one type of tumour may be specific for that tumour type but not another tumour type.

In one important embodiment of the aspects of the present invention, the encoded antigen may be derived from a virus such as *influenza*, including inactivated *influenza* virus or *influenza* haemagglutinin, neuraminidase or M2 protein or other components of the *influenza* virus. Examples of other RNA viruses that are antigens in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the genus *Rhinovirus*, the genus *Apthovirus* (Foot and Mouth disease; the family Calciviridae, including Vesicular exanthema of swine virus, San Miguel sea lion virus, Feline picomavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (*Influenza* virus type A, many human subtypes); Swine *influenza* virus, and Avian and Equine *Influenza* viruses; *influenza* type B (many human subtypes), and *influenza* type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (*Influenza* virus type A, many human subtypes); Swine *influenza* virus, and Avian and Equine *Influenza* viruses; *influenza* type B (many human subtypes), and *influenza* type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesvirises (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A, B, C, D, E and ungrouped; simian adenoviruses (at least 23 serotypes), infectious *canine* hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (*polyomavirus*, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine *parvovirus, canine* parvovlrus, Aleutian mink disease virus, etc). DNA viruses also include Kuru and Creutzfeldt-Jacob disease viruses and chronic infectious neuropathic agents (CHINA virus).

Each of the foregoing lists is illustrative, and is not intended to be limiting.

Other examples of antigens suitable for the invention include, but are not limited to, infectious disease antigens for which a protective immune response may be desired including the human immunogenicity virus (HIV) antigens gag, env, pol, tat, rev, nef, reverse transcriptase, and other HIV components or a part thereof, the E6 and E7 proteins from human papilloma virus, the EBNA1 antigen from herpes simplex virus, hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; *influenza* viral antigens such as hemagglutinin, neuraminidase, nucleoprotein, M2, and other *influenza* viral components; measles viral antigens such as the measles virus fusion protein and other measles virus components; rubella viral antigens such as proteins E1 and E2 and other rubella virus components; rotaviral antigens such as VP7sc and other rotaviral components; cytomegalovirus antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS 1, NS 1-NS2A; rabies viral antigens such as rabies glycoprotein, rabies nucleoprotein and other rabies viral antigen components; West Nile virus prM and E proteins; and Ebola envelope protein. See Fundamental Virology, Second Edition, eds. Knipe, D. M. and, Howley P. M. (Lippincott Williams & Wilkins, New York, 2001) for additional examples of viral antigens. In addition, bacterial antigens are also disclosed. Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; Staphylococcal bacterial antigens such as IsdA, IsdB, SdrD, and SdrE; gram-negative bacilli bacterial antigens such as lipopolysaccharides, flagellin, and other gram-negative bacterial antigen components; *Mycobacterium tuberculosis* bacterial antigens such as mycolic acid, heat shock protein 65 (HSP65), the 30 kDa major secreted protein, antigen 85A, ESAT-6, and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus influenza* bacterial antigens such as capsular polysaccharides and other *haemophilus influenza* bacterial antigen components; anthrax bacterial antigens such as anthrax protective antigen, anthrax lethal factor, and other anthrax bacterial antigen components; the F1 and V proteins from *Yersinia pestis*; rickettsiae bacterial antigens such as romps and other rickettsiae bacterial antigen components. Also included with the bacterial antigens described herein are any other bacterial, mycobacterial, mycoplasmal, rickettsial, or chlamydial antigens. Examples of protozoa and other parasitic antigens include, but are not limited to, *Plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; *toxoplasma* antigens such as SAG-1, p30 and other *toxoplasma* antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components. Examples of fungal antigens include, but are not limited to, antigens from *Candida* species, *Aspergillus* species, *Blastomyces* species, *Histoplasma* species, *Coccidiodomycosis* species, *Malassezia furfur* and other species, *Exophiala werneckii* and other species, *Piedraia hortai* and other species, *Trichosporum beigelii* and other species, *Microsporum* species, *Trichophyton* species, *Epidermophyton* species, *Sporothrix schenckii* and other species, *Fonsecaea pedrosoi* and other species, *Wangiella dermatitidis* and other species, *Pseudallescheria boydii* and other species, *Madurella grisea* and other species, *Rhizopus* species, *Absidia* species, and *Mucor* species. Examples of prion disease antigens include PrP, beta-amyloid, and other prion-associated proteins.

In addition to the use of the compositions and substances of the aspects of the present invention to induce an antigen specific immune response in humans, the methods of the preferred embodiments are particularly well suited for treatment of horses and other animals. The methods of the invention can be used to protect against infection in livestock, including cows, camels, horses, pigs, sheep, and goats. Horses are susceptible to flaviviruses including Japanese encephalitis and West Nile virus. In a preferred embodiment, the immunological composition of the invention can be administered to horses together with inactivated Japanese encephalitis virus antigen to protect them against Japanese encephalitis and related flaviviruses.

In addition to the infectious and parasitic agents mentioned above, another area for desirable enhanced immunogenicity to a non-infectious agent is in the area of cancer, in which cells expressing cancer antigens are desirably eliminated from the body. A "cancer antigen" as used herein is a compound, such as a peptide or protein, present in a tumour or cancer cell and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumour or cancer. Such antigens can be isolated or prepared by recombinant DNA expression technology or by any other means known in the art. In one embodiment, the cancer is selected from the group consisting of biliary tract cancer; bone cancer; brain and CNS cancer; breast cancer; cervical cancer; choriocarcinoma; colon cancer; connective tissue cancer; endometrial cancer; esophageal cancer; eye cancer; gastric cancer; Hodgkin's lymphoma; intraepithelial neoplasms; larynx cancer; lymphomas; liver cancer; lung cancer (e.g. small cell and non-small cell); melanoma: neuroblastomas; oral cavity cancer, ovarian cancer; pancreas cancer; prostate cancer; rectal cancer; sarcomas; skin cancer; testicular cancer; thyroid cancer; and renal cancer. Cancer antigens which can be used in the compositions and methods of the invention include, but are not limited to, prostate specific antigen (PSA), breast, ovarian, testicular, melanoma, telomerase; multidrug resistance proteins such as P-glycoprotein; MAGE-1, alpha fetoprotein, carcinoembryonic antigen, mutant p53, *papillomavirus* antigens, gangliosides or other carbohydrate-containing components of melanoma or other cancer cells. It is contemplated by the invention that antigens from any type of cancer cell can be used in the compositions and methods described herein. The antigen may be a cancer cell, or immunogenic materials isolated from a cancer cell, such as membrane proteins.

Included are survivin and telomerase universal antigens and the MAGE family of cancer testis antigens.

In another preferred embodiment, the compositions and methods of the invention include antigens involved in autoimmunity that can be used to induce immune tolerance. Such antigens include, but are not limited to, myelin basic protein, myelin oligodendrocyte glycoprotein and proteolipid protein of multiple sclerosis, CII collagen protein of rheumatoid arthritis, glutamic acid decarboxylase, inulin and tyrosine phosphatase proteins of type 1 diabetes mellitus, gliadin protein of celiac disease, In another preferred embodiment, the compositions, substances and methods of the aspects of the present invention can be used with antigens known as "allergens" involved in allergy to induce tolerance and suppress allergen-specific IgE. An "allergen" is any substance that can induce an allergic or asthmatic response in a susceptible subject. Allergens include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtuse*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *PArrhenatherum elatius*); *Agrostis* (e.g. *Agrostis alba*); *Phleum* (e.g. *Phleum preatense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). Most preferred for the invention is an insect venom allergen.

In another preferred embodiment, the compositions, substances and methods of the aspects of the present invention can be used to immunise against antigens involved in asthma. Such antigens include, but are not limited to IgE and histamine.

The term "treatment" as used herein covers any treatment of a disease in a bird, fish or mammal, particularly a human, and includes:
(i) preventing the disease from occurring in a subject which may be predisposed to the disease but has not yet been diagnosed as having it;
(ii) inhibiting the disease, i.e., slowing or arresting its development; or
(iii) relieving the disease, i.e., causing regression of the disease. (It should be noted that vaccination may effect regression of a disease where the disease persists due to ineffective antigen recognition by the subject's immune system, where the vaccine effectively presents antigen.)

The term "optionally" means that the subsequently described event or circumstances may or may not occur, and that the description includes instances where said event or circumstances occurs and instances in which it does not occur.

The term "modulation of the immune response" is to be understood as the induction of any induced change in an immune cell, which can be measured in a manner known to those of ordinary skill in the art. Preferably, the measured parameter to indicate a change in the behaviour or function of immune cells will be selected from the group of a change in gene expression, protein expression, cell morphology, differentiation, cell division, cell surface protein expression, chemotaxis, phagocytosis, exocytosis, autophagy, chemokine secretion, cytokine secretion and apoptosis.

In a further embodiment of the invention, the co-administration of an inulin particle (or other equivalent anti-inflammatory component) with a PAMP innate immune activator allows dose-sparing of the PAMP innate immune activator. Hence in the presence of a inulin particle (or other equivalent anti-inflammatory component), a lower dose of a PAMP innate immune activator can be used to obtain the same level of immune activation. Given the different actions of a inulin particle (or other equivalent anti-inflammatory component) and a PAMP innate immune activator, the dose-sparing effect of inulin particles (or other equivalent anti-inflammatory component) allows a lower dose of PAMP immune activator to be used to achieve a desired immune response or adjuvant effect and thereby provides a means to reduce any dose-related side effects or toxicity of the PAMP, innate immune activator, while still achieving the desired immune outcome. As dose-related toxicity from excess PAMP innate immune activation and inflammation are the main dose-limiting side effects of PAMP innate immune activators, the invention provides a novel means to reduce the dose-related side effects of PAMP innate immune activators.

The composition and substances of the aspects of the present invention may optionally be administered in its/their separate components simultaneously or sequentially but preferably the inulin particle component (or other equivalent anti-inflammatory component) is administered together with or prior to the antigen rather than following the antigen. When the components of the composition or substances of the aspects of the present invention are administered simultaneously they can be administered in the same or separate formulations, and in the latter case at the same or separate injection sites, and at the same time as the vaccine antigen. The PAMP innate immune activator component can be administered before, after, or simultaneously with the inulin particles (or other equivalent anti-inflammatory component) and the antigen component. For instance, the PAMP innate immune activator component may be administered prior to or after the administration of the inulin particle (or other equivalent anti-inflammatory component) component together with a priming dose of antigen. The boost dose of antigen may subsequently be administered with either or both of the PAMP innate immune activator and the inulin particle component (or other equivalent anti-inflammatory component). A "prime dose" is the first dose of antigen administered to the subject. A "boost dose" is a second, third, or subsequent dose of antigen administered to a subject that has already been exposed to the antigen. Where the components are administered sequentially, the separation in time between the administrations of the components may be a matter of minutes or it may be longer. The separation in time is preferably less than 7 days, 3 days, or 2 days and most preferably less than 1 day.

The compositions or substances of the aspects of the present invention may be used to enhance a vaccine response in association with use of a DNA vaccine. In a preferred embodiment, the compositions or substances of the aspects of the present invention with a protein or other physical antigen is/are administered as a boost dose following one or more prime doses of an effective immunogenic amount of a DNA vaccine encoding one or more antigens. In a further embodiment, the composition or substances of the aspects of the present invention is/are administered with a protein or other physical antigen at the same time as a DNA vaccine encoding one or more antigens is administered either at a different injection site or mixed together and administered at the same injection site.

The compositions or substances of the aspects of the present invention with or without the addition of a physical antigen may also be administered together with a vector encoding an antigen. In its broadest sense, a "vector" is any vehicle capable of facilitating the transfer to and expression by the infected cell of an encoded or enclosed antigen. In general, the vectors useful in the invention include, but are not limited to, plasmids, phages, viruses, and other vehicles derived from viral or bacterial sources that have been manipulated by the insertion or incorporation of the antigen nucleic acid sequences. Viral vectors are a preferred type of vector and include, but are not limited to, nucleic acid sequences from the following viruses: retrovirus, such as moloney murine leukemia virus, harvey murine sarcoma virus, murine mammary tumour virus, and rouse sarcoma virus; adenovirus, *adeno*-associated virus; SV40-type viruses; polyoma viruses; Epstein-Barr viruses; papilloma viruses; herpes virus; vaccinia virus; polio virus; retrovirus; lentivirus and sendai virus. It is known in the art how to readily employ other vectors in a similar fashion to deliver antigens to cells. See e.g., Sanbrook et al., "Molecular Cloning: A Laboratory Manual," Second Edition, Cold Spring Harbor Laboratory Press, 1989

One or more of the preparations of the compositions substances of the aspects of the present invention may include an antigen-binding carrier material or allergen-binding carrier material. The antigen-binding carrier material or allergen-binding carrier material may comprise, for example, one or more metal salts such as those of the group consisting of aluminium hydroxide, aluminium phosphate, aluminium sulphate, calcium phosphate, calcium sulphate, ferrous and ferric phosphate, ferrous and ferric sulphate, chromium phosphate and chromium sulphate. Other suitable antigen-binding carrier materials and allergen-binding carrier materials include proteins, lipids and carbohydrates (e.g. heparin, dextran and cellulose derivatives), and organic bases such as chitin (poly N-acetylglucosamine) and deacetylated derivatives thereof, as know to those of ordinary skill in the art.

In an important embodiment, the PAMP innate immune activator in the immunological composition is physically bound to the inulin particle (or other equivalent anti-inflammatory component) or to the antigen-binding carrier material incorporated with the inulin particle (or other equivalent anti-inflammatory component). In a preferred embodiment, the PAMP innate immune activator is bound to the inulin particle (or other equivalent anti-inflammatory component) by a bond selected from the group consisting of covalent, hydrostatic, and electrostatic bonds. Alternatively, the PAMP innate immune activator can be sterically trapped inside the inulin particle (or other equivalent anti-inflammatory component). In a further embodiment, a linker sequence can be used to join the PAMP innate immune activator to the inulin particle (or other equivalent anti-inflammatory component).

Further, where the compositions or substances of the aspect of the present invention include an antigen-binding material, preferably the inulin particles (or other equivalent anti-inflammatory component) are combined with or bound to the antigen-binding carrier material. Co-crystals of inulin particles and an antigen-binding carrier material may be prepared by, for example, a method comprising:
(a) preparing a suspension of the inulin particles;
(b) heating the suspension until the inulin particles dissolve;
(c) adding to said solution an amount of an antigen-binding carrier material;
(d) re-precipitating the inulin particles from said suspension; and
(e) isolating formed particles comprising inulin particles and one or more antigen-binding carrier material In a development of this work, the inulin particles can be formulated with an antigen-binding carrier material, in particular, aluminium hydroxide or aluminium phosphate (collectively referred to as "alum") gel. Alum gel has been widely used as an adjuvant in vaccines wherein it is known to induce a strong antibody (Th2) immune response but only a poor cellular (Th1) immune response. Thus, it has been found possible to form co-crystallised particles of gIN, dIN or eIN together with aluminium salts (for example aluminium hydroxide or aluminium phosphate), to form, respectively, a gIN/alum preparation (also referred to as "Algammulin") (see WO 90/01949, WO 2006/024100), a dIN/alum preparation (also referred to as "Aldeltin") or an eIN/alum hydroxide preparation (also referred to as "Alepsilin"). While in vivo studies have shown that vaccines containing complexes of inulin particles and aluminium salts are well tolerated, their ability to increase antibody responses to co-administered antigens over and above the inulin particle or alum adjuvant formulation alone are generally modest and additive rather than synergistic, and like alum adjuvants alone, the formulation of inulin with alum biases the resultant immune response towards a Th2 rather than a Th1 response. This may not be desirable for particular vaccines where it is sought to induce Th1 immunity to a co-administered antigen. In particular, without wishing to be restricted by theory, adjuvants that enhance Th1 immunity tend to inhibit the magnitude of a Th2 response and vice versa, via a complex array of feedback pathways involving factors such as the Th1 cytokine IFN-γ, which inhibits Th2 responses, whereas the Th2 cytokines, IL-4 and IL-10, inhibit Th1 responses. A bias towards a Th2 response may be undesirable if it means that less of a Th1 response can be achieved and vice versa. In one embodiment of this invention, it has been found that the Th2 bias seen when inulin is co-crystallised with aluminium salts, as in the case of Algammulin, Aldeltin or Alepsilin, or phosgammulin, phosdeltin or phosepsilin is reduced or no longer evident when the inulin particle-alum particles are combined with a PAMP innate immune activator. Conversely, the strong Th1 bias often observed with some innate immune activators alone, for example with TLR9 agonists, is reduced or no longer evident when TLR9 agonists are formulated with inulin particles with or without an antigen-binding alum. In the presence of inulin particles, both Th1 and Th2 immune responses develop in parallel, resulting in an improved immune response against a co-administered antigen not achievable with use of the individual components alone. The inulin particle (or other equivalent anti-inflammatory component) combined with the antigen-binding carrier material may comprise a relative amount by weight of the inulin (or other equivalent anti-inflammatory component) to the antigen-binding carrier material in the range of 1:20 to 200:1, such as 1:5 to 50:1, or 1:2 to 20:1.

In another embodiment, the compositions or substances according to the aspects of the present invention may further comprise a therapeutic agent selected from the group consisting of an anti-microbial agent, an anti-cancer agent, and an allergy or asthma medicament, or the subject is further administered a therapeutic agent selected from the same group. In a related embodiment, the anti-microbial agent is selected from the group consisting of an anti-bacterial agent, an anti-viral agent, an anti-fungal agent, and an anti-parasite agent.

In a related embodiment, the anti-cancer agent included with the immunological composition is selected from the group consisting of a chemotherapeutic agent, a cancer vaccine, and an immunotherapeutic agent, In a related embodiment, the allergy or asthma medicament included with the immunological composition is selected from the group consisting of PDE-4 inhibitor, bronchodilator/beta-2 agonist, K+ channel opener, VLA-4 antagonist, neurokin antagonist, TXA2 synthesis inhibitor, xanthanine, arachidonic acid antagonist, 5 lipoxygenase inhibitor, thromboxin A2 receptor antagonist, thromboxane A2 antagonist, inhibitor of 5-lipox activation protein, and protease inhibitor.

The compositions or substances of the aspects of the present invention may be formulated for parenteral administration or may be formulated in a sustained release device. The sustained release device may be a microparticle, a matrix or an implantable pump, but it is not so limited.

In another embodiment, the compositions and substances of the aspects of the present invention is/are formulated for delivery to a mucosal surface. In related embodiments, the compositions and substances of the aspects of the present invention is/are provided in an amount effective to stimulate a mucosal immune response. The mucosal surface may be selected from the group consisting of an oral, nasal, rectal, vaginal, and ocular surface, but is not so limited. In one embodiment, the compositions and substances of the aspects of the present invention is/are formulated for oral administration. The compositions and substances of the aspects of the present invention may also be formulated as a nutritional supplement in a related embodiment, the nutritional supplement is formulated as a capsule, a pill, or a sublingual tablet. In another embodiment, the immunological composition is formulated for local administration.

In embodiments relating to the treatment of a subject, the method or use may further comprise isolating an immune cell from the subject, contacting the immune cell with an immunologically-effective amount of the compositions and substances of the aspects of the present invention to thereby produce an ex vivo activated immune cell; and optionally then re-administering the activated immune cell to the subject. In one embodiment, the immune cell is a monocyte and in another embodiment the immune cell is a dendritic cell. In another embodiment, the method or use may further comprise contacting the immune cell with an antigen in the presence of, before or after the addition of an immunologically-effective amount of the compositions or substances of the aspects of the present invention In still another aspect, the invention provides a method for identifying an optimal immunological composition by measuring a control level of activation of an immune cell population contacted with a composition or substances of the aspects of the present invention, then comparing this with the level of activation of an immune cell population contacted with a test composition, wherein a test level that is equal to or above the control level is indicative of a suitable immunological composition.

The immune response may comprise immune activation as manifest by changes in gene expression or protein production such as induction of cytokine or chemokine production or secretion, changes in phenotype, proliferative or survival capacity or modulation of immune effector properties. The immune response may further comprise induction, enhancement or modulation of an adaptive immune response with induction of antibody production or induction of a T-cell effector or memory response against an endogenous or exogenous antigen.

In a further aspect, the present invention provides a method for modulating an immune response, wherein said method comprises administering to a subject a therapeutically effective amount of the compositions or substances of the aspects of the present invention.

As used herein, the term "effective amount" refers to a non-toxic but sufficient amount of the compositions and substances of the aspects of the present invention to provide the desired effect. The exact amount required will vary from subject to subject depending on factors such as the species being treated, the age and general condition of the subject, the severity of the condition being treated, the particular composition or substances of the aspects of the present invention being administered and the mode of administration. Thus, it is not possible to specify an exact "effective amount". However, for any given case, an appropriate "effective amount" may be routinely determined by persons of ordinary skill in the art.

The invention further provides a method of modulating the patterns of cytokines produced in response to a vaccine. The term "modulate" envisions the suppression of expression of a particular cytokine when lower levels are desired, or augmentation of the expression of a particular cytokine when higher levels are desired. Modulation of a particular cytokine can occur locally or systemically. PAMP innate immune activators so used as vaccine adjuvants can directly activate macrophages and dendritic cells to secrete cytokines such as TNF-α and IL-1. Cytokine profiles induced by PAMPs innate immune activators determine T-cell regulatory and effector functions in immune responses and may also contribute to vaccine adverse reactions. In general, PAMP innate immune activators induce cytokines associated with inflammation and fever including TNF and IL-1, but may also induce suppressive cytokines such as IL-10, that provide inhibitory feedback and may thereby limit or inhibit the adaptive immune response to a co-administered antigen. The compositions and substances of the aspects of the present invention is/are able to modulate the cytokines induced by a PAMP innate immune activator, and thereby lead to a more favourable immune response.

In other aspects the invention includes a method for preventing in a subject excess polarisation of the immune response otherwise caused by administering to the subject a combination of an antigen and a PAMP innate immune activator such as a TLR agonist. It has been previously shown that the combination of a PAMP innate immune activator such as CpG ODN, a TLR9 agonist, resulted in a Th1 bias and suppression of the Th2 arm of the response. It was thus a surprising finding that when inulin particles are combined with a Th1-biasing PAMP innate immune activator such as CpG ODN, it is possible to maintain a strong Th2 response while at the same time also inducing a Th1 immune response to a co-administered antigen, thereby resulting in a synergistic increase in both the Th2 and Th1 response to the antigen, to an extent that the components in the absence of the inulin particles could not produce.

The compositions and substances of the aspects of the present invention may be formulated in a pharmaceutically acceptable carrier, diluent or excipient in a form suitable for injection, or a form suitable for oral, rectal, vaginal, topical, nasal, transdermal or ocular administration. The compositions and substances of the aspects of the present invention may also comprise a further active component such as, for example, a vaccinating antigen (including recombinant antigens), an antigenic peptide sequence, or an immunoglobulin. Alternatively, the active component may be a macrophage stimulator, a polynucleotide molecule (e.g. encoding a vaccinating agent) or a recombinant viral vector.

The components of the vaccine and adjuvant compositions of the invention may be obtained through commercial sources, or may be prepared by one of ordinary skill in the art. The inulin particle formulations may be prepared by the processes disclosed in U.S. Provisional Patent Application No. 61/243,975 and international Patent Applications PCT/AU86/00311 (WO 87/02679), PCT/AU89/00349 (WO 90/01949) and PCT/AU2005/001328 (WO 2006/024100) or may be obtained commercially from Vaxine Pty Ltd, Adelaide, Australia. PAMP innate immune activators for use in the invention may be obtained commercially or made using methods well known in the art. For example, synthetic triacylated lipoprotein, Pam3CSK4 (0.25 µg/mouse), heat killed *Listeria monocytogenes* (2.5×10e7 cells/mouse), lipoarabinomannan from *M. smegmatis* (0.25 µg/mouse), LPS-PG ultrapure lipopolysaccharide from *P. gingivalis* (2.5 µg/mouse), standard lipoteichoic acids (LTA-SA) from *S. aureus* (2 µg/mouse), peptidoglycan from *Staphylococcus aureus* (PGN-SA) (2 µg/mouse), synthetic diacylated lipoprotein (0.25 µg/mouse), zymosan (1 mg/mouse), and CpG2006 (SEQ ID NO:1) (20 µg/mouse) as used in the current invention were all purchased from Invivogen, San Diego, USA. Synthetic CpG ODN synthesized with a native or modified phosphorothioate backbone was purchased from Geneworks, Australia and can be obtained from other commercial suppliers. MPLA may be purchased from Sigma, USA or Invivogen, San Diego, USA. Plasmid DNA may also be prepared using methods well known in the art, for example using the Quiagen procedure (Quiagen Inc, USA), followed by DNA purification using known methods. The inactivated or recombinant antigens used for immunization can be obtained through commercial chemical or protein suppliers such as Sigma, USA or may be prepared using methods well known in the art.

Biological activity of a vaccine may be assayed using standard laboratory techniques, e.g., by vaccinating a standard laboratory animal (e.g., a mouse or guinea pig) with a standard antigen (e.g., tetanus toxoid) using a test immunological formulation. After allowance of time for boosting the vaccination, and time for immunization to occur, the animal is bled or the spleen removed and the response to the vaccine measured. The response may be quantified by any measure accepted in the art for measuring immune responses, e.g., serum, saliva, vagina, stool antibody titer against the standard antigen (for measurement of humoral immunity) and T-cell proliferation, cytokine ELISPOT or cytokine ELISA assay (for measurement of T-cell immunity).

It will be apparent to one of ordinary skill in the art that the precise amounts of protein antigen and immunological composition needed to produce a given effect will vary with the particular compounds and antigens, and with the size, age, species, and condition of the subject to be treated. Thus, it is impossible to state exactly the amounts needed. However, these amounts can easily be determined using methods known to those of ordinary skill in the art. In general, one or more vaccinations with the desired antigen are initially administered by intramuscular, subcutaneous or intradermal injection to prime the immune response. The vaccination is then "boosted" after a delay (usually from 1-12 months, for example, 6 months) using the immunological composition of the invention preferably by administering on one or more occasions the antigen combined with the immunological composition by parenteral injection for systemic immune boosting. Generally the antigen dose used for an adult human will be in the range of 0.001-0.1 mg and most commonly 0.001-0.1 mg, or 0.005-0.05 mg per dose.

Generally, in the range of 0.1 to 5.0 mL of a vaccine is administered in the practice of the invention, and preferably in the range of 0.1 to 1 ml for a human subject.

The compositions and substances according to the aspects of the present invention is/are preferably administered by intramuscular or intradermal injection, or other parenteral means, or by balistic application to the epidermis. They may also be administered by intranasal application, inhalation, topically, intravenously, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science 249:1527-1533, 1990.

The immunological compositions are preferably prepared and administered in dose units. Liquid dose units are vials or ampoules for injection or other parenteral administration. Solid dose units are tablets, capsules and suppositories. The administration of a given dose can be carried out both by single administration in the form of an individual dose unit or else several smaller dose units. Multiple administration of doses at specific intervals of weeks or months apart is usual for boosting antigen-specific immune responses.

The compositions and substances of the aspects of the present invention, or antigens useful in the invention, may be delivered in mixtures of more than two components. A mixture may consist of the immunological composition including one or more types of inulin particles (or other equivalent anti-inflammatory component) together with one or more PAMP innate immune activators and one or more antigens.

In order that the nature of the present invention may be more clearly understood, preferred forms thereof will now be described with reference to the following non-limiting examples.

EXAMPLES

The use of inulin particles in vaccines either alone or in combination with other immune activators was evaluated.

Recombinant hepatitis B virus surface antigen (HBsAg) and *influenza* virus antigen were used as exemplary model systems in the examples set forth below.

Materials and Methods

Example 1: Preparation of Adjuvant Compositions

Inulin particle formulations referred to in the following examples were prepared as described below.

Gammulin (Gamma inulin; gIN), Algammulin (AG) and Phosgammulin (PG): Gamma inulin (gIN) and Algammulin were prepared as previously described in PCT/AU86/00311 (WO 87/02679) titled "Immunotherapeutic treatment", and PCT/AU89/00349 (WO 90/01949) titled "Gamma inulin compositions". To produce Phosgammulin (PG), a 5% suspension of gIN in water was first dissolved by heating at 80-85° C. then mixed with a fine suspension of aluminium phosphate gel (Adju-Phos™ Aluminium Phosphate Gel Adjuvant 0.44%, BrenntagBiosector, Frederickssund, Denmark) in a proportion to give an inulin:Adju-Phos™ weight/weight ratio of between 2 and 200. The suspension was then crystallized at 5° C., then converted to the gamma form (1 hour at 45°) to yield Phosgammulin hybrid particles, and washed and formulated as appropriate.

Deltin (Delta inulin; dIN): Deltin (dIN) was prepared from gIN as previously described in WO 2006/024100. Briefly, a standard formulation of gIN in water (200 ml at 50 mg/ml) was incubated for 1 hour in a water bath at 55° C., which was then raised to 60° C. for 30 min. The particles were then centrifuged, resuspended in water at 55° C., re-incubated at 55° C. and washed again in the same manner, before being finally resuspended in 50 ml cold water. This treatment is sufficient to remove much of the inulin present in the alpha and gamma forms. A sample of the dIN-enriched suspension dissolved completely at 80-85° C. The refractive index indicated a concentration of 48 mg/ml. The Deltin suspension used in these experiments had a concentration of 5% weight/volume of water.

Phosdeltin (dIN/aluminium phosphate preparation (PD)): To produce Phosdeltin (PD), a 5% suspension of Deltin as described above was first dissolved in water by heating at 80-85° C. then mixed with a fine suspension of aluminium phosphate gel (Adju-Phos™ Aluminium Phosphate Gel Adjuvant 0.44%, BrenntagBiosector, Frederickssund, Denmark) in a proportion to give an dIN:Adju-Phosm weight/weight ratio of between 2 and 200. The suspension was then crystallized at 5° C., then converted to gIN (1 hr at 45°) then to dIN (1 hr at 55° C.) to yield Phosdeltin hybrid particles, and washed and formulated as appropriate.

Aldeltin (dIN/aluminium hydroxide preparation): To produce Aldeltin (AD), the same procedure was followed as above for Phosdeltin except that a fine suspension of aluminium hydroxide gel (Alhydrogel™ Aluminium Hydroxide Gel Adjuvant, Al (calc) 3.0%, BrenntagBiosector, Frederickssund, Denmark) was used instead of aluminium phosphate gel. In brief, a 5% suspension of Deltinin water as described above was first dissolved by heating at 80-85° C. then mixed with a fine suspension of Alhydrogel™ in a proportion to give an dIN:Alhydroge™ weight/weight ratio of between 2 and 200. The suspension was then crystallized at 5° C., then converted to gIN (1 hr at 45°) and then to dIN (1 hr at 55° C.) to yield Aldeltin hybrid particles, and washed and formulated as appropriate.

Epsilin (eIN): Epsilin was prepared from dIN as described in PCT/AU2010/001221 titled "A novel epsilon polymorphic form of inulin and compositions comprising same". In brief, EI was prepared by heating a concentrated suspension of greater than 50 mg/ml of dIN at 60° C. for one hour.

Phosepsilin (PE): To produce Phosepsilin (PE), a 5% suspension of eINin water as described above was first dissolved by heating at 80-85° C. then mixed with a fine suspension of aluminium phosphate gel (Adju-Phos™ Aluminium Phosphate Gel Adjuvant 0.44%, BrenntagBiosector, Frederickssund, Denmark) in a proportion to give an eIN:Adju-Phos™ weight/weight ratio of between 2 and 200. The suspension was then crystallized at 5° C., then converted to gIN (1 hr at 45°) then to the dIN form (1 hr at 55° C.) then to the eIN form to yield Phosepsilin hybrid particles, and washed and formulated as appropriate. Alepsilin (AE) was similarly made by substituting Alhydrogel™ Instead of Adju-Phos™ in the above process for making Phosepsilin.

PGmix, PDmix and PEmix: Phosdeltin (dIN/aluminium phosphate) and dIN formulations, as described above, were admixed to form a mixed suspension of particles some containing pure inulin and others containing inulin with aluminium phosphate (PDmix). For the experiments described herein, the PDmix Phosdeltin:Deltin combination adjuvant was prepared in various ratios ranging from 1:1 to 1:36 weight for weight of inulin content of inulin-alum amalgam particles and inulin particles, respectively, hereinafter referred to as PDmix1:1 to PDmix1:36) This enabled the amount of aluminium phosphate containing particles to be varied relative to the number of non-aluminium salt containing dIN particles. PGmix and PEmix were prepared in the same manner. The ratio of Phosdeltin to Deltin particles is expressed as x:y PD:D). This means that x amount of PD based on inulin content was mixed with y amount of dIN based on inulin content to form PDmixx:y. AGmix, ADmix and AEmix: To make AD mix, Aldeltin and Deltin formulations, as described above, were admixed to form a mixed suspension. For the experiments described herein, the Aldeltin:Deltin combination adjuvant was prepared in various ratios ranging from 1:1 to 1:36 weight for weight of inulin content, thereby enabling the amount of Alhydrogel containing particles to be varied relative to the number of non-aluminium containing dIN particles. AG and AE were prepared in the same manner.

PAMP innate immune Activators: PAMP innate immune activators including synthetic triacylated lipoprotein (Pam3CSK4) (0.25 μg/mouse), heat-killed *Listeria monocytogenes* (2.5×10e7 cells/mouse), lipoarabinomannan from *M. smegmatis* (0.25 μg/mouse), LPS-PG ultrapure lipopolysaccharide from *P. gingivalis* (2.5 μg/mouse), standard lipoteichoic acids from *S. aureus* (LTA-SA) (2 μg/mouse), peptidoglycan from *Staphylococcus aureus* (PGN-SA) (2 μg/mouse), synthetic diacylated lipoprotein (0.25 μg/mouse), zymosan (1 mg/mouse), CpG2006 (SEQ ID NO:1) (20 μg/mouse) and monophosphoryl lipid A were all purchased from Invivogen, San Diego, USA and used per the manufacturer's instructions. In addition, synthetic oligodeoxynucleotides (e.g. ODN1826 of the sequence TCCATGACGTTCCTGACGTT (SEQ ID NO:2) synthesized with a phosphorothioate backbone) were purchased from Geneworks, Australia. PAMP innate immune activators were dissolved according to the manufacturer's instructions and diluted into normal saline solution prior to use.

Formulation of inulin Particles with PAMP innate immune Activators: Aqueous suspensions of gIN, dIN, eIN, AG, AD, AE, PG, PD, PE, PG mix, PDmix, PEmix, AGmix, ADmix or AEmix (collectively referred to as "inulin particles"), were prepared as described above. Individual TLR agonists and other PAMP innate immune activators as detailed above were pipetted into the relevant inulin particle suspension to give the desired final concentration. In the same manner, solutions of vaccine antigens, for example, influenza haemagglutinin or HBsAg, were simply pipetted into the relevant immunological formulation to give the desired final vaccine concentration. The mixture of antigen, PAMP innate immune activator and inulin particles was then immediately prior to immunisation drawn up into a syringe ready for injection.

Mouse Immunisations: BALB/c mice at various ages and in group sizes of 5-10 mice per group were immunised intramuscularly in the hind-limb with 50 µl of vaccine in normal saline vehicle. Injections were carried out with a 0.3 ml inulin syringe that has a fused 29G needle (Becton Dickenson. Franklin Lakes, N.J.)

Evaluation of Humoral Response to Antigens: Heparinized blood was collected by retrobulbar puncture of lightly anaesthetized mice as described elsewhere (Michel et al., 1995). Plasma was recovered by centrifugation (7 min at 13,000 rpm). Antigen-specific antibodies in plasma were detected and quantified by an ELISA assay using a standard protocol. Dilutions of plasma were first added to 96-well microtiter plates coated with antigen overnight at room temperature (RT). The bound antibodies were then detected by incubation for 1 hour at 37 C with anti-mouse IgG, IgM, IgG1 or IgG2a conjugated to horse radish peroxidase (HRP) (1:2000 in PBS-Tween, 10% FCS; 100 µl/well), followed by incubation with TMB solution (100 µl/well, Sigma, St. Louis, Mo.) for 30 minutes at RT. The reaction was stopped by the addition of 1M sulfuric acid and absorbance read with an ELISA plate reader.

To determine whether there was a favourable dose-response relationship between a TLR9 agonist (CpG2006 (SEQ ID NO:1) ODN) and an inulin particle formulation (PDmix), female Balb/c mice at 6-8 weeks of age (n=5-8 per group) were immunised intramuscularly twice 14 days apart, with 50 ul of a commercial human trivalent inactivated influenza vaccine (TIV) (Fluvax® 2007) at 100 ng of haemagglutinin per dose, combined with either 2, 7, 20 or 60 µg of CpG2006 (SEQ ID NO:1) alone or mixed with 1 mg PDmix (1:5). Mice were bled 42 days after the second immunization and anti-influenza antibodies measured by ELISA (FIG. 1). Increasing doses of CpG from 2 to 60 ug suppressed the anti-influenza IgG1 response at the same time as enhancing the anti-influenza IgG2a response. However, due to this suppression of IgG1 by the CpG, the overall anti-influenza total IgG response with CpG even at the highest CpG 60 µg dose was not significantly different to that achieved with TIV administered without adjuvant. However, the mice that received CpG2006 (SEQ ID NO:1) with PDmix inulin particles showed a synergistic enhancement of the anti-influenza IgG1 response particularly at the CpG 2 and 7 µg doses, that was in stark contrast to the inhibition of the anti-influenza IgG1 response seen with the same doses of CpG when given alone without inulin particles. The enhancement of total IgG with the combination confirms that inulin particles provide dose-sparing effects for a PAMP innate immune activator such that the benefits of the PAMP innate immune activator on the immune response are obtained at a lower dose when it is administered together with inulin particles. At the same time, the benefits of CpG in terms of enhancing the IgG2a response was retained or even enhanced in the presence of the inulin particles. The anti-influenza total IgG response was greatest in the group that received TIV plus PDmix inulin particles with the PAMP, CpG 60 µg. Similarly, the anti-influenza IgM response was also enhanced to the greatest degree in the CpG and PDmix combination groups.

Example 2

To determine whether the synergistic effect of PDmix and CpG was age-related, a similar experiment to Example 1 was undertaken using female Balb/c mice (n=10/group) that were either just 14 days old (neonatal model) or 200-300 day old (elderly model). First, 14 day old neonatal female BALB/c mice (n=5-7 per group) were immunised intramuscularly in the hindlimb with 50 µl of trivalent inactivated influenza vaccine (TIV) (Fluvax® 2007, CSL Australia) representing a dose of 100 ng HA per animal. TIV was administered alone or mixed with dIN 1 mg, PDmix (1:36 PD:D w/w) 1 mg, CpG1668 20 ug, or PDmix (1:36 PD:D w/w) 1 mg+CpG1668 20 ug. Mice were immunised twice, nine days apart and blood samples collected 14 days after the second immunisation for measurement of anti-influenza antibody responses by ELISA (FIG. 2). The addition of CpG1668 to TIV did not increase influenza-specific total IgG over that seen with influenza antigen alone, although it did result in a switch from an IgG1-predominant to an IgG2a-predominant antibody response, consistent with TLR9 agonists causing a Th2 to Th1 switch in the immune response. Maximal enhancement of anti-influenza total IgG levels was seen when the TIV was formulated with CpG1668 plus PDmix, with a synergistic effect reflected in marked enhancement of anti-influenza total IgG and IgM, to levels greater than those seen with TIV with each of the CpG1668 or PDmix alone. Only the mice that received PDmix together with CpG had a significant increase in influenza haemagglutination inhibition (HI) titres when compared to mice receiving TIV alone. Fifty two days after the second immunisation the mice were sacrificed and influenza-specific T-cell recall responses measured with a CSFE-based T-cell proliferation assay. The mice that received PDmix plus CpG1668 had the highest overall CD4 and CD8 T-cell proliferative responses to influenza antigen. Hence the combination of PDmix, an inulin particle formulation, and CpG, a PAMP innate immune activator that activates TLR9, provided a synergistic enhancement of the immune response to TIV; generating the highest overall anti-influenza total IgG and IgM, being the only group to induce high levels of IgG2a, and increasing protective hemagglutination inhibition (HI) titers in the neonatal mice. Similarly, CD4+ and CD8+ T-cell proliferative recall responses to influenza antigen were also greatest in the combination group. This indicates that the combination of inulin particles and a TLR9 agonist is particularly beneficial in the induction of humoral and cellular immune responses in neonates.

Elderly mice that were 200-300 days old (n=6/group) were immunised intramuscularly twice 14 days apart with TIV (100 ng HA) with or without 1 mg PDmix (1:36), 20 ug CpG1668 or a mixture of the two. Mice were immunised twice, 14 days apart and blood samples collected 14 days after the second immunisation for measurement of anti-influenza antibody responses by ELISA (FIG. 3). The synergistic effects of co-administration of PDmix and CpG1668 on the adaptive immune response were again observed in elderly mice with the group co-administered TIV plus PDmix inulin particles plus the TLR9 agonist CpG2006 (SEQ ID NO:1) achieving the highest influenza-specific total IgG, IgG2a and IgM responses and with the inulin particles attenuating the normal suppression of IgG1 production seen with CpG alone.

Example 3

To determine whether the synergistic effect of PDmix and CpG was dependent on the sequence of the CpG, the experiment in Example 1 was repeated using 6-8 weeks old female Balb/c mice (n=5-7 per group) immunised intramuscularly twice 14 days apart. Mice were immunised intramuscularly with TIV 100 ng HA plus 1 mg PDmix (1:3) alone or together with CpG1668 (Class B ODN), CpG2216 (SEQ ID NO:4) (A class ODN), CpG2006 (SEQ ID NO:1) (Class B ODN), CpG2395 (SEQ ID NO:5) (C class ODN) or a control non-CpG sequence CpG2237 (SEQ ID NO:6), all at a dose of 10 nmol per mouse. Anti-*influenza* antibody levels were determined by ELISA on blood collected 28 days after the second immunisation (FIG. 4) The co-administration of PDmix with either CpG1668, CpG2006 (SEQ ID NO:1) or CpG2395 (SEQ ID NO:5) all showed synergy over the individual components in increasing anti-*influenza* total IgG, IgG2a and IgM titers. CpG2216 (SEQ ID NO:4) and CpG2237 (SEQ ID NO:6) had no effect on the antibody response. This confirms that the synergistic effect of inulin particles and ODN is generalizable to ODN sequences containing a TLR9-binding CpG motif, preferentially belonging to Class B or Class C ODN sequences.

Example 4

To determine whether the synergistic effect of inulin particles (dIn or PDmix) and CpG ODN was dependent on the antigen used, immunizations were repeated with an inactivated rabies vaccine (Merieux Inactivated Rabies Vaccine (MIRV). Female BALB/c mice at 6-8 weeks of age (n=5-7 per group) were immunised intramuscularly twice 14 days apart, with 10 ul of MIRV alone or combined with 1 mg of either dIN or 1 mg PDmix (1:5) alone, or mixed together with CpG1668 (5 μg). Anti-MIRV antibody levels were determined by ELISA on blood collected 14 days after the second immunization (FIG. 6). The combination of either dIN or PDmix with CpG1668 plus MIRV provided the highest anti-rabies total IgG, IgG1, IgG2a and IgM, confirming that the synergistic effect is generalizable to both forms of inulin particles with or without alum content, and the favourable synergistic combination of inulin particles and a TLR9 agonist innate immune activator is generalizable to antigens other than *influenza*. Similar, studies performed in the same manner as the above experiment, confirm that the synergistic immune enhancement effect of inulin particles with CpG ODN extends to a broad range of vaccine antigens, including malaria MSP4 or MSP proteins, recombinant or inactivated SARS CoV antigen, pandemic *influenza* H5N1 antigen, and Japanese encephalitis antigen, with a consistent finding of enhancement of total IgG, IgG2a and IgM and attenuation of the typical suppression of IgG1 mediated by TLR9 agonists.

Example 5

To determine whether the favourable synergistic effect of inulin particles was generalizable to other PAMP innate immune activators, female Balb/c mice at 6-8 weeks of age (n=5-10 per group) were immunised intramuscularly twice 14 days apart, with TIV 2007 (45 ng total HA/mouse) on Day 0 and Day 14. Groups received TIV plus PDmix (1:5) alone or together with 20 ug CpG2006 (SEQ ID NO:1), or one of a range of TLR2 agonists including 1 mg Zymosan, 2 ug lipoteichoic acid (LTA), 0.25 ug Lipomannnan or 0.25 ug Pam3CSK4. Sera were collected 2 weeks after the 2nd injection for measurement of anti-*influenza* antibodies by ELISA. (FIG. 6). The addition of each of the individual PAMPs to the inulin particle-TIV formulation resulted in increased anti-*influenza* total IgG, with the greatest effect from the combination of either CpG a TLR9 agonist or zymosan, a TLR2 agonist. Whereas the combination with CpG suppressed the IgG1 response the combination with zymosan enhanced the IgG1 response, whereas both CpG and zymosan when added to inulin particles markedly enhanced the IgG2a and IgM response, with LTA and PamCSK and lipomannan also enhancing the anti-*influenza* IgG2a and IgM responses, albeit to a lesser degree. This showed that the synergistic immunological effect of inulin particles with TLR9 agonists extended to other PAMPs, including a range of agonists of TLR2.

Example 6

To determine whether the favourable synergistic effect of inulin particles was generalizable to yet other PAMP innate immune activators, female Balb/c mice at 6-8 weeks of age (n=5-10 per group) were immunised intramuscularly twice 14 days apart, with 1 μg recombinant yeast hepatitis B surface antigen (HBsAg) which was combined with either the TLR2 agonist PamCSK4 0.1 μg/mouse, the TLR3 agonist Poly(I:C) 25 μg/mouse, the synthetic TLR4 agonist MPLA, the TLR5 agonist flagellin, the TLR6 agonist MALP-2 0.04 μg/mouse, the TLR7 agonist PolyU 2.5 μg/mouse, or the TLR9 agonist CpG2006 (SEQ ID NO:1) 20 μg/mouse, with or without 1 mg PDmix (1:3). Mice were bled 42 days after the second immunization and anti-HBsAg antibodies measured by ELISA. (FIG. 7). The groups receiving HBsAg plus each of the PAMP innate immune activators alone had low or unmeasurable anti-HBsAg total IgG, IgG1, IgG2a and IgM. By contrast, the groups that received each of the PAMP immune activators plus PDmix showed a marked enhancement in anti-HBsAg total IgG responses consistent with a synergistic effect between the inulin particles and the PAMP innate immune activators tested Example 7

Balb/c mice at 6-8 weeks of age (n=5-8/group) were immunised intramuscularly twice 21 days apart, with 50 μl of a vaccine formulation containing a between 3 ng and 3 μg of *influenza* recombinant H5 (rH5) serotype hemagglutinin protein (rH5) (Protein Sciences Corp, Meriden, USA) plus either dIN 1 mg or dIN 1 mg mixed with CpG2006 (SEQ ID NO:1) 5 μg. Mice were bled 14 days after the second immunization and anti-recombinant H5 antibodies measured by ELISA (FIG. 8). The results showed that when combined with dIN 1 mg plus CpG2006 (SEQ ID NO:1) 5 μg just 10 ng of rH5 induced a higher IgG response than 3 μg of rH5 alone, equivalent to a greater than 300-fold antigen-sparing effect. The antigen-sparing effect was even more dramatic for the IgG2a, IgG2b and IgM responses where rH5 3 ng when combined with dIN 1 mg plus CpG2006 (SEQ ID NO:1) 5 μg induced a higher IgG2a response than 3 μg of rH5 alone, equivalent to a greater than 3000-fold antigen-sparing effect Example 8

Female BALB/c mice 22 months old were immunized i.m. twice 2 weeks apart with 0.1 ug inactivated PR8 H1N1 *influenza* vaccine alone or combined with dIN 1 mg or dIN 1 mg+CpG2006 (SEQ ID NO:1) 10 ug. Additional control groups received saline alone or dIN alone or dIN+CpG alone. All mice were then challenged intranasally at 5 weeks after the second immunization with a lethal dose of PR8 virus (20xLD50). (FIG. 9A). All control elderly mice immunized with saline or adjuvants alone and also mice immunized with PR8 vaccine without adjuvant lost weight and died. Mice immunized with PR8 vaccine plus dIN still became ill and lost weight but then recovered. By contrast elderly mice that had received PR8 vaccine plus the combination of dIN particles with CpG2006 (SEQ ID NO:1) did not become ill, lose weight or died consistent with the combination of inulin particles with a TLR9 agonist having a synergistic effect in restoring the ability of an aged immune system to respond to the vaccine and thereby obtain complete protection against clinical *influenza* infection. To demonstrate that the enhanced protection seen with PR8 virus challenge was not due to the CpG component by itself female BALB/c mice 6-8 weeks old were immunized i.m. with inactivated PR8 *influenza* antigen together with saline, CpG2008 (SEQ ID NO:1), or the combination of din 1 mg and CpG 10 ug at Wk 0 and 3, and mice then challenged at Wk7 with a lethal dose of PR8 H1N1 *influenza* virus, FIG. 9B. Only the mice immunized with PR8 plus the combination of din and CpG survived the challenge whereas the mice immunized with PR8 plus CpG all died, consistent with protection only being mediated by the combined presence of the inulin particles and TLR9 agonist at the time of immunization.

Example 9

Castrated ferrets (Mustelaputoriousfuro, Triple F Farms, Sanger, Pa.) aged 11-14 weeks weighing 0.7 to 1.9 kg were held for fourteen days for acclimation and quarantine. Ferrets were seronegative for currently circulating *influenza* A H1 and H3, *influenza* B viruses, and to H5 antigen. The H5N1 A/Vietnam/1203/2004 Monovalent *Influenza* Subvirion Vaccine: Fisher Repository stock number—CLAG-1170 (lot#U007827) was obtained from the NIAID repository and was stored at 2 to 8° C. The vaccine was administered by intramuscular (IM) thigh injection in a volume of 0.5 mL and the other thigh for the second vaccination. Control animals received either adjuvant alone or an equal volume of buffered saline. Two formulations of inulin adjuvant were used, Lot# VAX-SPL-0910-03 (dIN inulin at 50 mg/ml in bicarbonate buffer, henceforth referred to as Ad1) and Lot# VAX-SPL-0910-04 (dIN inulin at 50 mg/ml inulin content in bicarbonate buffer mixed with CpG2006 (SEQ ID NO:1) at 0.3 mg/ml, henceforth referred to as Ad2). A dose of 250 uL per ferret of each of these formulations was mixed with the H5N1 antigen prior to immunization of each ferret. Thus ferrets received an adjuvant dose of 10 mg of dIN if randomized to receive Ad1 and an adjuvant dose of 10 mg dIn+75 μg CpG2006 (SEQ ID NO:1) if randomized to receive Ad2. CpG2006 (SEQ ID NO:1) with a complete phosphorothioate backbone was purchased from Geneworks Pty Ltd, Adelaide, Australia. Adjuvant was stored at 2-8*C and combined with vaccine immediately before use. *Influenza* virus A/Vietnam/1203/2004 (H5N1) (VN/1203) was obtained from the Centers for Disease Control and Prevention (CDC). Animals were assigned to groups using a stratified (body weight) randomization procedure by a computerized data acquisition system (e.g., Path-Tox; Xybion, Cedar Knolls, N.J.). A total of 49 ferrets were assigned to one of ten groups; Four groups of 7 ferrets each received adjuvanted vaccine twice 21 days apart: 7.5 μg vaccine+Ad1; 7.5 μg vaccine+Ad2; 22.5 μg+Ad1; 22.5 μg vaccine+Ad2. Two groups of 3 ferrets each received vaccine twice without adjuvant: 22.5 μg+No Ad; 7.5 μg+No Ad. Three control groups of three ferrets each received twice: saline+Ad1; saline+Ad2; saline+Saline. One additional group of 6 ferrets received 22.5 μg vaccine+Ad2 administered only once at the time of priming of other groups. Ferrets were infected three weeks after the vaccine booster dose, or six weeks after the priming dose in the group vaccinated only once. For the challenge procedure, following anesthesia with intramuscular ketamine (20 mg/kg) and xylazine (4 mg/kg), $10^6$ EID50 of VN/1203 was instilled in 500 μL into each nare, and the challenge dilution was cultured to ensure consistent infections. Nasal washes were collected by instilling into each nare 1.0 mL of saline containing 1% bovine serum albumin, 100 units penicillin/mL, 100 μg/mL streptomycin, and 0.25 μg amphotericin B/mL. Whole blood for complete blood count was obtained by superior vena cava puncture on day 4 after challenge. Twice daily observations recorded ocular discharge, nasal discharge, sneezing, coughing, stool characteristics, and activity score. Moribund animals were designated by any one of the following criteria: a temperature of less than 33.3° C., weight loss >25%, unresponsiveness to touch, self-mutilation, paralysis, movement disorder, or respiratory distress. In upper respiratory tract samples obtained during life, nasal washes were obtained 2 and 4 days after viral challenge, and throat swabs were obtained 1, 2, 3, 4, and 6, days after challenge. In tissues harvested at necropsy, *influenza* virus was cultured from lavage of a caudal lung lobe and from four 250 mg fragments of homogenized (Tissue-Lyser, QIAGEN, Valencia, Calif.) lung, brain, spleen, tracheobronchial lymph nodes, and two tracheal rings. Serum was collected by vena cava puncture on the day of first vaccination and 14, 21, and 28 days after first vaccination; day 14 post vaccination corresponds to day −28 before challenge, and day 28 post vaccination corresponds to day −14 before challenge. Serum samples were inactivated by receptor-destroying enzyme (Denka-Seiken, Tokyo, Japan) at 37° C. for 16-20 hours followed by heat inactivation at 56° C. for 30 minutes. Hemagglutination inhibition (HI) was performed using horse red blood cells. Titers of neutralizing antibodies were measured by the microneutralization assay (MN). One hundred tissue culture infectious dose 50 (100 TCID50) of VN/1203 virus was mixed with an equal volume of serial dilutions of serum in quadruplicate, incubated for 1 hour at 37° C. and 100 μL of the mixture was added to a prewashed monolayer of MDCK cells in 96 well plates. The plates were incubated for 3 days and the cytopathic effect (CPE) was visually assessed using an inverted microscope. The highest serum dilution protecting more than half of the wells was taken as the antibody titer. Geometric mean titers are reported and a negative titer was denoted as 10. Lung tissue and brain with olfactory bulbs were collected at necropsy from ferrets moribund on days 6 to 8 post-challenge and from surviving ferrets free of symptoms, at day 14 post-challenge. After fixation in buffered formalin, standardized sections were trimmed for histopathology from the left cranial, right middle and right caudal lung lobes. Statistical analyses were performed using GraphPad Prism (version 5.03, GraphPad Software, Inc. La Jolla, Calif.). Serum antibody response was analyzed by analysis of variance (ANOVA) using the Bonferroni post-test correction. Survival proportions were tested using the Log-Rank test. Morbidity by increasing activity score was examined by Fisher's exact test. Viral load was determined to be different by the repeated measure ANOVA.

Ferrets immunized with split-virion H5N1 vaccine without adjuvant, regardless of vaccine dose, did not have detectable H5N1 neutralizing antibody prior to challenge. Ferrets receiving two doses of H5N1 vaccine with Ad1 or Ad2 all demonstrated neutralizing antibody pre-challenge and at 21 days after the priming dose, Ad2-adjuvanted vaccine recipients had significantly higher serum neutralizing antibody than the Ad1 groups (p<0.03, Log Rank-sum test), consistent with the combination of inulin particles plus a PAMP innate immune activator (CpG) providing an enhanced immune response (FIG. 10). Control animals all died after challenge, animals vaccinated with two doses of antigen alone suffered approximately 30% mortality and no mortality was observed in animals vaccinated with antigen combined with either Ad1 or Ad2 (FIG. 11). Recipients of two doses of vaccine without adjuvant lost greater than 15% of body weight by day 5 post-immunization (pi) and the four survivors failed to recover the weight loss. While groups vaccinated with two doses of antigen with Ad1 lost 5% of body weight then recovered, groups vaccinated with two doses of antigen with Ad2 did not lose any weight, consistent with enhanced immune protection when the H5N1 antigen was combined with a formulation of inulin particles plus a PAMP innate immune activator (FIG. 12). Similarly, while 4 ferrets in the Ad1-adjuvanted vaccine groups demonstrated fever, no ferrets in the Ad2-adjuvanted group experienced fever, consistent with a synergistic protective effect between the inulin particles and the PAMP innate immune activator (FIG. 13). Throat swab *influenza* virus titers in Ad2 vaccine recipients on days 2, 3, and 4 pi were significantly lower than in antigen-alone recipients (Mann-Whitney, p=0.0018) while the titers in Ad1 vaccine recipients were not significantly different to the vaccine-alone recipients. Recipients of the single dose of vaccine with Ad2 did not have significant difference in viral loads on day 2-4 pi compared to the two dose antigen-alone groups. Thus the combination of a inulin particle formulation (dIN) with a PAMP innate immune activator (CpG2006 (SEQ ID NO:1)) synergistically enhanced the antibody response to a co-administered antigen and provided enhanced protection against lethal H5N1 challenge, even after just a single immunization. Performance of similar one dose vaccine studies in mice with PR8 antigen conformed that complete protection of mice against lethal PR8 challenge could be obtained by immunizing them with a single dose of 5 ug PR8 combined with dIN and CpG2006 (SEQ ID NO:1) (10 ug), whereas immunization with PR8 with either component alone provided only partial or no protection, respectively.

Example 10

To test whether the synergistic effect of inulin particles when combined with a PAMP innate immune activator, was purely a property of din or was shared by other inulin particle polymorphic forms, adult Balb/c mice were immunized intramuscularly twice 21 days apart, with HBsAg together with either gIN, dIN or eIN inulin particles together with the TLR9 PAMP, CpG2006 (SEQ ID NO:1). Mice were bled 14 days after the second immunization and anti-*influenza* antibodies measured by ELISA (FIG. 14). gIN, dIN or eIN had a synergistic enhancing effect with the CpG in the induction of anti-HBsAg IgG1, IgG2a and IgM consistent with the synergistic effect on PAMP innate immune activators being a shared property of different polymorphic forms of inulin particles Example 11

To determine if the synergistic effects of inulin particles and a PAMP were translatable from small animal models to large mammals, groups of standard bred, female horses (n=3/group), 4-8 years of age and sero-negative to JEV, were immunised with a Japanese encephalitis (JE) vaccine by subcutaneous injections in the neck region. Vero cell culture-grown inactivated JE vaccine (ccJE; Beijing-1 strain) (Toriniwa & Komiya, 2008) obtained from the Kitasato Institute, Japan was given at a dose of 6 µg, either alone or together with a dIN inulin particle formulation (20 mg/dose) or both dIN inulin particle formulation (40 mg/dose) plus CpG7909 (SEQ ID NO:3) (200 ug/dose) in a total injection volume of 1 ml. Horses were boosted with a second dose of the same vaccine after 5-weeks, and sera were collected 5 weeks after the 1st and 2nd immunisations. 50% plaque-reduction neutralisation tests (PRNT50) were performed by incubating ~400 PFU of JEV (Nakayama strain), MVEV (MVE-1-51 stain) or WNV (Kunjin MRM61C strain) in 110 µl HBSS-BSA with serial 2-fold dilutions of antiserum in the same buffer in a 96-well tray at 37° C. for 1 h. Duplicate 0.1 ml aliquots were assayed for infective virus by plaque formation on Vero cell monolayers grown in 6-well tissue culture trays. The percentage plaque reduction was calculated relative to virus controls incubated with naïve serum from the same mouse strain. PRNT50 titers are given as the reciprocal of serum dilutions, which resulted in ≥50% reduction of the number of plaques. Comparison of PRNT50 titers against JEV after 2 doses of vaccine showed that when cOJE was formulated with inulin particles alone, the neutralising antibody responses were augmented by ~4-fold relative to the standard ccJE group. However, the co-administration with ccJE antigen of both inulin particles and CpG7909 (SEQ ID NO:3) resulted in a further 2-3 fold increase in JEV neutralising antibody (Table 1). Notably, all horses receiving ccJE with inulin particles plus CpG achieved a seroprotective antibody titer (PRNT50>10) after just a single dose. The combination of inulin particles with the TLR9 agonist also resulted in the highest level of cross-neutralising antibodies against MVEV and WNV, indicating that this combination is particularly favourable for the induction of cross-neutralising antibodies against other virus strains or even other viruses entirely.

TABLE 1

| Vaccine | JEVPRNT$_{50}$ Post-prime (GMT) | JEV PRNT$_{50}$ Post boost (GMT) | MVEV PRNT$_{50}$ Post boost (GMT) | WNV PRNT$_{50}$ Post boost (GMT) |
| --- | --- | --- | --- | --- |
| ccJE | 11 | 168 | 40 | <10 |
| ccJE + dIN | 14 | 635 | 50 | 21 |
| ccJE + dIN + CpG | 43 | 1600 | 126 | 40 |

Example 12

The anti-inflammatory effects of inulin particles can be conveniently measured by an assay using human whole blood or purified human peripheral blood mononuclear cells (PBMC) or in the alternative if preferred in mouse or other small a species by using purified splenocytes or if the animal is larger e.g. a rabbit, by similarly using their whole blood or purified peripheral blood mononuclear cells. In summary, a titration series of a reducing concentration of the inulin particles, from 1 mg/ml down to 1 ng/ml are added to the cells in a multiwell pate which is then incubated at 37 C or the relevant body temperature of the species from which the cells were obtained. The readout is by measurement of cytokines with IL-1 being especially preferred. The readout can be made after between 4 and 24 hours if cytokine gene expression is being measured by real time PCR or after between about 24 and 72 hours if cytokine protein production is being measured, for example by ELISA. For this example, human PBMC were prepared from 3 healthy adult human subjects and incubated with 100 ug/ml of dIN particles for 5 hours after which the RNA was extracted with TRIZOL and then run on a gene expression array system (Illumina). For control comparison purposes, PBMC from the same subjects were incubated with pro-inflammatory PAMPs including poly(I:C) and LPS. As expected IL-1α and IL-1β mean gene expression across the three human subject PBMC was upregulated by a mean of 4.1 and 4.4 fold, after incubation of PBMC from the 3 subjects with Poly(I:C) or LPS, respectively, when compared to PBMC incubated in the absence of the PAMP agonist. By contrast, IL1a gene expression was reduced 2.88 fold and IL1β gene expression 2.17 fold in PBMCs cultured with dIN particles 100 ug/ml when compared to PBMC incubated alone, dIN particles also downregulated IL1 receptor gene expression, namely IL1RAP which was 1.46 fold downregulated in the presence of inulin particles. Furthermore, further emphasizing their anti-inflammatory action, dIN particles resulted in upregulation of genes that antagonise the inflammatory action of IL-1 including IL1F5 (1.49 fold upregulated), IL1R2 (1.11 fold upregulated), and IL1RN (2.9 fold upregulated). Next the effect of the combination of dIN particles and the TLR9 agonist PAMP, CpG, was examined. In the presence of dIN particles plus CpG, IL1α and IL1β gene expression remained downregulated when compared to expression in unstimulated PBMC alone, but interestingly in the presence of the combination of dIN and CpG the gene expression of IL1 antagonists was even more greatly upregulated than in the presence of dIN alone. Hence with the combined stimulation the effect on genes that antagonise the inflammatory action of IL-1 including IL1F5 (dIN alone vs dIN+CPG) was (1.9 vs 1.49 fold upregulated), IL1R2 (1.35 fold vs 1.11 fold upregulated), and IL1RN (3.47 fold 2.94 fold upregulated). Thus, even more surprisingly the combination of inulin particles with the TLR9 agonist PAMP resulted in even greater enhancement of the anti-inflammatory properties of the inulin particles alone. Conversely, in the same assay genes associated with anti-inflammatory effects were consistently elevated. Thus, the anti-inflammatory gene, PPARg, was consistently downregulated in PBMC incubated with PAMCSK, poly(I:C), LPS and all other TLR agonists tested, but was upregulated by a mean of 1.24 fold when PBMC from the three human subjects were incubated with dIN particles. Matching results were obtained when proteins levels of the same and related pro-inflammatory markers were measured in human PBMC after 24-48 hours incubation with a PAMP, or inulin particles, with protein levels being measured by cytokine ELISA or by Western blot. The results showed that expression of PAMP-stimulated inflammatory cytokines including IL-1 by human PBMC incubated with whole live or inactivated virus (JEV) or purified PAMPs, is reduced in the presence of inulin particles in the PBMC cultures. gIN and eIN particles showed identical effects to dIN in respect of their ability to inhibit IL-1 gene and protein expression and to upregulate expression of anti-inflammatory members of the IL1 pathway, and PPARγ, making this a generalizable property of all inulin particles tested.

As part of a human H1N1 2009 pandemic *influenza* vaccine study, dIN was administered to human subjects in a dose of 20 mg per immunisation combined with a recombinant H1N1 2009 haemagglutinin antigen (rHA). The frequency of headache was significantly lower ($p<0.05$ by Fishers exact test) in subjects receiving Advax™ adjuvant (4/137: 2.9%), compared to rHA alone (15/137: 10.9%). After the second immunization there was again a trend ($p=0.06$) to less post-immunization headaches in groups receiving Advax™ adjuvant (2/135: 1.5%) compared to rHA alone (8/137: 5.8%). Reduction in headaches would be consistent with inulin particle-induced inhibition of IL-1 production, as IL-1 serum levels are increased in cluster headaches and IL-1 gene polymorphisms (3953 C/T) are associated with migraine headaches (Martelletti et al., 1993; Rainero et al., 2002). This indicates at a proven adjuvant-effective dose in humans, inulin particles are also having an anti-inflammatory effect

Example 13

To determine whether the favourable synergistic effect of inulin particles as was generalizable to yet other PAMP innate immune activators, female Balb/c mice at 6-8 weeks of age (n=5-10 per group) were immunised intramuscularly twice 14 days apart, with 1 μg recombinant yeast hepatitis B surface antigen (HBsAg) which was combined with either the TLR2 agonist PamCSK4 0.1 μg/mouse, the TLR3 agonist Poly(I:C) 25 μg/mouse, the synthetic TLR4 agonist MPLA, the TLR5 agonist flagellin, the TLR6 agonist MALP-2 0.04 μg/mouse, the TLR7 agonist PolyU 2.5 μg/mouse, or the TLRB agonist CpG2006 (SEQ ID NO:1) 20 μg/mouse, with or without 1 mg PDmix (1:3). Mice were bled 42 days after the second immunization and anti-HBsAg antibodies measured by ELISA. The groups receiving HBsAg plus each of the PAMP innate immune activators alone had low anti-HBsAg total IgG, IgG1, IgG2a and IgM. By contrast, the groups that received each of the PAMP immune activators plus PDmix showed a marked enhancement in anti-HBsAg total IgG responses consistent with a synergistic effect between the inulin particles and the PAMP innate immune activators tested.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in USA or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

```
<110> Vaxine Pty Ltd <120> Enhanced Immunological
Composition <130> Confirmation No 4837
<140> U.S. 14/127,489 <141> 2013 Dec. 19 <160> 6
<170> PatentIn version 3.5
<210> 1
<211> 20
<212> DNA
<213> Artificial
sequence <220> <223> synthetic oligonucleotide
<400> 1
tcgtcgtttt gtcgttttgt cgtt
<210> 2
<211> 20
<212> DNA
<213> Artificial sequence <220>
<223> synthetic oligonucleotide
<400> 2
tccatgacgt tcctgacgtt
<210> 3
<211> 20
<212> DNA
<213> Artificial
sequence <220> <223> synthetic oligonucleotide
<400> 3
tccatgacgt tcctgacgtt
<210> 4
<211> 24
<212> DNA
<213> Artificial sequence <220>
<223> synthetic oligonucleotide <400> 4 gggggacgat
cgtcgggggg <210> 5 <211> 22 <212> DNA
<213> Artificial sequence
<220>
<223> Synthetic
oligonucleotide <400> 5
tcgtcgtttt cggcgcgcgc cg
<210> 6
<211> 24
<212> DNA
<213> Artificial
sequence <220> <223> Synthetic
oligonucleotide <400> 6 tgctgcttttt gtgcnttgt gctt
```

CITATION LIST

Bilkei-Gorzo, A, Food Chem Toxicol 31(5):357-361 (1993).
Cooper, P D and M Carter, Mol Immunol 23(8):895-901 (1986).
Cooper, P D and E J Steele, Immunol Cell Biol 66:345-352 (1988).
Cooper, P D and E J Steele, Vaccine 9:351-357 (1991).
Crapper, D R et al., Science 180(85):511-513 (1973).
Garruto, R M et al., Acta Neuropathol 78(2). 210-219 (1989).
Kawahara, M et al., Brain Res Bull 55(2):211-217 (2001).
Petrik, M S et al., Neuromolecular Medicine 9(1):83-100 (2007).
Phelps, C F, Biochem J, 95:41-47 (1965).
Verroust, P J at al., Kidney Int 6:157-169 (1974).
Gordon et al., Safety, Journal of Infectious Disease, 171. pp. 1576-1585, (1995)
Tong N K, Beran J, Kee S A at al. Kidney Int. 2005 November; 68(5):2298-303.
Matzinger P. Science. 2002 Apr. 12; 296(5566):301-5.
Petrovsky N, Aguilar J C Immunol Cell Biol. 2004 October; 82(5):488-96.
Israeli E. et al. Clin Rev Allergy Immunol. 2010 Sep. 30.
Bondy S C. Neurotoxicology. 2010 September; 31(5):575-81.
Durando P, Icardi G, Ansaldi F. Expert Opin Biol Ther. 2010 April; 10(4):639-51.
Prince G A, Jenson A B, Hemming V G, et al. J Virol. 1988 March; 57(3):721-8.
Heine H, Ulmer A J. Chem Immunol Allergy. 2005; 86:99-119.
Werling D, Jungi T W. Vet Immunol Immunopathol. 2003 Jan. 10; 91(1):1-12.
Eisenbarth S C, Colegio O R, O'Connor W, et al. Nature. 2008 Jun. 19; 453(7198):1122-6.
Kandimalla E R, Struthers M, Bett A J, et al. Cell Immunol. 2011 Apr. 22.
Schasfoort, Richard B M (Editor) and Tudos Anna J (Editor) (2008). Handbook of Surface Plasmon Resonance. RSC publishing. ISBN 978-0-85404-267-8.
Buckner D, Wilson S, Kurk S, et al. J Biomol Screen. 2006 September; 11(6):664-71.
Kasturl S P, Skountzou I, Albrecht R A, et al. Nature. 2011 Feb. 24; 470(7335):543-7.
Querec T, Bennouna S, Alkan S, et al. J Exp Med. 2006 Feb. 20; 203(2):413-24.
Martelletti P, Granata M. Giacovazzo M., Cephalalgla 1993 October; 13(5):343-5
Rainero I, Pinessi L, Salani G, Valfre W, Rivoiro C, Savl L, et al., Headache 2002 May; 42(5):337-40.

The invention claimed is:

1. A immunogenic vaccine composition comprising:
   (a) manufactured particles of delta inulin;
   (b) a synthetic substance comprising one or more, but no greater than ten distinct molecular species of pathogen-associated molecular pattern (PAMP); and
   (c) an antigen.

2. The vaccine composition of claim 1 wherein the synthetic substance comprising or consisting of a PAMP comprises or consists of a substance that is selected from the group consisting of an agonist of one or more of a Toll-like receptor (TLR), a RIG ligase, a NOD-like receptor, a RNA helicase receptor, or a NALP.

3. The vaccine composition of claim 1 wherein the synthetic substance comprising or consisting of a PAMP consists of a substance that is selected from the group consisting of lipoteichoic acid, RNA, DNA, oligonucleotide, and an unmethylated polynucleotide molecule.

4. A The vaccine composition of claim 1 wherein the vaccine composition further comprises an antigen-binding carrier material.

5. The vaccine composition of claim 1 wherein the antigen Is selected from the group comprising influenza virus, hepatitis B virus, rabies virus antigens iii a corona-virus from the family of Coronaviridae.

6. The vaccine composition of claim 1 wherein the synthetic substance comprising a PAMP is a synthetic CG-motif containing oligonucleotide.

7. The vaccine composition of claim 1 wherein the antigen is selected from the group of a protein, peptide, polysaccharide, lipid, allergen, polynucleotide molecule, polynucleotide molecule encoding an antigenic peptide or protein, viral vector, microorganism, parasite, bacterium and a virus.

* * * * *